US008148149B2

(12) United States Patent
Nigam et al.

(10) Patent No.: US 8,148,149 B2
(45) Date of Patent: *Apr. 3, 2012

(54) METHODS OF INDUCING TUBULOGENESIS AND/OR BRANCHING MORPHOGENESIS OF KIDNEY CELL CULTURES

(75) Inventors: Sanjay Kumar Nigam, Del Mar, CA (US); Hiroyuki Sakurai, San Diego, CA (US); Kevin T. Bush, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 1115 days.

This patent is subject to a terminal disclaimer.

(21) Appl. No.: 12/009,030

(22) Filed: Jan. 15, 2008

(65) Prior Publication Data

US 2008/0299655 A1   Dec. 4, 2008

Related U.S. Application Data

(60) Division of application No. 10/608,783, filed on Jun. 27, 2003, now Pat. No. 7,326,570, which is a continuation-in-part of application No. PCT/US02/20673, filed on Jun. 28, 2002, said application No. 10/608,783 is a continuation-in-part of application No. 09/595,195, filed on Jun. 16, 2000, now Pat. No. 7,074,552, said application No. 10/608,783 is a continuation-in-part of application No. 09/965,651, filed on Sep. 25, 2001, now abandoned.

(60) Provisional application No. 60/301,684, filed on Jun. 28, 2001, provisional application No. 60/426,152, filed on Nov. 14, 2002.

(51) Int. Cl.
*C12N 5/07* (2010.01)

(52) U.S. Cl. ........ 435/369; 435/375; 435/395; 435/325; 435/405

(58) Field of Classification Search .................. None
See application file for complete search history.

(56) References Cited

U.S. PATENT DOCUMENTS

2003/0007954 A1   1/2003   Naughton et al. ........... 424/93.7

OTHER PUBLICATIONS

Milner, et al., "A Novel 17 kD Heparin-Binding Growth Factor (HBGF-8) in Bovine Uterus: Purification and N-Terminal Amino Acid Sequence", *Biochemical and Biophysical Research Communications*, Vp;/ 165, No. 3, pp. 1096-1103, Dec. 29, 1989.
Mitsiadis, et al., "Expression of the heparin-binding cytokines, midkine (MK) and HB-GAM (pleiotrophin) is associated with epithelial-mesenchymal interactions during fetal development and organogenesis", *Development*, vol. 121, pp. 37-51, 1995.

Sato, et al., "Pleiotrophin as a Swiss 3T3 Cell-Derived Potent Mitogen for Adult Rat Hepatocytes", *Experimental Cell Research*, vol. 246, No. 1, pp. 152-164, Jan. 10, 1999.
Kurtz, et al., "Pleiotrophin and Midkine in Normal Development and Tumor Biology", *Critical Reviews in Oncogenesis*, vol. 6, No. 2, pp. 151-177, 1995.
Rauvala, et al. "Expression of HB-GAM (heparin-binding growth-associated molecules) in the pathways of developing axonal processes in vivo and neurite outgrowth in vitro induced by HB-GAM" *Developmental Brain Research*, Voll. 79, pp. 157-176, 1994.
Imai, et al., Osteoblast Recruitment and Bone Formation Enhanced by Cell Matrix-associated Heparin-binding Growth-associated Molecule (HB-GAM), *The Journal of Cell Biology*, vol. 143, No. 4, pp. 1113-1128, Nov. 16, 1998.
Tomita, et al, "Direct in Vivo Gene Introduction into Rat Kidney", *Biochemical and Biophysical.Research Communications*, vol. 186, No. 1, pp. 129-134, Jul. 15, 1992.
Zhu, et al., "Systemic Gene Expression After Intravenous DNA Delivery into Adult Mice", *Science*, vol. 261, pp. 209-211, Jul. 9, 1993.
Moullier, et al., "Adenoviral-mediated gene transfer to renal tubular cells in vivo", *Kidney International*, vol. 45, pp. 1220-1225, 1994.
Montesano, et al., "Induction of Epithelial tubular Morphogenesis in Vitro by Fibroblast-Derived Soluble Factors", *Cell*, vol. 66, pp. 697-711, Aug. 23, 1991.
Bladt, et al., "Essential role for the c-met receptor in themigration of myogenic precursor cells into the limb bud", *Nature*, vol. 376, No. 6543, pp. 68-771, Aug. 31, 1995.
Schmidt, et al., "Scatter factor/hepatocyte growth factor is essential for liver development", *Nature*, vol. 373, No. 6516, pp. 699-702, Feb. 23, 1995.
Schuchardt, et al., "Renal agenesis and hypodysplasia in ret-k-mutant mice result from defects in ureteric bud development", *Development*, vol. 122, No. 6, pp. 1919-1929, Jun. 1996.
Metzger, et al., "Genetic Control of Branching Morphogenesis", *Science*, vol. 284, pp. 1635-1639, Jun. 4, 1999.
Ohuchi, et al., "FGF10 Acts as a Major Ligand for FGF Receptor 2 IIIb in Mouse Multi-Organ Development", *Biochemical and Biophysical Research Communications*, vol. 277, No. 3, pp. 643-649, Nov. 2, 2000.
Bullock, et al., "Renal agenesis in mice homozygous for a gene trap mutation in the gene encoding heparan sulfate 2-sulfotransferase", *Genes & Development*, vol. 12, No. 12, pp. 1894-1906, Jun. 15, 1998.
Bullock, et al., "Developmental and species differences in the response of the ureter to metabolic inhibition", *European Journal of Physiology*, vol. 436, No. 3, pp. 443-448, Aug. 1998.
Davies, et al., "Sulphated proteoglycan is required for collecting duct growth and branching but not nephron formation during kidney development", *Development*, vol. 121, Issue 5, pp. 1507-1517, 1995.
Kispert, et al., "Proteoglycans are required for maintenance of Wnt-11 expression in the ureter tips" *Development*, vol. 122, pp. 3627-3637, 1996.
Montesano, et al., "Identification of a Fibroblast-Derived Epithelial Morphogen as Hepatocyte Growth Factor", *Cell*, vol. 67, No. 5, pp. 901-908, Nov. 29, 1991.
Zelzer, et al., "Cell fate choices in *Drosophila* tracheal morphogenesis", *BioEssays*, vol. 22, No. 3, pp. 219-226, Mar. 2000.
Enomoto, et al., "GFRα-1 Deficient Mice Have Deficits in the Enteric Nervous System and Kidneys", *Neuron*, vol. 21, No. 2, pp. 317-324, Aug. 1998.

(Continued)

*Primary Examiner* — Allison Ford
(74) *Attorney, Agent, or Firm* — Joseph R. Baker, Jr.; Gavrilovich, Dodd & Lindsey LLP

(57) ABSTRACT

Provided are methods and compositions for constructing stable mammalian embryonic epithelial tissues and organs as well as constructing kidney tissue, and treating renal failure. Disclosed are methods of using an active epithelial growth factor having the capability of effectuating induction of growth and morphogenesis is cells.

15 Claims, 28 Drawing Sheets

OTHER PUBLICATIONS

Imai, et al., "Towards gene therapy for renal diseases", *Nephrologie*, vol. 18, No. 7, pp. 397-402, 1998.

Imai, et al., "Gene transfer and kidney disease", *Journal of Nephrology*, vol. 11, No. 1, pp. 16-19, Jan.-Feb. 1998.

Imai, et al., "Strategies of gene transfer fo the kidney", *Kidney*, vol. 53, No. 2, pp. 264-272, Feb. 1998.

Meng, et al., "Pleiotrophin signals increased tyrosine phosphorylation of β-catenin through inactivation of the intrinisic catalytic activity of the receptor-type protein tyrosine phosphatase βζ", *Proc. Natl. Acad. Sci.*, vol. 97, No. 6, pp. 2603-2608, Mar. 14, 2000.

Vainio, et al., "Epithelial-Mesenchymal Interactions Regulate the Stage-Specific Expression of a Cell Surface Proteoglycan, Syndecan, in the Developing Kidney", *Developmental Biology*, vol. 134, No. 2, pp. 382-391, Aug. 1989.

Vainio, et al., "Syndecan and Tenascin Expression is Induced by Epithelial-Mesenchymal Interactions in Embryonic Tooth Mesenchyme", *The Journal of Cell Biology*, vol. 108, No. 5, pp. 1945-1954, May 1989.

Ohuchi, et al., "Renal tubular effects of endothelin-B receptor signaling: its role in cardiovascular homeostasis and extracellular vol. regulation", *Curr Opin Nephrol Hyperten.*, vol. 9, No. 4, pp. 435-439, Jul. 2000.

Thadhani, et al., "Acute renal failure", *The New England Journal of Medicine*, vol. 334, No. 2, pp. 1448-1460, May 30, 1996.

Bonventre, et al., "Acture renal failure. I. Relative importance of proximal vs. distal tubular injury", *Am. J. Physiol*, vol. 275, No. 5, pp. F623-F631, Nov. 1998.

Molitoris, et al., "Acute renal failure. II. Experimental models of acute renal failure: imperfect but indispensable", *Am. J. Physiol. Renal Physiol.*, vol. 278, No. 1, pp. F1-F12, Jan. 2000.

Fish, et al., "Alterations of Epithelial Polarity and the Pathogenesis of Disease States", *The New England Journal of Medicine*, vol. 330, No. 14, pp. 1580-1588, Apr. 7, 1994.

Tsukamoto, et al., "Tight Junction Proteins Form Large Complexes and Associate with the Cytoskeleton in an ATP D epletion Model for Reversible Junction Assembly", *The Journal of Biological Chemistry*, vol. 272, No. 26, pp. 16133-16139, Jun. 27, 1997.

Hammerman, et al., "Acute renal failure. III. The role of growth factors in the process of renal regeneration and repair", *Am. J. Physiol. Renal Physiol.*, vol. 279, No. 1, pp. F3-F11, Jul. 2000.

Gailit, et al., "Redistribution and dysfunction of integrins in cultured renal epithelial cells exposed to oxidative stress", *American Journal of Physiology*, vol. 264, No. 1, pp. F149-F157, Jan. 1993.

Lieberthal, et al., "β Integrin-Mediated Adhesion between Renal Tubular Cells after Anoxic Injury", *Journal of the American Society of Nephrology*, vol. 8, Issue 2, pp. 175-183, Feb. 1997.

Zuk, et al., "Polarity, integrin, and extracellular matrix dynamics in the postischemic rat kidney", *American Journal of Physiology*, vol. 275, No. 3, pp. C711-C731, Sep. 1998.

Gumbiner, et al., "The Role of the Cell Adhesion Molecule Uvomorulin in the Formation and Maintenance of the Epithelial Junctional Complex", *The Journal of Cell Biology*, vol. 107, No. 4, pp. 1575-1587, Oct. 1988.

McNeill, et al., "Novel Function of the Cell Adhesion Molecule Uvomorulin as an Inducer of Cell Surface Polarity", *Cell*, vol. 62, No. 2, pp. 309-316, Jul. 27, 1990.

Mandel, et al., ATP depletion: a novel method to study junctional properties in epithelial tissues. II. Internalization of $Na^+$, $K^+$-ATPase and E-cadherin", *Journal of Cell Science*, vol. 107, Part 12, pp. 309-316, Dec. 1994.

Tsukita, et al., "Structural and signalling molecules come together at tight junctions", *Current Opinion in Cell Biology*, vol. 11, No. 5, pp. 628-633, Oct. 1999.

Denker, et al., "Molecular structure and assembly of the tight junction", *American Journal of Physiology*, vol. 274, No. 1, pp. F1-F9, Jan. 1998.

Gopalakrishnan, et al., "Rho GTPase signaling regulates tight junction assembly and protests tight junctions during ATP depletion", *American Journal of Physiology*, vol. 275, No. 3, pp. C798-C809, Sep. 1998.

Kuznetsov, et al., "Folding of Secretory and Membrane Proteins", *The New England Journal of Medicine*, vol. 339, No. 23, pp. 1688-1695, Dec. 3, 1998.

Van Why, et al., "Thresholds for cellular disruption and activation of the stress response in renal epithelia", *American Journal of Physiology*, vol. 277, No. 2, pp. F227-F234, Aug. 1999.

Gething, et al., "Protein folding in the cell", *Nature*, vol. 355, No. 6355, pp. 33-45, Jan. 1992.

Gabai, et al., "Rise in heat-shock protein level confers tolerance to energy deprivation", *FEBS Letters*, vol. 327, No. 3, pp. 247-250, Aug. 1993.

Georgopoulos, et al., "Role of the major heat shock proteins as molecular chaperones", *Annual Review of Cell Biology*, vol. 9, pp. 601-634, 1993.

Yoo, et al., "Anti-Inflammatory Effect of Heat Shock Protein Induction is Related to Stabilization of IκBα Through Preventing IκB Kinase Activation in Respiratory Epithelial Cells", *The Journal of Immunology*, vol. 164, No. 10, pp. 5416-5423, May 15, 2000.

Rauchman, et al., "An osmotically tolerant inner medullary collecting duct cell line from an SV40 transgenic mouse", *American Journal of Physiology*, vol. 265, No. 3, pp. F416-F424, Sep. 1993.

Barasch, et al., "A ureteric bud cell line induces nephrogenesis in two steps by two distinct signals", *American Journal of Physiology*, vol. 271, No. 1, pp. F50-F61, Jul. 1996.

Barasch, et al., "Ureteric bud cells secrete multiple factors, including bFGF, which rescue renal progenitors from apoptosis", *American Journal of Physiology*, vol. 273, No. 5, pp. F757-F767, Nov. 1997.

Laitinen, et al., "Changes in the Glycosylation Pattern During Embryonic Development of Mouse Kidney as Revealed with lectin Conjugates", *The Journal of Histochemistry and Cytochemistry*, vol. 35, No. 1, pp. 55-65, 1987.

Gilbert, et al., "Defect of Nephrogenesis Induced by Gentamicin in Rat Metanephric Organ Culture", *Laboratory Investigation*, vol. 70, No. 5, pp. 656-666, May, 1994.

O'Rourke, et al., "Expression of c-ret promotes morphogenesis and cell survival in mIMCD-3 cells", *American Journal of Physiology*, vol. 276, No. 4, pp. F581-F589, Apr. 1999.

Al-Awqati, et al., "Architectural patterns in branching morphogenesis in the kidney", *Kidney International*, vol. 54, No. 6, pp. 1832-1842, Dec. 1998.

Liu, et al., "Comparative Role of Phosphotyrosine Kinase Domains. Of c-ros and c-ret Protooncogenes in Metanephric Development with Respect to Growth Factors and Matrix Morphogens", *Developmental Biology*, vol. 178, pp. 133-148, 1996.

Rauvala, et al., "An 18-kd heparin-binding protein of developing brain that is distinct from fibroblast growth factors", *The EMBO Journal*, vol. 8, no. 10, pp. 2933-2941, 1989.

Li, et al., "Cloning and Expression of a Developmentally Regulated Protein that Induces Mitogenic and Neurite Outgrowth Activity", *Science*, vol. 250, No. 4988, pp. 1690-1694, Dec. 21, 1990.

Vanderwinden, et al., "Cellular distribution of the new growth factor Pleiotrophin (HB-GAM) mRNA in developing and adult rat tissues", *Anat. Embryol*, vol. 186, pp. 387-406, 1992.

Kuznetsov, et al., "Perturbations in maturation of secretory proteins and their association with endoplasmic reticulum chaperones in a cell culture model for epithelial eschemia", *Proc. Natl. Acad. Sci.*, vol. 93, pp. 8584-8589, Aug. 1996.

Molitoris, et al., "Role of the actin cytoskeleton in ischemia-induced cell injury and repair", *Pediatric Nephrol.*, vol. 11, pp. 761-767. 1997.

Bush, et al., "Selective degradation of E-cadherin and dissolution of E-cadherin-catenin complexes in epithelial ischemia", *Am. J. Physiol. Renal Physiol.*, vol. 278, pp. F847-852, 2000.

Bush, et al., "Pretreatment with inducers of ER molecular chaperones protects epithelial cells subjected to ATP depletion", *Am. J. Physiol. Renal Physiol.*, vol. 277, pp. F211-218, 1999.

Harrunerman, et at., "Acute renal failure. III. The role of growth factors in the process of renal regeneration and repair", *Am. J. Physiol. Renal Physiol.*, vol. 279, pp. F3-F11, 2000.

Steinberg, et al., "Cadherins and their connections: adhesion junctions have broader functions", *Curr. Opin. Cell Biol.*, vol. 11, No. 5, pp. 554-560, Oct. 1999.

Le, et al., "Recycling of E-Cadherin: A Potential Mechanism for Regulating Cadherin Dynamics", *The Journal of Cell Biology*, vol. 146, No. 1, pp. 219-232, Jul. 12, 1999.

Denker, et al., "Molecular structure and assembly of the tight junction", *Am. J. Physiol. Renal Physiol*, vol. 274, pp. F1-F9, 1998.

Tsukamoto, ' et al., "Role of tyrosine phosphorylation in the reassembly of occludin and other tight junction proteins", *Am. J. Physiol Renal Physiol.*, vol. 276, pp. F737-750, 1999.

Ye, et al., "A role for intracellular calcium in tight junction reassembly after ATP depletion-repletion", *Am. J. Physiol. Renal Physiol.*, vol. 277, pp. F524-F532, 1999.

Nigam, et al., "A Set of Endoplasmic Reticulum Proteins Possessing Properties of Molecular Chaperones Includes $Ca^{2+}$-binding Proteins and Members of the Thioredoxin Superfamily", *The Journal of Biological Chemistry*, vol. 269, No. 3, pp. 1744-1749, Jan. 21, 1994.

Bush, et al., "Proteasome Inhibition Leads to a Heat-shock Response, Induction of Endoplasmic Reticulum Chaperones, and Thermotolerance", *The Journal of Biological Chemistry*, vol. 272, No. 14, pp. 9086-9092, Apr. 4, 1997.

Dong, et al., "Intracellular $CA^{2+}$ Thresholds That Determine Survival or Death of Energy-Deprived Cells", *American Journal of Pathology*, vol. 152, No. 1, pp. 231-240, Jan. 1998.

Kribben et al "Evidence for Role of Cytosolic Free Calcium in Hypoxia-Induced Proximal Tubule Injury", *J. Clin. Invest.*, vol. 93, pp. 1922-1929, May, 1994.

Liu, et al., "Endoplasmic Reticulum Stress Proteins Block Oxidant-induced $CA^{2+}$ Increases and Cell Death", *The Journal of Biological Chemistry*, vol. 273, No. 21, pp. 12858-12862, May 22, 1998.

Yu, et al., "The Endoplasmic Reticulum Stress-Responsive Protein GRP78 Protects Neurons Against Excitotoxicity and Apoptosis: Suppression of Oxidative Stress and Stabilization of Calcium Homeostasis", *Experimental Neurology*, vol. 155, No. 2, pp. 302-314, Feb. 1999.

Bian, et al., "Roles of Cytoplasmic $Ca^{2+}$ and intracellular $CA^{2+}$ stores in induction and suppression of apoptosis in S49 cells", *American Journal of Physiology*, vol. 272, No. 4, pp. C1241-C1249, Apr. 1997.

Bush, et al., "Genesis and reversal of the ischemic phenotype in epithelial cells", *The Journal of Clinical Investigation*, vol. 106, No. 5, pp. 621-626, Sep. 2000.

Qiao, et al., "Branching morphogenesis independent of mesenchymal-epithelial contact in the developing kidney", *Proc. Natl. Acad. Sci.*, vol. 96, pp. 7330-7335, Jun. 1999.

Santos, et al., "Modulation of HGF-Induced Tubulogenesis and Branching by Multiple Phosphorylation Mechanisms", *Developmental Biology*, vol. 159, pp. 535-548, 1993.

Santos, et al., "HGF-Induced Tubulogenesis and Branching of Epithelial Cells is Modulated by Extracellular Matrix and TGF-β", *Developmental Biology*, vol. 160, pp. 293-302, 1993.

Santos, et al., "Involvement of Hepatocyte Growth Factor in Kidney Development", *Developmental Biology*, vol. 163, pp. 525-529, 1994.

Barros, et al., "Differential tubulogenic and branching morphogenetic activities of growth factors: Implications for epithelial tissue development", *Proc. Natl. Acad. Sci.* vol. 92, pp. 4412-4416, May,1995.

Pavlova, et al., "Evolution of gene expression patterns in a model of branching orphogenesis", *Am. J. Physiol. Renal Physiol.*, vol. 277, pp. F650-F663, 1999.

Grobstein, et al., "Inductive Epithelio-mesenchymal Interaction in Cultured Organ Rudiments of the Mouse", *Science*, vol. 118, No. 3053, pp. 52-55, Jul. 3, 1953.

Grobstein, "Morphogenetic Interaction between Embryonic Mouse Tissues separated by a Membrane Filter", *Nature*, vol. 172, pp. 869-871, Jul. 4, 1953-Dec. 26, 1953.

Grobstein, et al., "Inductive Interaction in the Development of the Mouse Metanephros", *The Journal of Experimental Zoology*, vol. 130, pp. 319-339, Oct. Nov. Dec. 1955.

Saxen, *Organogenesis of the Kidney*, (table of contents) Cambridge University Press, Cambridge, 1987.

Davies, et al., "Inductive Interactions between the Mesenchyme and the Ureteric Bud", *Experimental Nephrology*, vol. 4, pp. 77-85, Mar.-Apr. 1996.

Vainio, et al., "Inductive Tissue Interactions, Cell Signaling and the Control of Kidney Organogenesis", *Cell*, vol. 90, pp. 975-978, Sep. 19, 1997.

Schofield, et al., "Growth Factors and Metanephrogenesis", *Experimental Nephrology*, vol. 4, pp. 97-104, Mar.-Apr. 1996.

Nigam, "Determinants of branching tubulogenesis", *Current Opinion in Nephrology and Hypertension*, Vo. 4, No. 3, pp. 209-214, 1995.

Sakurai, et al., "In vitro branching tubulogenesis: Implications for developmental and cystic disorders, nephron number, renal repair, and nephron engineering", *Kidney International*, vol. 54, pp. 14-26, 1998.

Schuchardt, et al., "Defects in the kidney and enteric nervous sytem of mice lacking the tyrosine kinase receptor Ret", *Nature*, Vo. 367, pp. 380-383, Jan. 27, 1994.

Durbec, et al., "GDNF signalling through the Ret receptor tyrosine kinase", *Nature*, vol. 381, No. 6585, pp. 798-793, Jun. 27, 1996.

Sanchez, et al., "Renal agenesis and the absence of enteric neurons in mice lacking GDNF", *Nature*, vol. 382, No. 6586, pp. 70-73, Jul. 4, 1996.

Pichel, et al., "Defects in enteric innervation and kidney development in mice lacking GDNF", *Nature*, vol. 382, No. 6586, pp. 73-76, Jul. 4, 1996.

Moore, et al., "Renal and neuronal abnormalities in mice lacking GDNF", *Nature*, vol. 382, No. 6586, pp. 76-79, Jul. 4, 1996.

Pepicelli, et al., "Rapid Communication GDNF Induces Branching and Increased Cell Proliferation in the Ureter of the Mouse", *Developmental Biology*, vol. 192, pp. 193-198, 1997.

Sakurai, et al., "An in vitro tubulogenesis system using cell lines derived from the embryonic kidney shows dependence on multiple soluble growth factors", *Proc. Natl. Acad. Sci.*, vol. 94, pp. 6279-6284, Jun. 1997.

Cantley, et al., "Regulation of mitogenesis, motogenesis, and tubulogenesis hepatocyte growth factor in renal collecting duct cells", *American Journal of Physiology*, vol. 267, No. 2, pp. F271-F280, Aug. 1994.

Barros, et al., "Differential tubulogenic and branching morphogenetic activities of growth factors: Implications for epithelial tissue development", *Proc. Natl. Acad. Sci.*, vol. 92, pp. 4412-4416, May, 1995.

Sakurai, et al., "EGF receptor ligands are a large fraction of in vitro branching morphogens secreted by embryonic kidney ", *Am. J. Physiol*. vol. 273, No. 3, pp. F463-F472, Sep. 1997.

Gumbiner, "Eithelial Morphogenesis", *Cell*, vol. 69, pp. 385-387, May 1, 1992.

Rodriguez-Boulan, et al., "Morphogenesis of the Polarized Epithelial Cell Phenotype", *Science*, vol. 245, pp. 718-725, Aug. 18, 1989.

Sukhatme, "Renal Development: Challenge and Opportunity", *Seminars in Nephrology*, vol. 12,.No. 4, pp. 422-426, Sep. 1993.

Vega, et al., "Glial cell line-derived neurotrophic factor activates the receptor tyrosine kinase RET and promotes kidney morphogenesis", *Proc. Natl. Acad. Sci.*, vol. 93, pp. 10657-10661, Oct. 1996.

Sainio, et al., "Glial-cell-line-derived neurotrophic factor is required for bud initiation from ureteric epithelium", *Development*, vol. 124, pp. 4077-4087, Oct. 1997.

Sweet, et al:, "Impaired Organic Anion Transport in Kidney and Choroid Plexus of Organic Anion Transporter 3 (*Oat3* (*Slc22a8*)) Knockout Mice", *The Journal of Biological Chemistry*, vol. 277, No. 30, pp. 26934-26943, Jul. 26, 2002.

Sweet, et al., "The organic anion transporter family: from physiology to ontogeny and the clinic", *Am. J. Physiol. Renal Physiol*. vol. 281, pp. F197-F205, 2001.

Steer, et al. "A strategy for in vitro propagation of rat nephrons Rapid Communication", *Kidney International*, vol. 62, pp. 1958-1965, 2002.

Nigam, et al., "Toward an understanding of epithelial morphogenesis in health and disease", *Current.Opinion in Nephrology and Hypertension*, vol. 1, pp. 187-191, 1992.

Sakurai, et al., "Identification of pleiotrophin as a mesenchymal factor involved in ureteric bud branching morphogenesis", *Development*, vol. 128, pp. 3283-3293, 2001.

Piscone et al, Differentiation, 2002, vol. 70, pp. 227-246.

Current Protocols in Cell Biology, "Basic Techniques for Mammalian Cell Tissue Culture," contributed by M.C. Phelan, 1998, John Wiley & Sons, Inc, pp. 1.1.1-1.1.10.

Current Protocols in Cell Biology, "Overview of Extracellular Matrix," contributed by R.P. Mecham, 1998, John Wiley & Sons, Inc pp. 10.1.1-10.1.14.

METHODS OF INDUCING TUBULOGENESIS AND/OR BRANCHING MORPHOGENESIS OF KIDNEY CELL CULTURES

CROSS REFERENCE TO RELATED APPLICATIONS

The instant application claims priority as a divisional application of prior-filed U.S. patent application Ser. No. 10/608,783, filed Jun. 27, 2003 (now U.S. Pat. No. 7,326,570), which is a continuation-in-part of international application PCT/US2002/20673, filed Jun. 28, 2002, which claims priority to U.S. Provisional Ser. Application No. 60/301,684, filed Jun. 28, 2001. U.S. patent application Ser. No. 10/608,783 also claims priority to U.S. Provisional Application Ser. No. 60/426,152, filed Nov. 14, 2002. U.S. patent application Ser. No. 10/608,783 also claims priority as a continuation-in-part of each of U.S. patent application Ser. No. 09/595,195, filed Jun. 16, 2000 (now U.S. Pat. No. 7,074,552) and 09/965,651, filed Sep. 25, 2001 (now abandoned). Each of the prior-filed applications are incorporated herein by reference in their entirety.

FEDERAL SPONSORED RESEARCH

This work was supported by the National Institute of Diabetes and Digestive and Kidney Diseases through grant number RO1-DK53507, RO1-DK51211, the government has certain rights in the invention.

FIELD OF THE INVENTION

The invention generally concerns methods of tissue engineering, and more particularly relates to methods and compositions for kidney tissue generation and replacement.

BACKGROUND

End-stage renal disease (ESRD) affects almost 350,000 people living in the United States with an incidence that has increased by over 50% in the past decade. Total Medicare expenditures on patients with ESRD exceed $11.3 billion (U.S. Renal Data Service: 2001 Annual Data Report Atlas of End-Stage Renal Disease in the United States. Bethesda NIH, NIDDKD, 2001). The two currently treatment modalities for ESRD, dialysis and transplantation, both have significant limitations. Patients on dialysis have an extremely high mortality rate, approaching 20% per year. Patient survival is markedly improved with renal transplantation; however, the number of renal transplants is severely limited by the short supply of available organs and many patients die while awaiting transplantation of a kidney allograft.

Recently, several alternative modalities have been proposed. These include augmentation of traditional hemodialysis with a "renal assist device" consisting of xenoderived proximal tubule cells, xenotranplantation of whole developing kidney rudiments into adults, and the generation of histocompatible renal tissue using nuclear transplantation techniques.

SUMMARY

The invention provides a method of propagating ureteric bud cells in culture. The method includes culturing a UB in vitro under conditions that induce the UB to undergo branching morphogenesis to generate a population of UBs comprising tubular branches; subdividing the UB population; and resuspending each subpopulation in culture media.

The invention also provides a method for in vitro culturing and propagating ureteric bud tissue. The method includes isolating ureteric bud tissue from mesenchyme tissue obtained from embryonic kidney rudiments; culturing the isolated ureteric bud tissue in a biocompatible matrix in the presence of a culture medium comprising pleiotrophin and/or heregulin or an active fragment thereof for a sufficient time and under sufficient conditions to product tubular branches within the biocompatible matrix; separating the plurality of branch tips to generate bud fragments; and culturing each of the bud fragments in a biocompatible matrix with a culture medium comprising pleiotrophin and/or heregulin or an active fragment thereof.

The invention also provides a method for growing renal tubule cells in vitro, comprising culturing kidney cells in a growth medium comprising pleiotrophin and/or heregulin in an amount effective for achieving tubulogenesis.

The invention further provides a method for stimulating epithelial organogenesis, by contacting an epithelial tissue with an effective amount of a composition comprising one or more mesenchymally derived growth factor(s) secreted by mesenchymal tissue in culture; and culturing the epithelial tissue and the composition for a sufficient period of time and under conditions to allow the tissue and the composition to interact, wherein the composition stimulates epithelial organogenesis.

The invention also provides in vitro tissue generated by the foregoing method.

The invention includes a method of stimulating branching morphogenesis in an epithelial tissue comprising contacting the epithelial tissue with a composition comprising pleiotrophin and/or heregulin.

The invention also provides a method for in vitro tissue engineering of a functional mammalian epithelial tissue, organ or a fragment thereof by culturing and propagating embryonic epithelial explant, tissues, and/or cells by isolating the explant, tissue, and/or cells and growing the explant, tissue, and/or cells in a culture medium comprising pleiotrophin and/or heregulin, permitting the culture to form multiple branches, dissecting out individual tips of the branches; reculturing the branch tips in the culture medium comprising a heparin binding molecule (e.g., pleiotrophin and/or heregulin); combining the branch tips with embryonic or fetal mesenchymal tissue and/or cells, in the presence of the mixture of a culture medium in or on a biocompatible substrate; and culturing the combination in culture medium conditions suitable for tissue growth and tubulogenesis.

The invention further provides a method for stimulating branching morphogenesis in a kidney cell culture. The method includes contacting the kidney cell culture with an effective amount of a composition comprising one or more mesenchymally derived growth factor(s) secreted by a mesenchyme tissue in culture; and culturing the kidney cell culture and the composition for a sufficient period of time and under conditions to allow the cells and the composition to interact, wherein the composition stimulates branching tubular morphogenesis.

The invention also provides in vitro engineered kidney tissue. In one aspect of the invention the in vitro engineered kidney tissue is generated by the methods of the invention.

Also provided by the invention is a method of in vitro culturing and propagating metanephric mesenchyme tissue, comprising: isolating mesenchyme tissue at the time of induction; culturing the mesenchymal tissue in a composition comprising serum, nutrient rich medium, and mesenchymal and/or ureteric bud cell conditioned medium; and partitioning the cultured mesenchyme into multiple pieces and growing each piece separately in culture.

The invention provides a method for in vitro engineering and constructing a mammalian kidney. The method includes separating ureteric bud (UB) tissue from mesenchyme tissue obtained from an embryonic kidney rudiment; culturing the isolated ureteric bud tissue in a biocompatible matrix in the presence of a culture medium comprising pleiotrophin and/or heregulin or an active fragment thereof for a sufficient time and under sufficient conditions to produce tubular branches within the biocompatible matrix; separating the tubular branches to obtain a plurality of bud fragments; culturing each of the bud fragments in a biocompatible matrix with a culture medium comprising pleiotrophin and/or heregulin or an active fragment thereof to generate a plurality of tissues comprising tubular branches; combining the plurality of tissues comprising tubular branches with metanephric mesenchyme (MM) tissue in the presence of nutrient medium comprising pleiotrophin and/or heregulin; and culturing the UB and MM under conditions sufficient to cause the MM to differentiate and form nephron structures thereby forming a kidney.

The invention provides a functional mammalian kidney engineered and constructed in vitro, comprising: a ureteric bud (UB) tissue propagated in culture in the presence of a composition comprising pleiotrophin and/or heregulin to produce a functioning tubular structures; and a metanephric mesenchyme (MM) tissue propagated from cultured embryonic mesenchymal tissue fragments or cells to produce functioning nephrons wherein the ureteric bud tissue and the metanephric mesenchyme are co-cultured and wherein the ureteric bud tissue induces the metanephric mesenchyme to form nephrons, thereby forming a functional mammalian kidney.

The invention also provide a genetically engineered mammalian kidney produced by culturing a population of cells comprising ureteric bud (UB) cells in a biocompatible matrix in the presence of a culture medium comprising pleiotrophin and/or heregulin or an active fragment thereof for a sufficient time and under sufficient conditions to produce tubular branches within the biocompatible matrix, and wherein at least one ureteric bud cell of the population of cells is transfected with an exogenous polynucleotide such that the exogenous polynucleotide expresses a product; separating the tubular branches to obtain a plurality of bud fragments; culturing each of the bud fragments in a biocompatible matrix with a culture medium comprising pleiotrophin and/or heregulin or an active fragment thereof to generate a plurality of tissues comprising tubular branches; combining the plurality of tissues comprising tubular branches with metanephric mesenchyme (MM) tissue in the presence of nutrient medium comprising pleiotrophin and/or heregulin; and culturing the UB and MM under conditions sufficient to cause the MM to differentiate and form nephron structures thereby forming a kidney.

The invention provides a method of treating a subject suffering from kidney failure comprising transplanting a tissue-engineered kidney of the invention into a subject.

The invention also includes a method for treating acute renal failure (ARF) comprising administering to a subject suffering from ARF with a pharmaceutically effective amount of a composition comprising pleiotrophin and/or heregulin such that a symptom of ARF is ameliorated.

The invention also includes a renal tubule cell produced by culturing ureteric bud cells in a culture medium comprising pleiotrophin and/or heregulin in an amount effective for achieving tubulogenesis.

The details of one or more embodiments of the invention are set forth in the accompanying drawings and the description below. Other features, objects, and advantages of the invention will be apparent from the description and drawings, and from the claims.

PolyA sepharose beads adsorb pleiotrophin present in the fraction eluted from the Resource S cation exchange column. (C) Phase contrast photomicrographs of isolated ureteric buds grown for 7 days in morphogenetically active fraction eluted from the Resource S cation exchange column with or without exposure to polyA-sepharose beads. In either case, the fraction was supplemented with 10% FCS, 125 ng/ml GDNF and 250 ng/ml FGF1. Bar=500 μm.

Figure 5A:
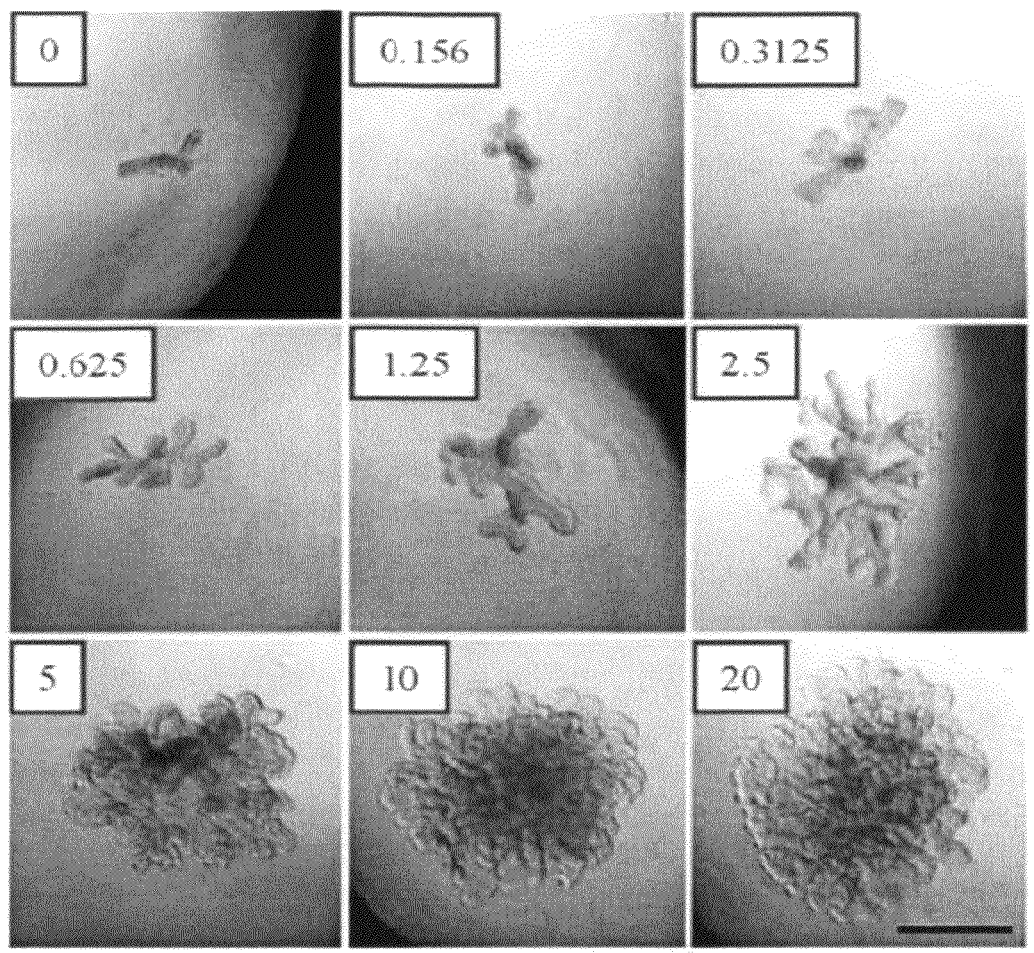

FIG. 5 indicates that pleiotrophin-mediated UB branching morphogenesis is concentration-dependent. (A) Phase contrast photomicrographs of isolated ureteric buds grown for seven days in DMEM/F12 supplemented with increasing concentration of purified pleiotrophin. In each case, the growth media was also supplemented with 10% FCS, 125 ng/ml GDNF and 250 ng/ml FGF1. The numbers in the upper-left-hand corner of each picture indicate the concentration of pleiotrophin in μg/ml. Clear differences in the phenotype depending on the concentration of pleiotrophin are exhibited. (B) Phase contrast photomicrographs of isolated ureteric buds grown for 11 days in the presence (1) or absence (2) of 250 ng/ml FGF1 diluted in DMEM/F12 supplemented with 2.5-5 μg/ml pleiotrophin, 10% FCS, and 125 ng/ml GDNF. Bar=500 μg/m.

FIG. 6 demonstrates pleiotrophin-induced UB tubulogenesis in vitro. (A) Bar graph demonstrating the morphogenetic effects of pleiotrophin on UBs grown in three-dimensional extracellular matrix gels. UBs were suspended in 20% Matrigel, 80% collagen gel mixture and grown for 4 days in the absence (control) or presence of purified pleiotrophin (0.1-2.5 μg/ml). Whole BSN-CM served as a positive control. All conditions were supplemented with 1% FCS. The percentage of cells and colonies with processes was counted as an indicator for tubulogenic activity. 20 cells/colony were counted in three randomly selected fields for each condition. Data is presented as mean±s.e.m., *$p<0.05$ (by unpaired Student's t test). (B) Phase contrast photomicrographs of UBs grown for 8 days in DMEM/F12 supplemented with 1% FCS (a) control and either BSN-CM (b) or purified pleiotrophin (c). BSN-CM and pleiotrophin induced the formation of branching tubules with lumens (compare b and c). Bar=50 μm.

FIG. 7 is an example of pleiotrophin expression in the embryonic kidney. (A) Immunoblot detection of pleiotrophin. Lane 1, extract of whole embryonic day 13 rat kidney; Lane 2, conditioned medium collected from UBs; Lane 3, conditioned medium from BSN cells. Whole kidney and BSN-CM were positive for pleiotrophin (arrow). (B) Embryonic day 13 mouse kidney frozen sections stained with anti-pleiotrophin antibody. Pleiotrophin localized at the basement membrane of developing UB (a). Normal goat IgG did not exhibit significant staining (b). Bar=100 μm.

Figure 8C:
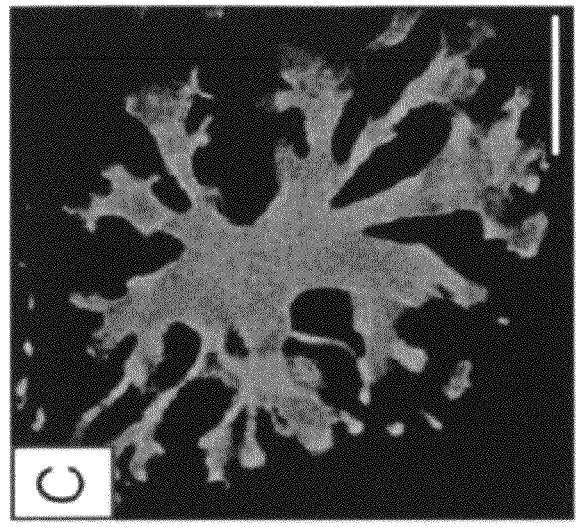
Figure 8B:
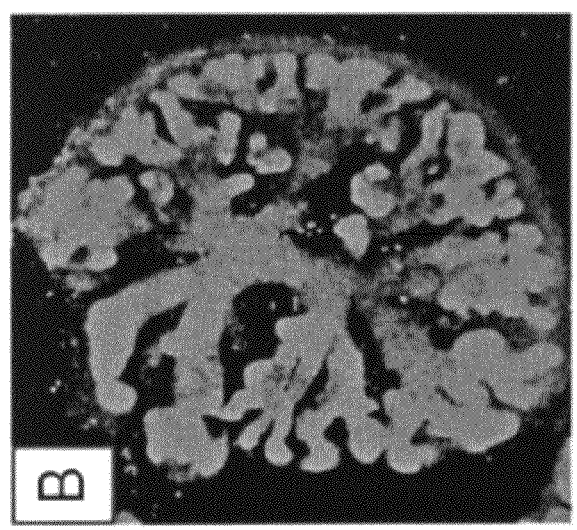
Figure 8A:
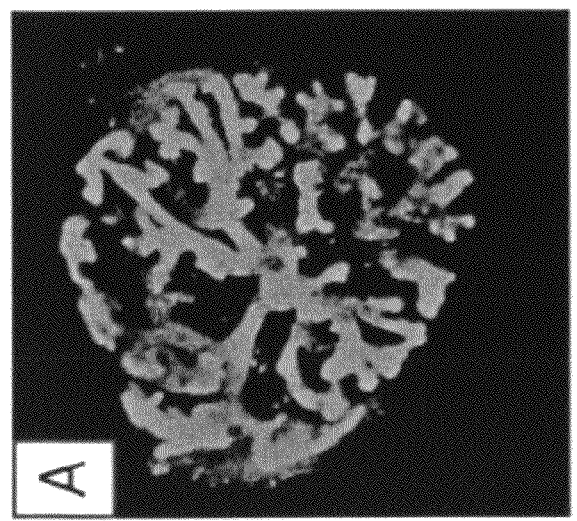

FIG. 8 shows the effect of exogenous pleiotrophin on UB morphology in whole kidney organ culture. Fluorescent photomicrographs of embryonic day 13 rat kidneys cultured for 7 days in DMEM/F12 supplemented with 10% FCS in the absence (a, control) or presence of pleiotrophin (b, 2.5 μg/ml; c, 5 μg/ml). The UB was visualized with FITC-conjugated lectin from Dolichos biflorus. Bar=500 μm.

Figure 9C:
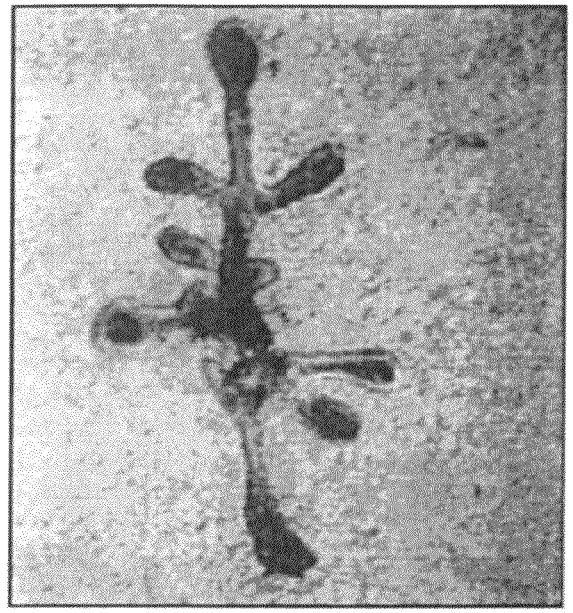
Figure 9B:
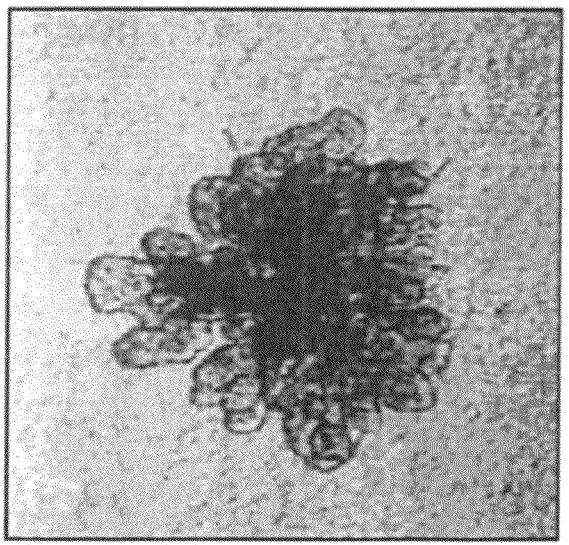
Figure 9A:

FIG. 9 shows Rat UBs that were isolated and suspended in extracellular matrix gels in the presence of: (A; control) GDNF+FGF-1; (B) heparin column eluate+GDNF+FGF-1; (C) whole BSN-CM+GDNF+FGF-1 for 7 days. BSN-CM was fractionated on a heparin affinity column.

Figure 10A:
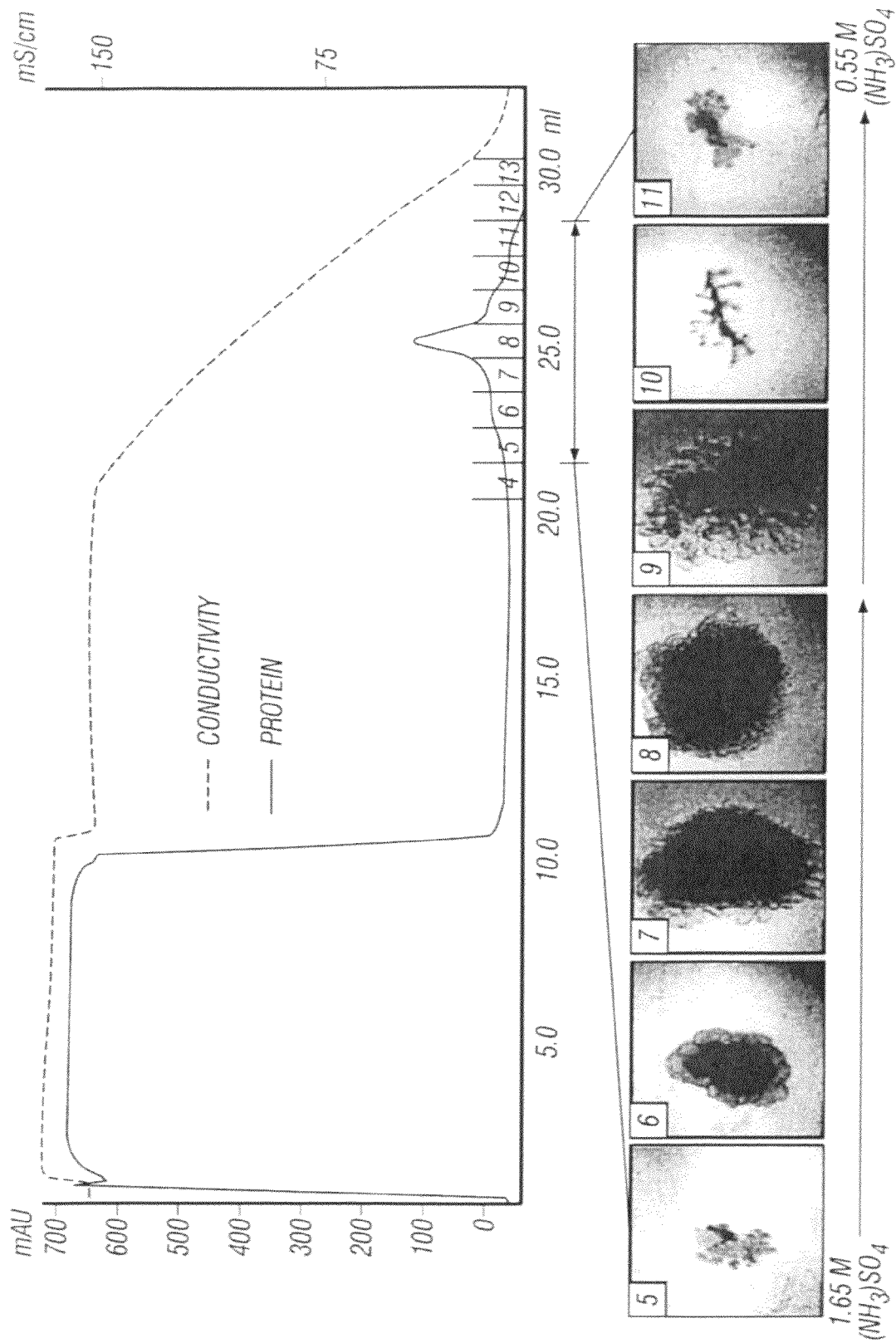
Figure 10B:
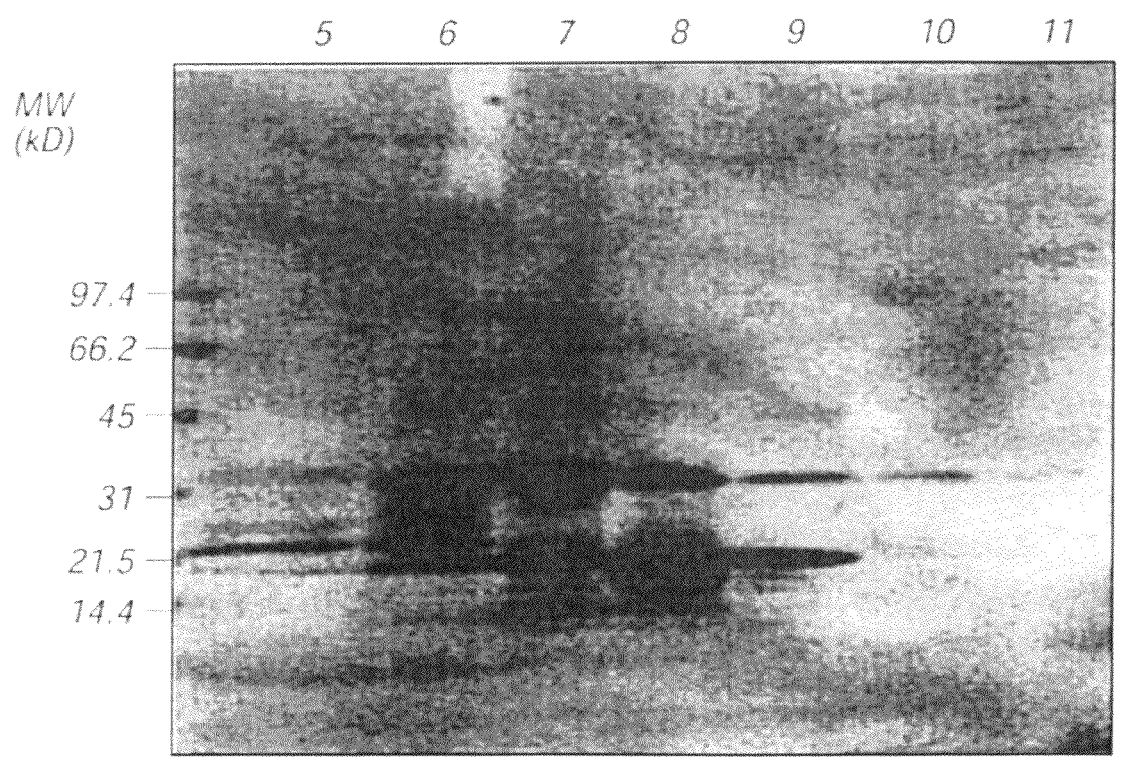

FIG. 10 shows the chromatographic separation profile of active heparin eluate from a hydrophobic interaction (Resource phenyl sepharose) column. Fractions 5-11 eluted with decreasing ammonium sulfate: gradient were subjected to isolated UB cultures, as well as SDS PAGE and silver staining.

Figure 11:
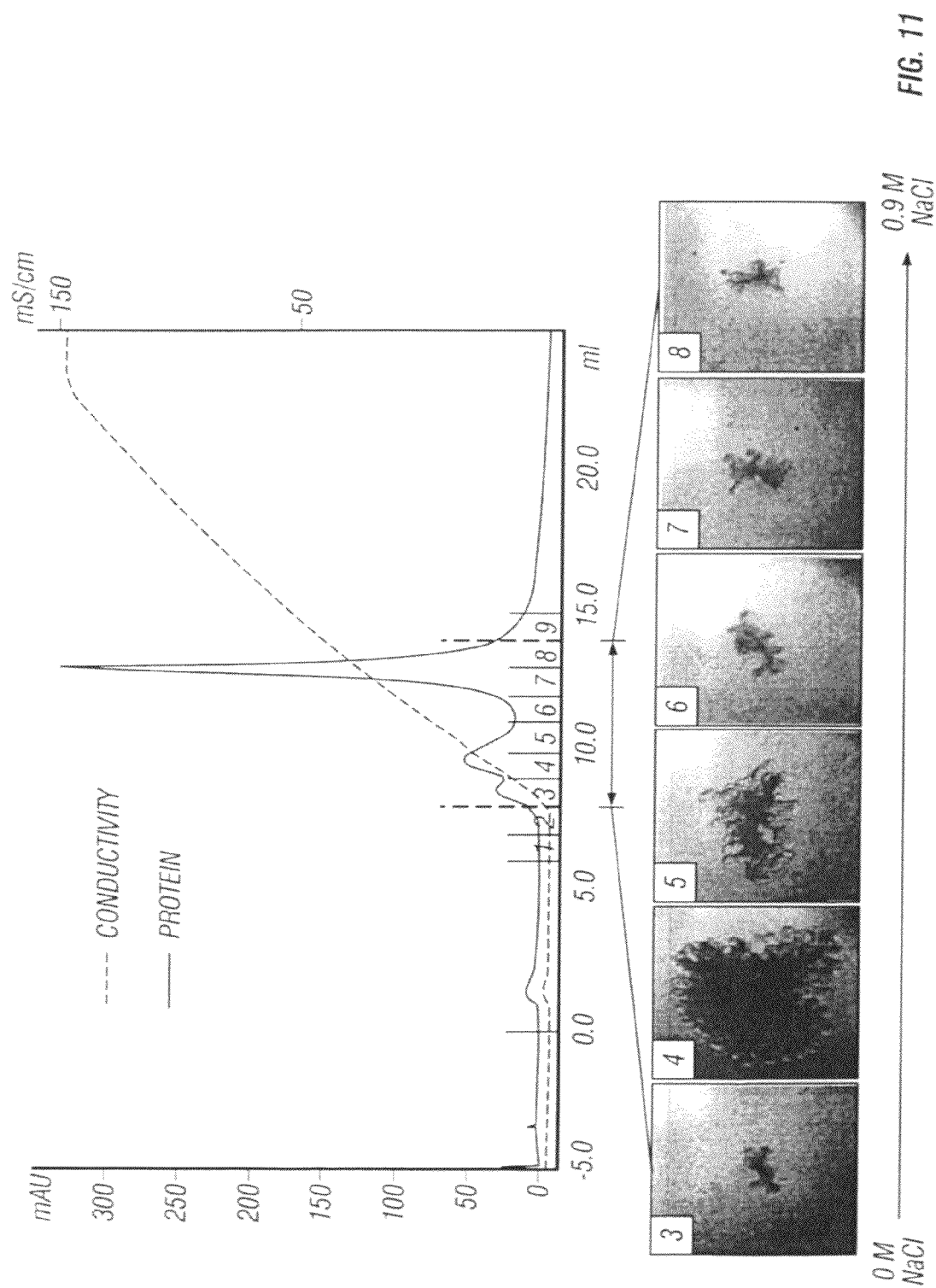

FIG. 11 depicts the chromatographic separation profile of active fractions from eluted from eluted from an anion exchange (Resource Q) column with increased salt gradient (upper). Fractions 3-8 were subjected to isolated UB culture assay. Activity is shown in the lower photographs.

Figure 12A:
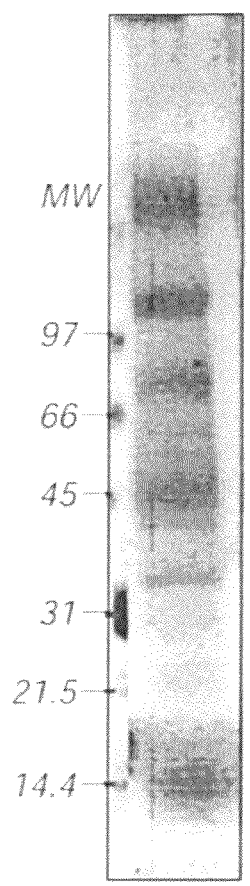
Figure 12B:
Figure 12C:
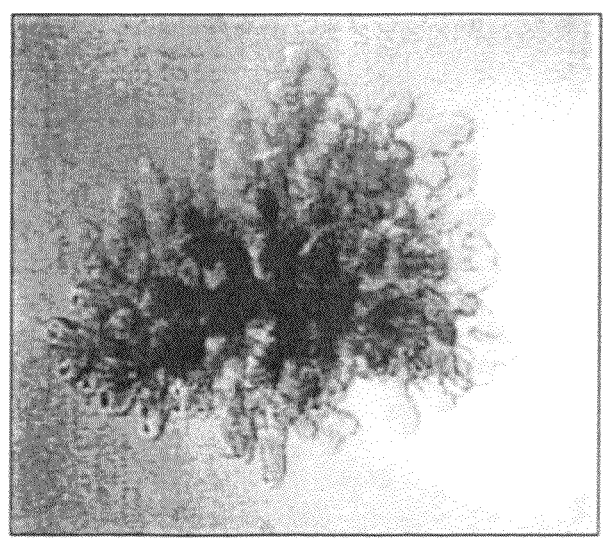

FIG. 12 shows that a non-pleiotrophin (PTN) fraction induced UB branching morphogenesis as well. (A) Fraction 4, obtained after three sequential column separations, contains several protein bands depicted by silver staining. (B) No PTN was detected by western blotting in this fraction. (C) Isolated UB cultured in the presence of fraction 4 with GDNF and FGF-1 for 8 days are shown.

Figure 13:
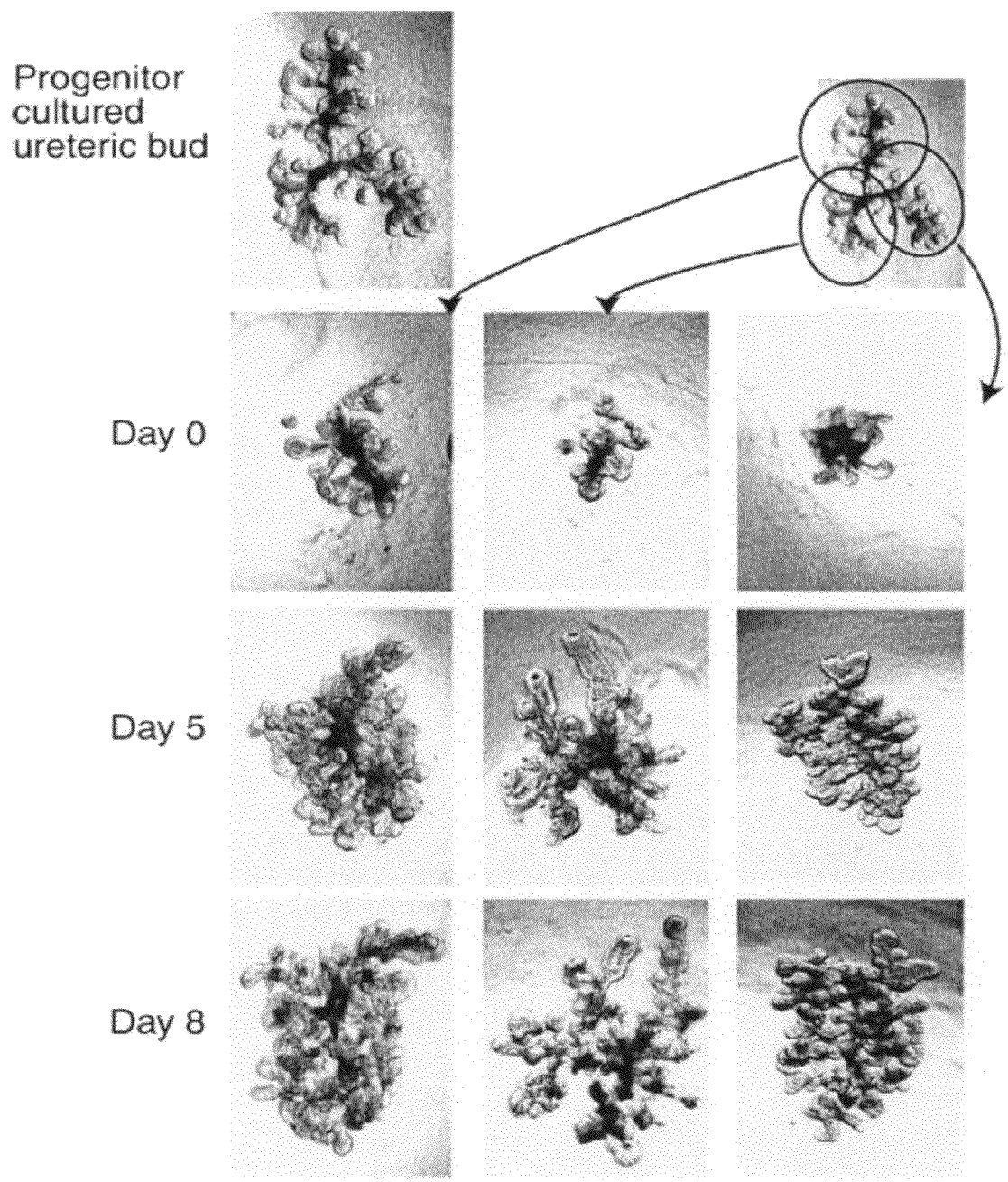

FIG. 13 shows growth an arborized structure from an isolated UB, which was subdivided into smaller fractions and induced into additional generations of UBs that grow and branch in vitro. Days 0, 5 and 8 shown.

Figure 14A:
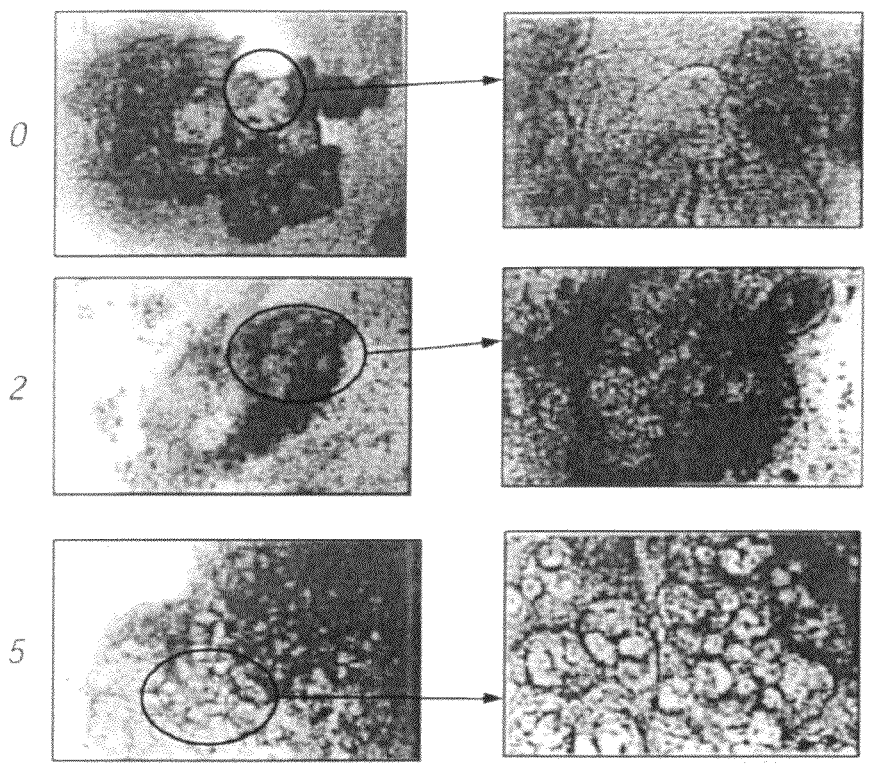
Figure 14B:
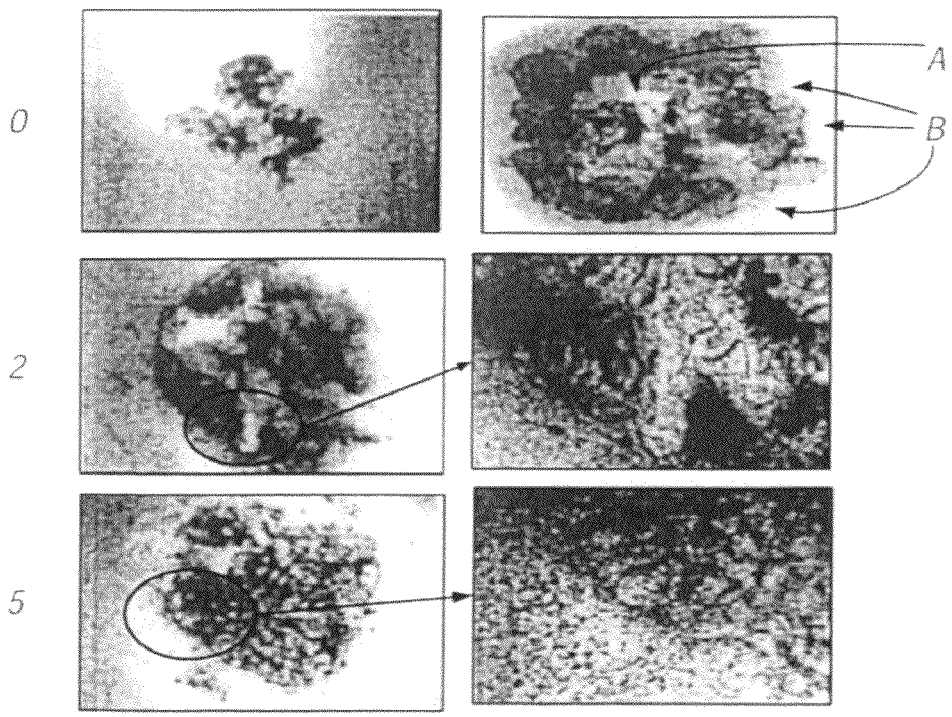

FIG. 14 shows UB generations that were recombined with freshly isolated metanephric mesenchyme, and they retained the ability to induce dramatic tubular epithelial differentiation of the mesenchyme. Days 0, 2 and 5 shown.

Figure 15:
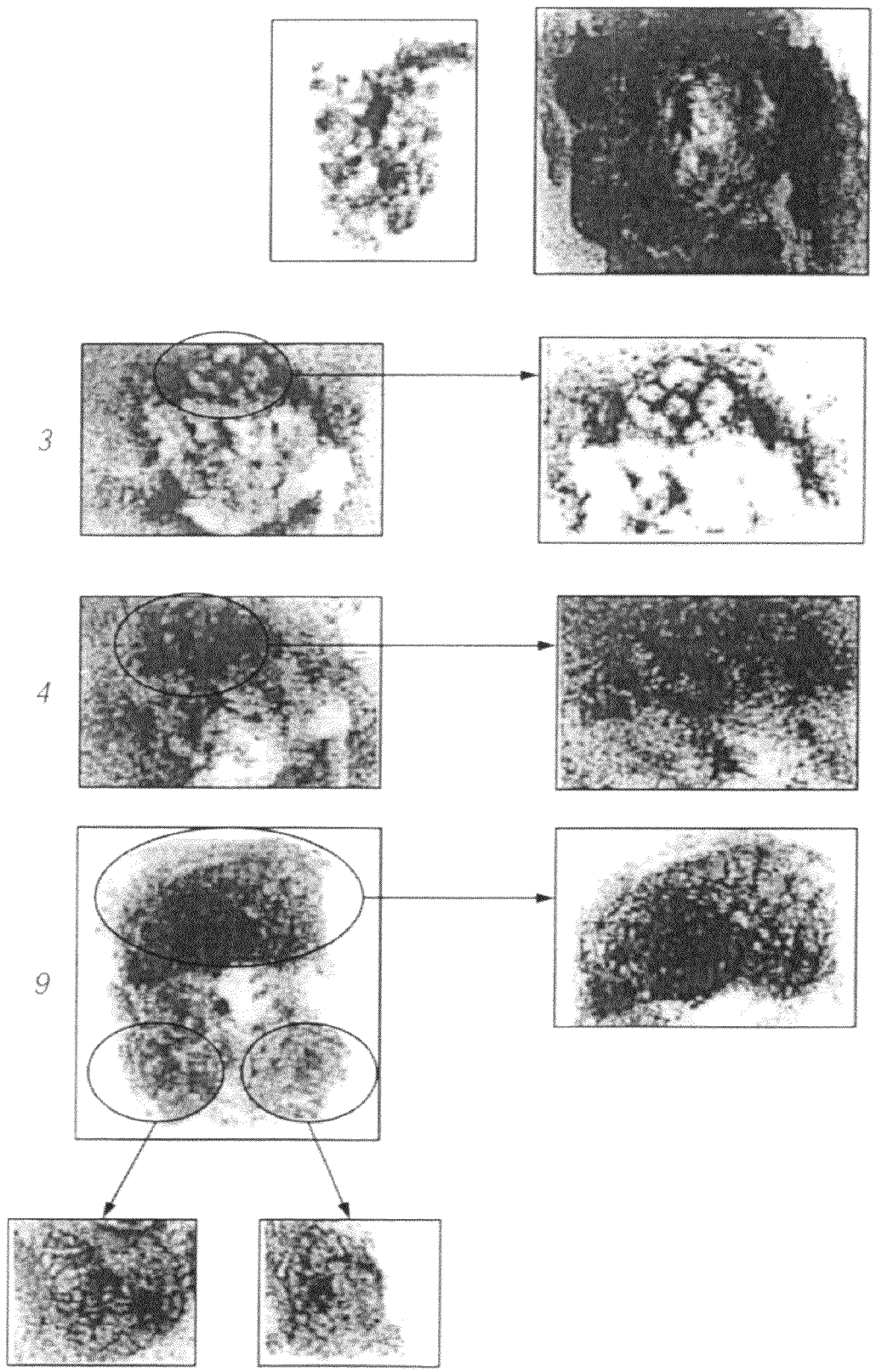

FIG. 15 shows additional evidence of the ability to induce dramatic tubular epithelial differentiation of the mesenchyme. Days 3, 4 and 9 are shown.

Figure 16:
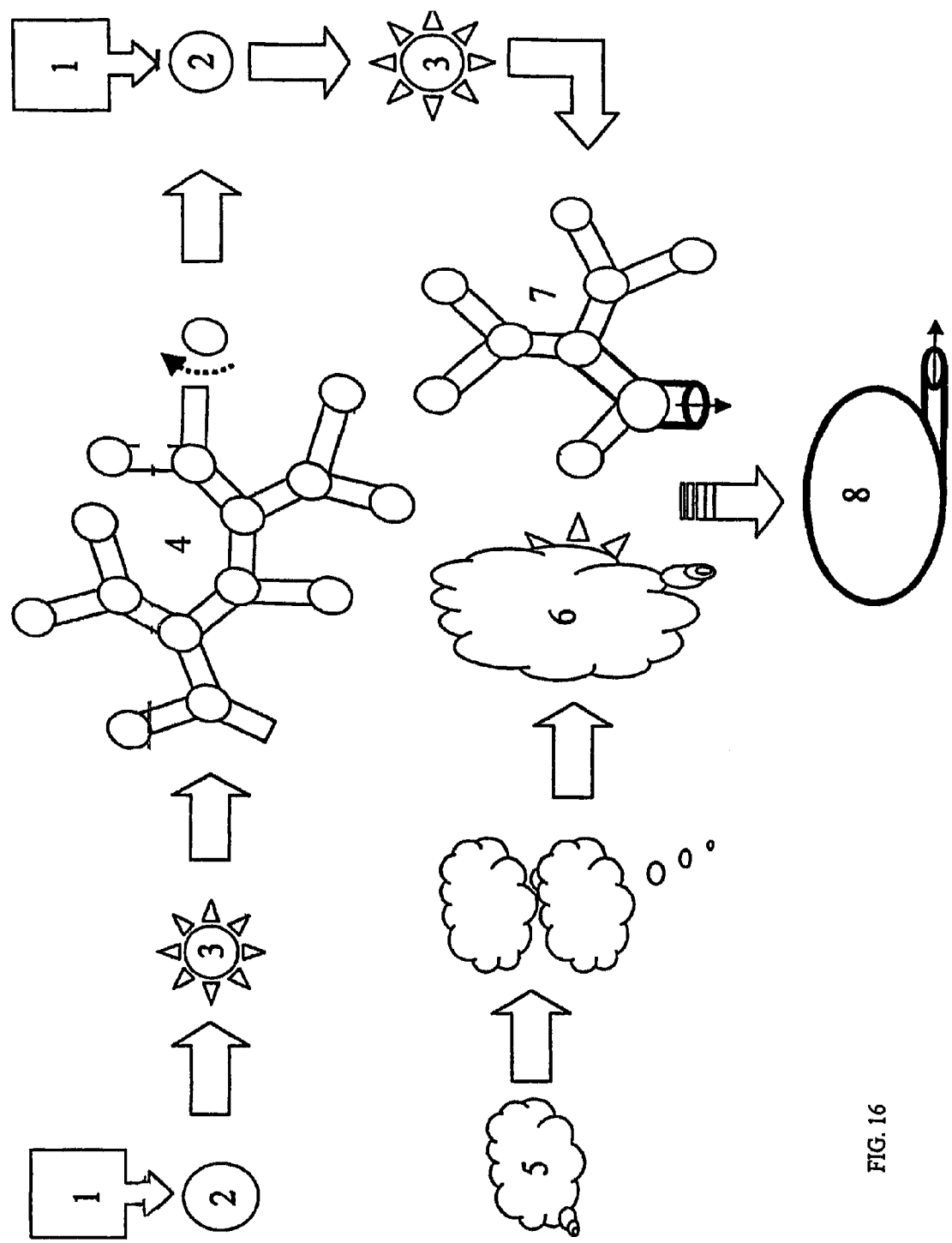

FIG. 16: A schematic representation of the methodology and salient points of this invention. A schematic diagram showing a novel culture method for inducing in vitro branching morphogenesis of an isolated ureteric bud (UB), simultaneous culture of mesenchymal tissue and recombination and coculturing of the two cultured tissue fragments. The mesenchymal tissue added to the bud culture induces the bud to directionally extend branching tubules and further differentiate and incorporate to form a functioning nephron, capable of absorbing, filtering, collecting and secreting body fluids. Schematically depicted is a ureteric bud fragment in culture 2, being inducing by a stimulant(s) to produce a pluripotent fragment 3, that is capable of branching morphogenesis to form a branched three-dimensional structure 4. It can be see that an excised growing tip 2 can be further cultured in the presence of an inducer(s) 1 to again form an activated fragment 3 that will continue its tubulogenic morphogenesis. Simultaneously, an isolated fragment of mesenchymal tissue 5 is grown in culture to produce multiple pieces of mesenchymal tissue. One such piece 6 is grown and is then placed in co-culture with an actively branching bud fragment 7. The bud fragment, under influence of the mesenchymal induction continues to branch in a now directed fashion and to further differentiate to form maturing effluent collecting tubules, enlarging as the branching progresses to accommodate increased effluent and incorporating into new nephrons. Eventually an embryonic kidney, or a functionally equivalent fragment thereof, is formed 8.

Figure 17:
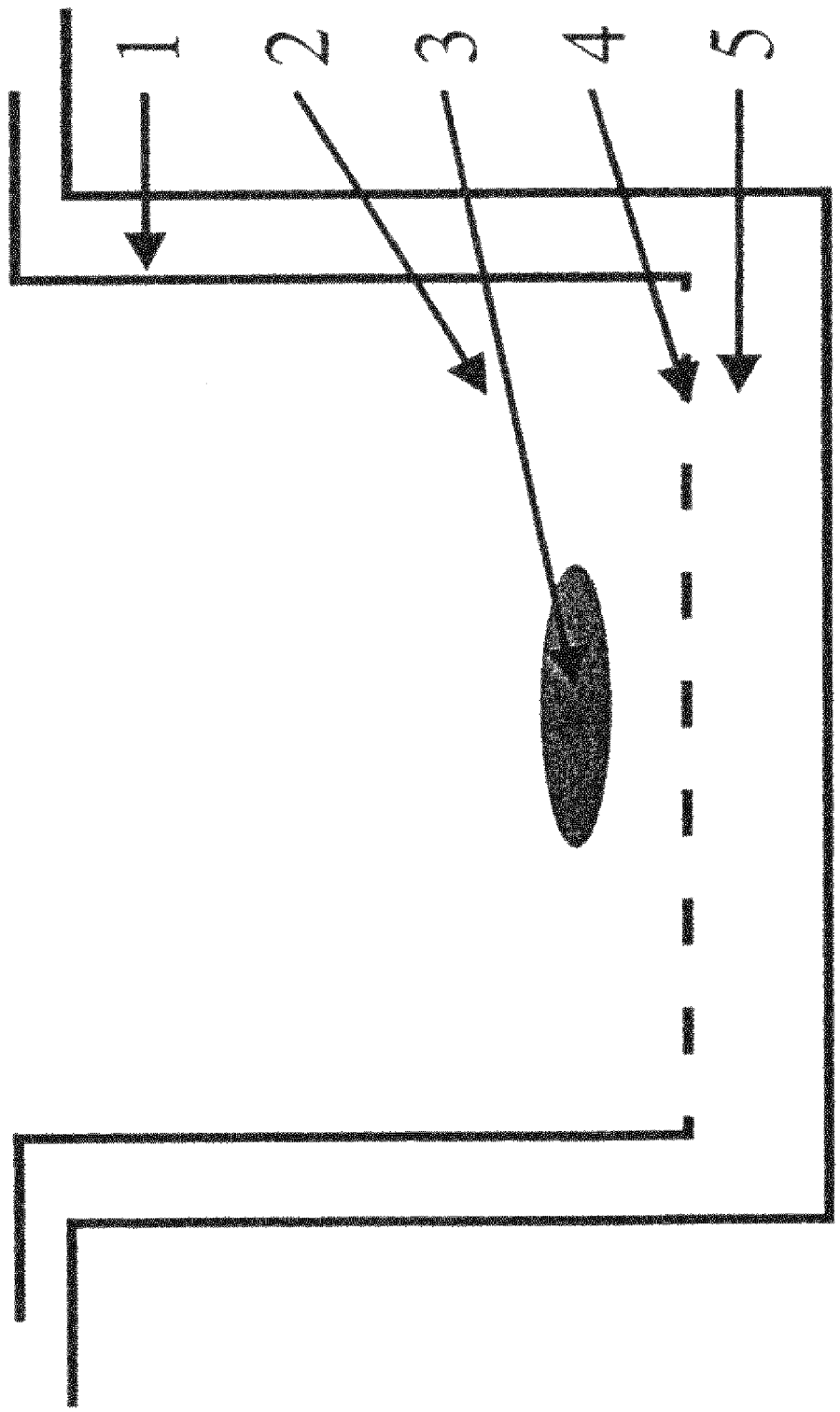
Figure 18:
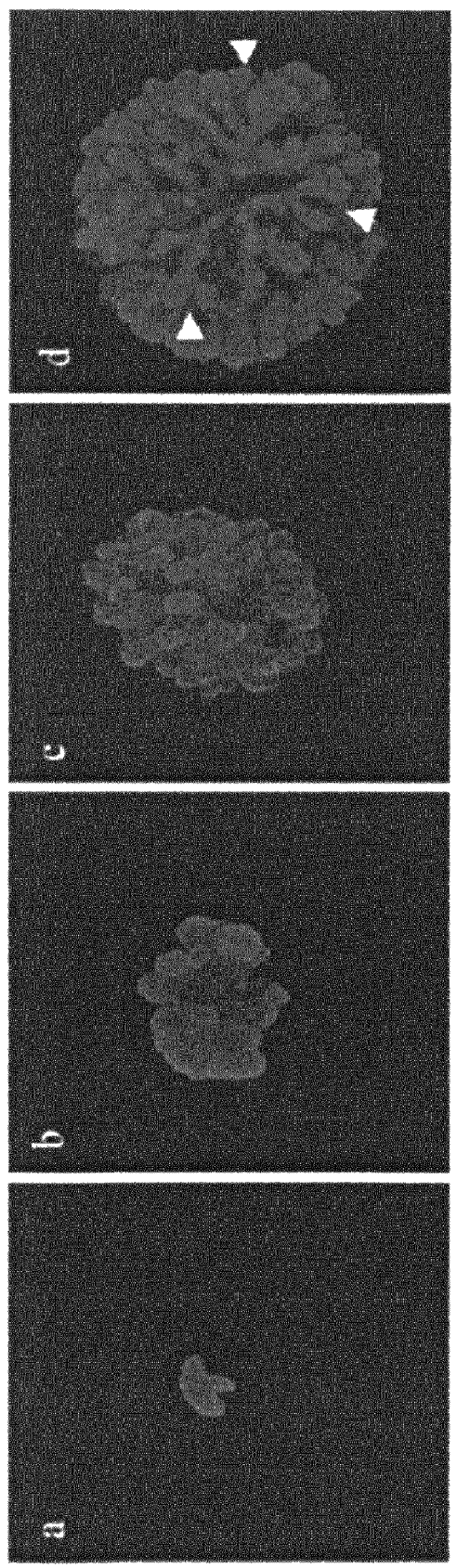
Figure 19:
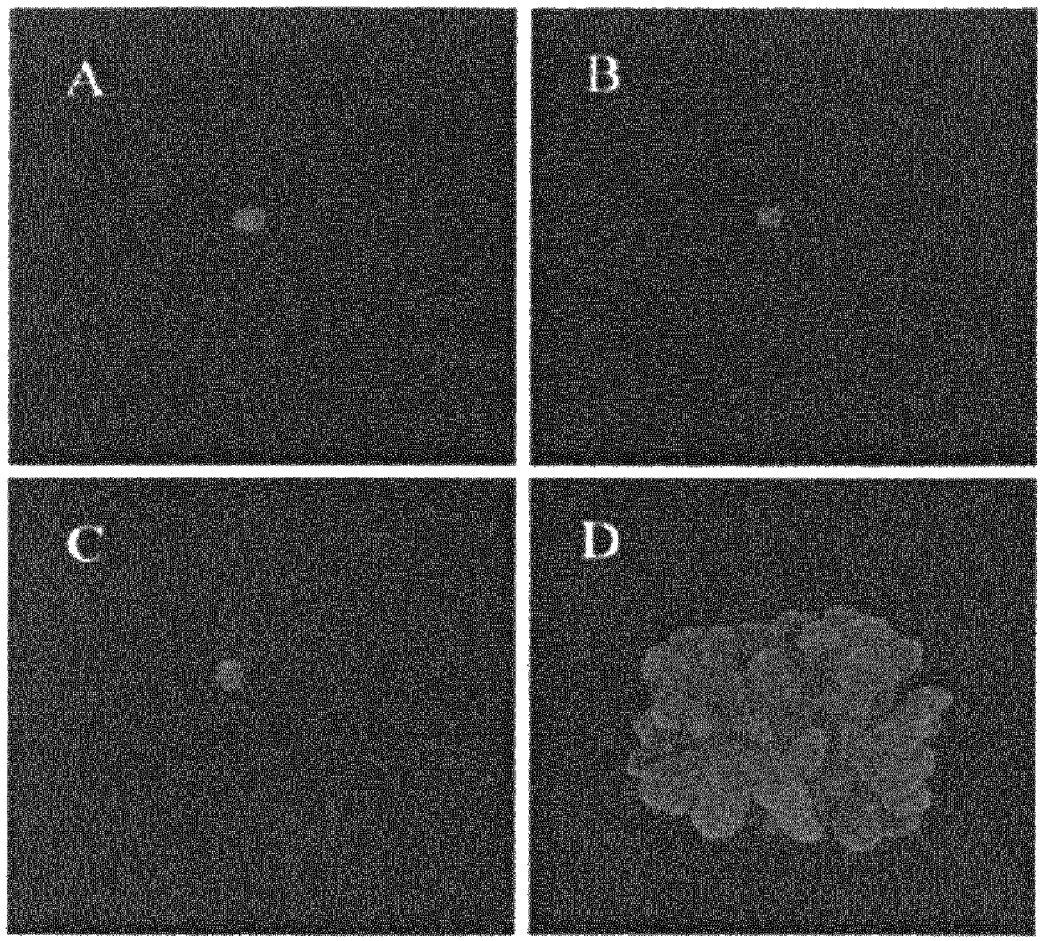
Figure 20:
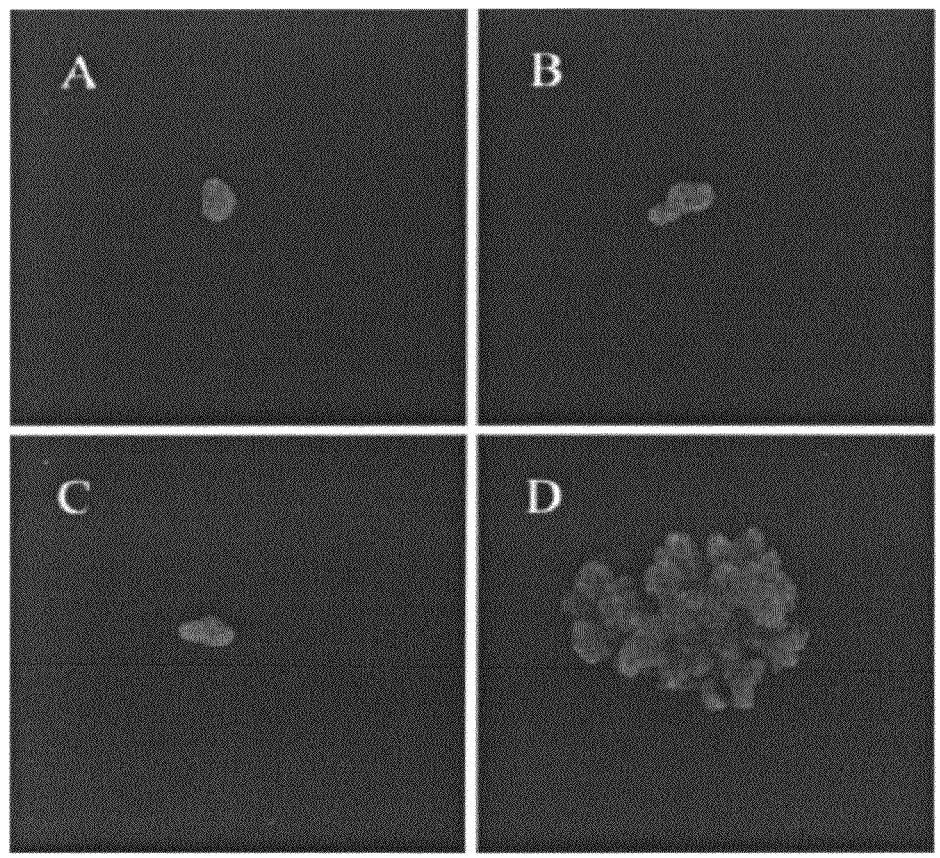
Figure 21:
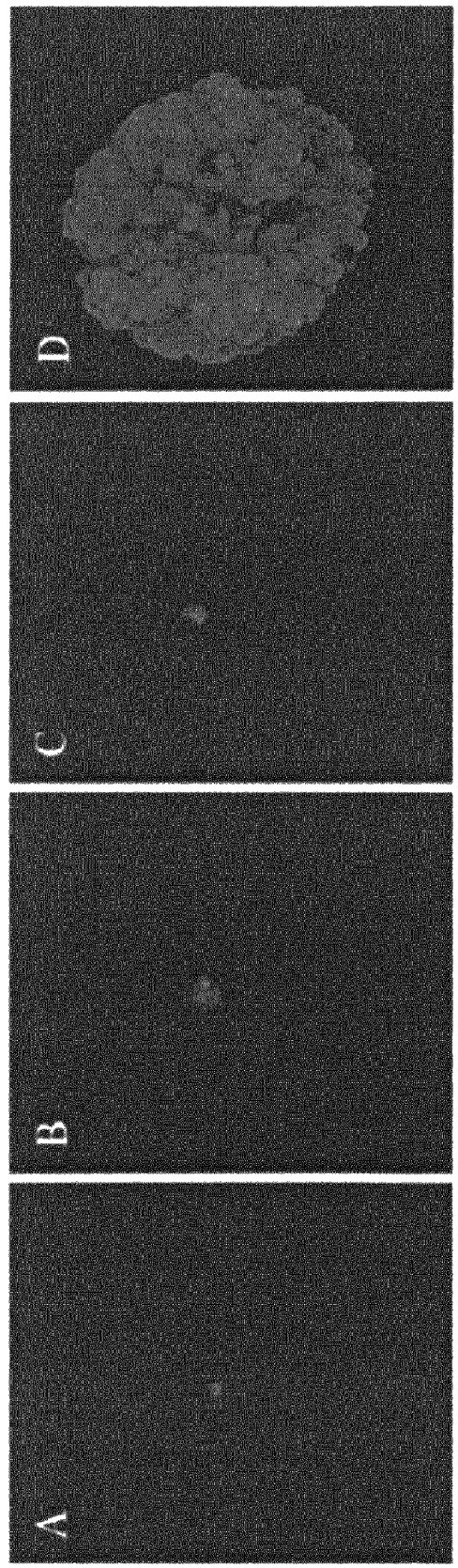

FIG. 17: A novel culture system for in vitro branching morphogenesis of the ureteric bud (UB) UBs free from mesenchyme were micro-dissected from E-13 rat kidney rudiments and placed in an ECM gel suspension composed of type I collagen and growth factor-reduced Matrigel®, and cultured in BSN cell-conditioned medium (BSN-CM) supplemented with 10% FCS and growth factors. Details are given elsewhere in the text. The cultured UB was monitored daily by microscopy.

FIGS. 18A-D: The UB undergoes branching morphogenesis in vitro and develops three-dimensional tubular structures in the absence of mesenchyme E-13 rat UB was isolated and cultured as described herein below. After culture, UBs were fixed at different time points and processed for DB lectin staining. 3-D reconstructions of confocal images are shown: a) A freshly isolated UB form an E-13 rat embryonic kidney with a single branched tubular structure; b) The very same UB shown in a) after being cultured for 3 days. The tissue has proliferated and small protrusions have formed; c) Again, the same UB as shown in a) cultured for 6 days. More protrusions have formed, and the protrusions have started to elongate and branch dichotomously; d) the same UB as shown in a) cultured for 12 days. The protrusions have undergone further elongation and repeated dichotomous branching to form a structure resembling the developing collecting system of a kidney. The white arrows indicate branch points. At higher power, the structures formed in this in vitro culture system exhibited lumens. Phase microscopic examination and staining for markers revealed no evidence for contamination by other tissue or cells.

FIGS. 19A-D: BSN-CM and at least one soluble growth factor are required for branching morphogenesis of the isolated UB A: The UB cultured in the absence of BSN-CM and growth factors; B: The UB cultured with the mixture of growth factors (including EGF, IGF, HGF, FGF-2, and GDNF) but no BSN-CM; C: The UB cultured in the presence of BSN-CM alone; D: The UB cultured in the presence of both BSN-CM and the mixture of growth factors. All cultures were carried out for about one week and then processed for DB lectin staining. Shown is the three-dimensional reconstruction of confocal images. The isolated UB exhibits branching morphogenesis only in the presence of both BSN-CM and the mixture of growth factors.

Figure 22:
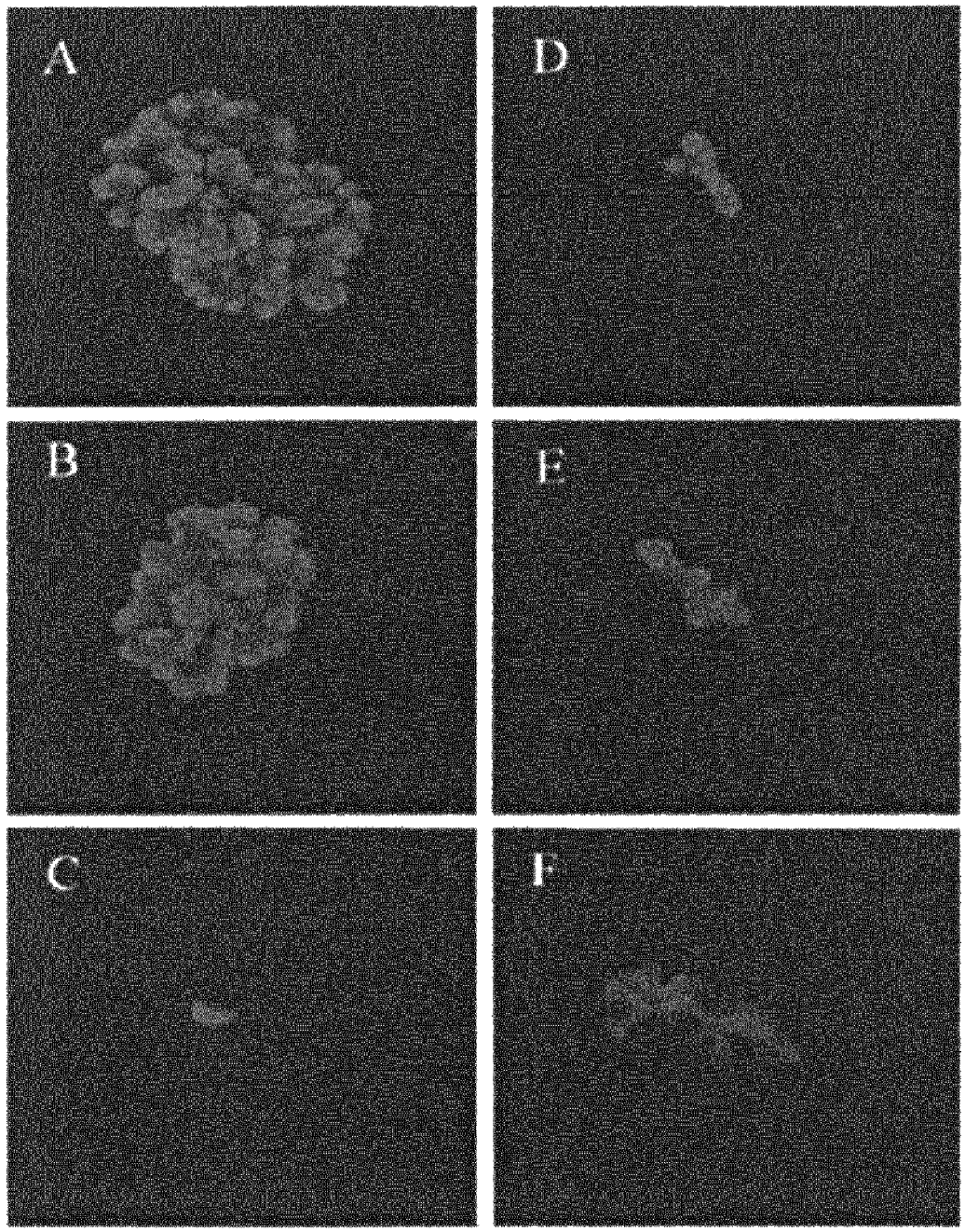
Figure 23:
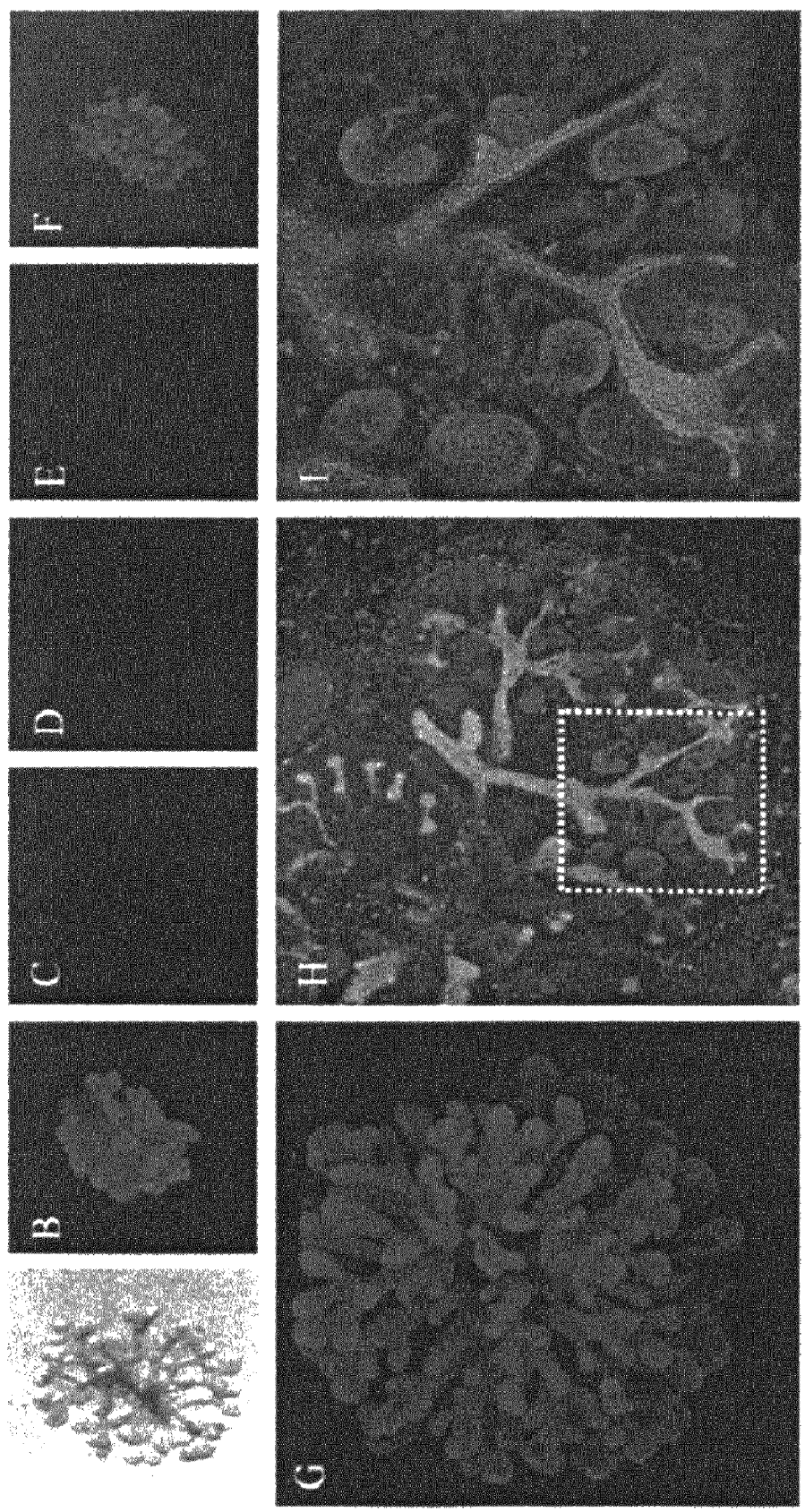

FIGS. 20A-D: BSN-CM contains unique soluble factor(s) for branching morphogenesis of the isolated UB. The UBs were cultured in the presence of the key growth factor (GDNF; see FIG. 22) but with different cell conditioned media: A: 3T3 fibroblast cell conditioned medium; B: immortalized UB cell conditioned medium; C: mIMCD cell conditioned medium; D: BSN cell conditioned medium. After culture, the UBs were fixed and processed for DB lectin staining. Only BSN-CM could promote extensive branching morphogenesis of the isolated UB.

FIGS. 21A-D: GDNF plus BSN-CM is required for branching morphogenesis. The UBs were cultured in the presence of BSN-CM, as in FIG. 19 but with each of single growth factors present in the growth factor mixture. Several examples are shown: A: with EGF alone; B: with FGF-2 alone; C: with HGF alone; D: with GDNF alone. Only GDNF combined with BSN-CM could promote branching morphogenesis of the isolated UB.

FIGS. 22A-F: GDNF is required for both early and late branching morphogenesis in vitro! A-C: The antibodies against GDNF are neutralizing antibodies. A: UB was cultured in the presence of BSN-CM and GDNF without antibodies; B: same as A, but normal goat IgG antibody were added; C: same as A, but antibodies against GDNF were added. D-F: GDNF is required for branching morphogenesis. The UBs were initially cultured in the presence of BSN-CM and GDNF and then the cultures were washed to remove GDNF at different time points; the UBs were then continuously cultured in BSN-CM without GDNF. To ensure neutralization of residual GDNF in the culture, antibodies against GDNF were added after removal and washing of GDNF from the culture medium. D: The UB was cultured as in A, but GDNF was removed and antibodies against GDNF were added on the first day of culture; E: Same as D, but the GDNF was removed and antibodies against GDNF were added on the second day of culture; F: Same as D, but the GDNF was removed and antibodies against GDNF were added on the third day of culture (compare with structures in FIG. 18). All cultures were carried out until the fifth day and processed with DB lectin staining. Whenever GDNF is depleted, UB growth and branching morphogenesis is aborted, indicating that GDNF is required for both early and late branching morphogenesis in vitro.

FIGS. 23A-I: The cultured three-dimensional tubular structure exhibits markers of UB epithelium and is functionally capable of inducing nephrogenesis when recombined with metanephric mesenchyme in vitro. The UBs were cultured in the presence of BSN-CM and GDNF and then stained for various markers (A-F). A: Light microscopic phase photograph of cultured UB; B: Staining with DB lectin, a ureteric bud specific lectin which binds to the UB and its derivatives; C: Staining for vimentin, a mesenchymal marker, D: Staining for N-CAM, the early marker for mesenchymal to epithelial conversion in the kidney, E: Staining with PNA lectin, a mesenchymally derived renal epithelial cell marker, F: Staining for cytokeratin, an epithelial marker. G-I: The cultured three-dimensional tubular structure is capable of inducing nephrogenesis when recombined with metanephric mesenchyme. The isolated UB was first cultured 7-10 days as shown in G. Then, the cultured UB was removed from the ECM gel and recombined with freshly isolated metanephric mesenchyme from E13 rat kidneys. The recombinant was cultured on a Transwell filter for another 5 days. After culture, the sample was double stained with DB lectin (FITC) and PNA lectin (TRITC) as shown in H and in the enlarged section of H shown in I. Results indicated that the in vitro cultured UB derived structures are capable of inducing nephrogenesis in vitro.

Figure 24:
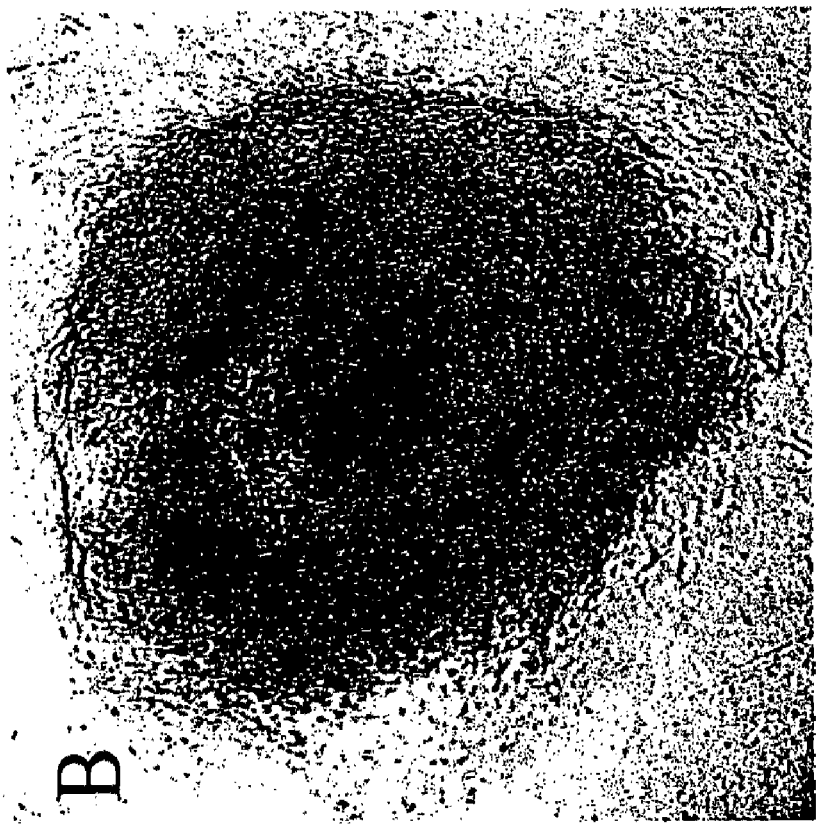
Figure 24:
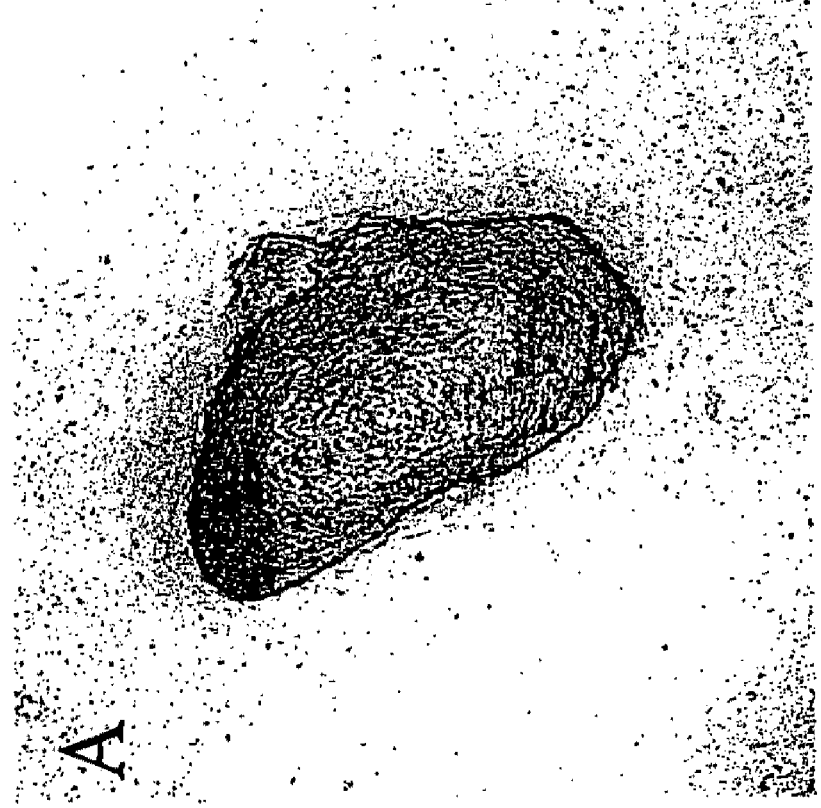
Figure 25:

FIGS. 24A-B: Culture of metanephric mesenchyme. Day 13 embryonic rat kidneys rudiments were microdissected to separate the ureteric bud from the metanephric mesenchyme. The metanephric mesenchyme was then placed in a transwell tissue culture insert on top of the polycarbonate filter (3.mu.m pore size). Media (DME/F12) supplemented with 10% fetal calf serum (FCS) was placed in the bottom of the chamber and the entire setup was incubated at 37.degree. C. with 5% $CO_2$ with 100% humidity. (A) Freshly isolated metanephric mesenchyme. (B) The same metanephric mesenchyme following 5 days in culture.

FIGS. 25A-D: Subculture of the ureteric bud. Ureteric buds were isolated from E13 rat kidneys and grown in culture for 7 days. At the end of this culture period the ureteric bud was dissected free of the surrounding extracellular matrix and the bud was cut into pieces and subcultured under the same conditions. (A) Originally isolated ureteric bud after seven days of culture. Black box indicates piece of bud that was dissected free and subcultured. (B) Subcultured bud after 24 hrs in culture. (C) Subcultured bud after 4 days in culture. (D) Subcultured bud after 7 days in culture.

Figure 26:
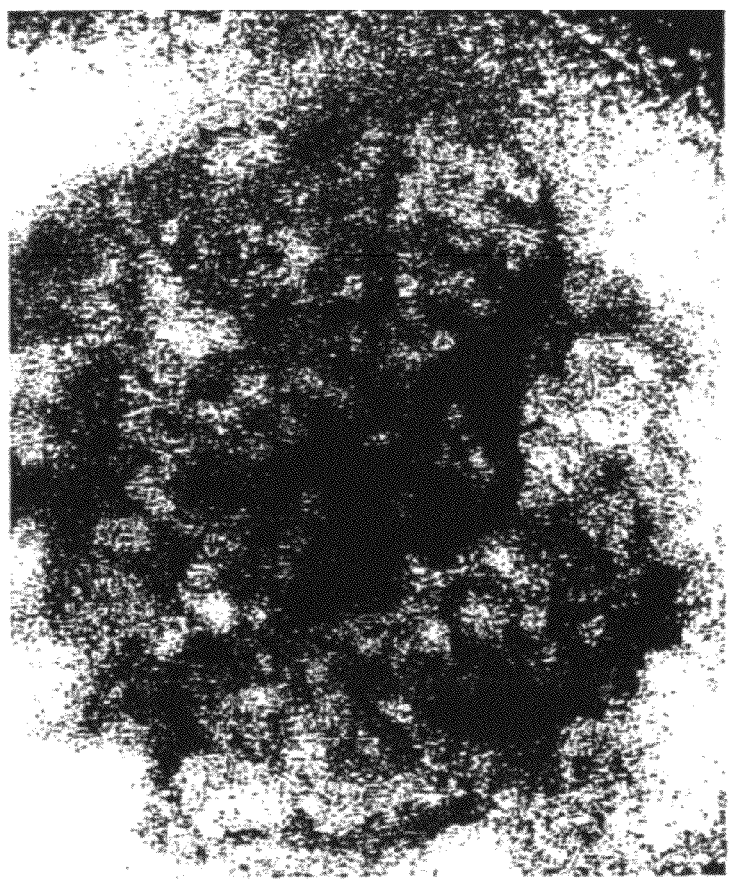

FIG. 26: Recombination of subcultured bud with freshly isolated metanephric mesenchyme. Ureteric buds were isolated, cultured and subcultured as previously described in FIG. 25. Metanephric mesenchymes were microdissected from E13 day rat embryonic kidneys and placed in close contact with subcultured ureteric bud as in FIG. 23. The recombined tissues were grown in culture for 7 days. Tubular structures are evident at this time.

Like reference symbols in the various drawings indicate like elements.

DETAILED DESCRIPTION

Many epithelial organs such as kidney, lung, and prostate under go branching morphogenesis in the course of development. The kidney is formed by mutual induction between two tissue derived from the intermediate mesoderm, the metanephric mesenchyme (MM), and the ureteric bud (UB). The UB induces the MM to differentiate and form the proximal nephron, while the UB undergoes dichotomous branching and elongation as it invades the MM, ultimately forming the kidney collecting system.

Soluble factors that have been thought to play a role in morphogenetic capacity include hepatocytes growth factor (HGF) and epidermal growth factor (EGF) receptor ligands, which have been shown to induce branching tubular structures in epithelial cells cultured in collagen gels. However, these studies have been largely carried out on adult cell lines. In a cell culture model that employs a UB cell line, derived from embryonic day 11.5 (E 11.5) mouse, neither HGF, EGF receptor ligands, nor many other factors tested (alone or in combination), were able to induce UBs to form branching tubular structures with lumens.

As used herein, the abbreviation UB includes ureteric bud cells obtained from UB tissue, as well as UB tissue fragments, whole UB tissue, and UB cell lines, unless clearly indicated otherwise in the specification. The UB cells may be primary cells obtained from embryonic kidney tissue by various techniques known in the art. Such primary UB cells are not immortalized (e.g., by SV40), but may be transfected and/or transformed to express a desired product, as discussed in more detail herein.

Accordingly, the identification of specific soluble factors (e.g., MM-derived soluble factors) mediating UB branching morphogenesis remains a central question in this field. Hepatocyte growth factor (HGF) has been shown to induce the formation of branching tubular structures with lumens in three-dimensional cultures of epithelial cell lines derived from adult kidneys (i.e., MDCK and mIMCD cells) (Barros et al., 1995; Cantley et al., 1994; Montesano et al., 1991; Santos et al., 1993). However, incubation of three-dimensional cultures of an embryonic cell line derived from the ureteric bud (UB) with HGF had only a slight morphogenetic effect and the formation of branching tubular structures with lumens was not observed (Sakurai et al., 1997a). Furthermore, HGF, alone or in the presence of GDNF, does not induce branching morphogenesis of the isolated UB. This suggests that HGF is not an essential factor for early branching morphogenesis of the embryonic UB, though it may play a facilitory role. This notion is supported by the fact that genetic deletion of hgf or its receptor (c-met) apparently has little if any effect on kidney development (Bladt et al., 1995; Schmidt et al., 1995).

Another group of soluble factors implicated in branching morphogenesis of epithelial cells are the family of epidermal growth factor (EGF) receptor ligands. EGF receptor ligands are capable of inducing the formation of branching tubular structures with lumens in three-dimensional cultures of mIMCD cells, a kidney cell line derived from adult collecting duct cells (Barros et al., 1995; Sakurai et al., 1997b). However, as is the case with HGF, EGF receptor ligands are not capable of inducing the formation of branching tubular structures in three-dimensional cultures of the embryonically-derived UB cells (Sakurai et al., 1997a), nor are they capable of inducing branching morphogenesis of the isolated UB (Qiao et al., 1999a). Deletion of the EGF receptor gene results in cystic dilation of collecting ducts in mice with certain genetic backgrounds, perhaps suggesting a role in final maturation of these structures (Threadgill et al., 1995). However, as with HGF, most experimental evidence indicates that the EGF receptor ligands are not essential for early steps in UB branching morphogenesis.

In fact, among many growth factors hypothesized to play a role in kidney development, no single factor, or combination of factors, has been shown to induce UBs to form branching tubular structures (undergo tubulogenesis). Tubulogenesis is a phenotypic transformation of the cells such that condensed aggregates of tubule cells form about a central lumen wherein said lumen is bordered by cells possessing a polarized epithelial phenotype and tight junctional complexes along the lumenal border. Conditioned medium elaborated by the MM-derived cell line, BSN-CM, consistently induced UBs in three-dimensional culture to form branching tubular structures with clearly distinguishable lumens. Likewise, in the isolated UB culture system (in the presence of GDNF), no growth factor, alone or in combination, could induce the extensive branching morphogenesis observed when the isolated UB was cultured with BSN-CM, as demonstrated by the invention.

An essential role for GDNF in UB development is supported by a number of studies, including gene knockouts. For example, null mutations of gdnf its receptor, c-ret, or its co-receptor, gfra, result in abnormal kidney development, although variable phenotypes have been reported in the gdnf and c-ret knockout mice (Enomoto et al., 1998; Moore et al., 1996; Schuchardt et al., 1996). Moreover, although the proliferative effect of GDNF on UBs has been debated (Pepicelli et al., 1997; Sainio et al., 1997), GDNF has been shown to initiate UB growth (Sainio et al., 1997), and plays a role in branching morphogenesis of the isolated UB. Nevertheless, GDNF is not alone sufficient to induce branching morphogenesis of either the isolated UB or cultured UBs (Salcurai et al., 1997a), again consistent with the view that there are additional factors which are critical to the branching morphogenesis of the UB.

Studies in the developing mammalian lung and Drosophila trachea indicate that members of the FGF family function in branching morphogenesis of epithelial tissues (Hogan, 1999; Metzger and Krasnow, 1999; Zelzer and Shilo, 2000). Furthermore, null mutations of either fgf7 or fgf10 have also been reported to affect kidney development (Ohuchi et al., 2000; Qiao et al., 1999b), although in both cases the kidneys appear to be modestly affected. For example, fgf7-null kidneys, there is a 30% reduction in the number of nephrons, and the kidneys appear to function normally (Qiao et al., 1999b). Moreover, since FGF7 is detected in the developing kidney only after several iterations of UB branching have already occurred, it is likely that other factors are necessary for the early steps of the branching program. In the case of FGF 10, the defect appears similar, although the phenotype has yet to be investigated in detail since the embryos die at birth due to severe lung defects (Ohuchi et al., 2000). Nevertheless, by potentiating the effect of an essential branching morphogen produced by the MM, certain FGFs may play a facilitory role in early UB branching morphogenesis (see below).

The invention demonstrates that UBs undergo branching tubulogenesis in the presence of a conditioned medium elaborated by a cell line derived from the MM also isolated from an E11.5 mouse (BSN cells). This suggests that other soluble factors present in BSN-CM are important for UB morphogenesis. These novel factors that are secreted by the MM are important for the development of the collecting system in artificial systems as well as in vivo.

This MM-derived cell conditioned medium (BSN-CM), when supplemented with GDNF, also induces the isolated rat UB (in the absence of MM) to undergo dichotomous branching reminiscent of that seen in the developing kidney. This indicates that the MM-derived cell line, presumably reflecting the MM itself, secretes soluble factors capable of inducing branching morphogenesis of the UB. This isolated UB culture system can serve as a powerful assay system since it directly assesses the effect of soluble factors on UB morphogenesis.

The invention demonstrates that serial liquid column chromatographic fractionation of BSN-CM contain an active morphogenetic fraction comprising a single polypeptide (capable of inducing branching morphogenesis comparable to whole BSN-CM). This polypeptide was identified as pleiotrophin (FIG. 2). Immunoblot analysis of BSN-CM (FIG. 7A) as well as in situ hybridization data of developing kidney (Vanderwinden et al., 1992), demonstrate that the embryonic MM is a source of pleiotrophin. In addition to its ability to induce branching morphogenesis in the isolated UB, pleiotrophin also induced a UB cell line to form branching tubular structures with lumens, and is thus the only soluble factor so far identified with this capability (FIG. 6). Based on this in vitro data with the isolated UB as well as the UB cell line, the invention provides methods and compositions for use in vitro and in vivo to induce morphogenesis and tubular formation of tissues (e.g., kidney tissue).

The invention provides a novel factor, and combination of factors capable of inducing UB branching morphogenetic activity. In one aspect, the invention provides an 18 kDa heparin binding protein, pleiotrophin, obtained from the BSN-CM. This factor has not previously been shown to play a role in kidney morphogenesis. Pleiotrophin was originally discovered as a fibroblast proliferative factor (Milner et al, BBRC, 165:1096-1103, 1989) and a neurite outgrowth-promoting factor (Rauvala, EMBO J, 8:2933-41, 1989). Outside the nervous system pleiotrophin is generally detected in those embryonic organs in which mesenchymal-epithelial interactions are thought to play an important role, such as salivary glands, lung, pancreas, and kidney (Mitsiadis et al., Development 121:37-51, 1995; Vanderwinden et al., Anat Ebryol (Berl) 186:387-406, 1992). Although pleiotrophin has been shown to be mitogenic for certain epithelial cells (Li et al., Science 250:1690-4, 1990; Sato et al., Exp Cell Res 246:152-64, 1999), there has been no compelling pleiotrophin during epithelial organogenesis.

The invention demonstrates that purified pleiotrophin induces impressive branching morphogenesis of the isolated UB in vitro. Thus, the invention provides methods of using pleiotrophin and compositions comprising pleiotrophin to induce morphogenesis in the kidney cells in vitro and in vivo. The invention further demonstrates that pleiotrophin is a key metanephric mesenchymally-derived factor that plays a critical role in branching morphogenesis of the UB during kidney development.

Pleiotrophin and another heparin binding growth factor, midkiue, make up a distinct growth factor family. These proteins share about 50% sequence homology (Rauvala, 1989), both are expressed widely during organogenesis (Mitsiadis et al., 1995), and are highly conserved among species (Kurtz et al., 1995). Both have been implicated in neurite outgrowth (Li et al., 1990; Rauvala et al., 1994), a phenomenon that has some similarity to branching morphogenesis particularly as it occurs in cultured cells), and they exhibit a spatiotemporal expression pattern in other developing organ systems which suggest a role in mesenchymal-epithelial interactions (Mitsiadis et al., 1995). However, other than the finding that pleiotrophin enhances bone formation (Imai et al., 1998) and limb cartilage formation (Dreyfus et al., 1998), little is known about the role of pleiotrophin in organogenesis. However, the invention demonstrates that pleiotrophin freshly purified to apparent homogeneity from either BSN cells or 3T3 cells induced impressive growth and branching morphogenesis of isolated UBs.

A wide range of concentrations of pleiotrophin has been reported to exhibit biological activity (up to 50 µg/ml) in various systems (Imai et al., 1998; Li et al., 1990; Rauvala et al., 1994; Souttou et al., 1997). Pleiotrophin binds to the extracellular matrix, which may explain why concentrations of 200-600 ng/ml were required for morphogenetic activity in the systems employed in Examples below (see also FIGS. 5A and 6). In the examples below the UB cell-line and isolated UBs were cultured within basement membrane Matrigel, which could conceivably bind a large fraction of pleiotrophin. In one aspect of the invention, similar artificial matrix systems, e.g., cell-free extracellular matrices (e.g., obtained by decellularizing a desired tissue), or synthesized matrices (e.g., lactic acid, glycolic acid, or combinations thereof) can be used and may similarly be modified to bind pleiotrophin.

To date, several glycoproteins, including brain-specific proteoglycans, the receptor type tyrosine phosphatase beta (Maeda and Noda, 1998; Meng et al., 2000) and syndecan-3 (Raulo et al., 1994) have been postulated to function as receptors for pleiotrophin. The UB has been shown to express syndecan-1 (Vainio et al., 1989), and pleiotrophin is capable of binding to syndecan-1 (Mitsiadis et al., 1995).

The involvement of proteoglycans in pleiotrophin-mediated branching morphogenesis of the UB is particularly interesting in light of data demonstrating the importance of proteoglycans in UB development (Bullock et al., 0.1998; Davies et al., 1995; Kispert et al., 1996). In these studies, chemical or genetic depletion of sulfated proteoglycans inhibits branching morphogenesis, and this is accompanied by decreased GDNF expression, and loss of c-ret at the UB tips (Bullock et al., 1998; Kispert et al., 1996). Even at early time points, when c-ret expression is still preserved, addition of exogenous GDNF alone does not completely restore UB branching morphogenesis (Sainio et al., 1997), again suggesting that other molecules are required in this process. One possibility is that depletion of sulfated proteoglycans also affects pleiotrophin-mediated signaling or binding. Accordingly, the invention provides that pleiotrophin functions as a MM-derived morphogen acting upon the UB. Moreover, the results support the idea that UB branching morphogenesis is likely to be regulated by more than a single factor. At least two soluble factors, GDNF and pleiotrophin can be used to induce morphogenetic changes. Other heparin-binding agents including heregulin can also be used in the methods of the invention along with or substituted for pleiotrophin, for example. GDNF may initiate the UB outgrowth (Sainio et al., 1997), and pleiotrophin (or other heparin binding agent such as heregulin) may induce proliferation and/or facilitate branching (FIGS. 5 and 8). In addition, the invention provides a combination of factors such as pleiotrophin GDNF and may include FGF. FGF and related members may play a facilitory role, since FGF1 potentiates the effects of purified pleiotrophin on UB branching morphogenesis, though by itself (with GDNF present) exerts little if any morphogenetic activity.

Inhibitory factors can also play a role in morphogenesis regulation and can include members of the transforming growth factor-beta family (Sakurai and Nigam, 1997). For example, gradients of positive and negative factors, most of which are matrix-bound, may exist in the mesenchyme and stroma By regulating proliferation, apoptosis and the expression of morphogenetic molecules at branch tips, branch points and stalks, the global and local balance of these stimulatory and inhibitory factors provide crucial determinant of branching patterns during collecting system development. In addition, sulfated proteoglycans should also be present either to maintain expression of these soluble factors or to secure their binding sites. At later stages, other soluble factors such as HGF and/or EGF receptor ligands may play supplementary roles, either during branching (particularly in the later stages) or shaping/maturation of tubular structures.

It should also be noted that the concentration-dependent morphogenetic changes induced by pleiotrophin in the UB (FIG. 5A), raise the possibility that pleiotrophin represents a "classical morphogen," in the sense of activin in early Xenopus development (Green and Smith, 1990). Such a molecule might be expected to produce different phenotypic changes in the responding tissue depending upon the concentration of the molecule to which it is exposed. In this regard, the basement membrane of the developing UB, to which pleiotrophin is localized, could potentially act as a "reservoir." Release of pleiotrophin from the basement membrane at the UB tips, perhaps through digestion by matrix degrading proteases, can produce a local concentration gradient, resulting in increased growth and proliferation of tips, while lower amounts of pleiotrophin along the length of the stalk would appear to induce elongation of the forming tubule. Such a concentration gradient of pleiotrophin provides a basis for modulating the shape and directionality of the developing UB. In another aspect of the invention, artificial matrices comprising biocompatible material may be used as a support for cell growth. Such matrices may be designed such that concentrations of pleiotrophin may change at desired branch points within the matrix material. In this manner, kidney cells may grow and proliferate through the matrix and only branch at locations where pleiotrophin concentrations are at a level to induce branching morphogenesis.

In another aspect of the invention there is provided methods and composition for treating acute renal failure (ARF). Acute renal failure is a common condition with a poor outcome. Nearly 200,000 patients in the United States develop ARF annually and the mortality rate remains high in spite of improved techniques of renal replacement therapy. At the present time, treatment of ARF is primarily supportive since no specific therapy is available. Recently improved understanding of the cellular and molecular mechanisms of ARF may be translated into new therapeutic approaches.

The most common etiologies of ARF are renal ischemia or the administration of a nephrotoxic drugs. In many cases, severe ARF results from a combination of renal hypoperfusion and nephrotoxicity. Severe ARF is associated with injury to renal tubular cells leading to both cellular dysfunction and ultimately cell death. The recovery from ARF is characterized by de-differentiation of the tubular epithelium, proliferation, and regeneration of the tubular cell. In many respects, these recovery processes recapitulate the processes fundamental to normal embryonic renal development, such as growth factor expression, matrix digestion, and intercellular tight junction modification.

The conditioned medium (BSN-CM), as well as purified subfractions, appear to be among the most powerful tubulogenic and proliferative growth factors known and have not been studied in the context of acute renal failure. There is a very strong correlation between known branching tubular morphogens and enhancement of recovery in experimental acute renal failure.

The invention provides a novel growth factor-based therapy for acute renal failure (ARF). ARF is primarily caused by acute tubular necrosis (ATN). ATN is manifested by renal cell death, and the recovery from ATN is characterized by a recapitulation of early developmental processes, particularly growth factor-induced tubulogenesis similar to that seen when kidney cells are contacted with BSU-CM or a composition comprising pleiotrophin. As discussed herein, the invention provides methods and compositions that utilize key mediators of kidney development in the treatment and prevention of ARF.

This invention provides a method of tubulogenesis and morphogenesis of kidney cells (e.g., UBs) in vivo in a subject comprising administering to the subject a composition comprising pleiotrophin in an amount effective to induce UB morphogenesis. In one embodiment, kidney cells are treated with a pleiotrophin ex vivo, and the kidney cells are then transplanted into a subject with diminished kidney function.

In another aspect of the invention, there is provided pharmaceutical compositions useful for treating tissue related disorders such as renal disorder and disorders associated with morphogenesis and/or tubulogenesis. In this aspect of the invention, the pharmaceutical composition comprises pleiotrophin in an amount that is effective to treat the particular disorder for which it will be administered. Generally, the pharmaceutical composition comprising pleiotrophin will be administered to a subject at a therapeutically effective doses to prevent, treat, or ameliorate a disorder or disease (e.g., a kidney disease). A therapeutically effective dose refers to that amount of pleiotrophin or pleiotrophin and other agents sufficient to result in a viable or measurable decrease in the disease or disorder symptoms.

Toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Compounds that exhibit large therapeutic indices are preferred. While compounds that exhibit toxic side effects can be used, care should be taken to design a delivery system that targets such compounds to the site of affected tissue to minimize potential damage to uninfected cells and, thereby, reduce side effects.

The data obtained from the cell culture assays and animal studies can be used to formulate a dosage range for use in humans. The dosage of such a composition lies typically within a range of circulating concentrations that include the $ED_{50}$ with little or no toxicity. The dosage can vary within this range depending upon the dosage form employed and the route of administration. For any compound used in the method of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography.

Pharmaceutical compositions for use in the invention can be formulated by standard techniques using one or more physiologically acceptable carriers or excipients. Thus, for example, pleiotrophin and its physiologically acceptable salts and solvates can be formulated for administration by inhalation or insufflation (either through the mouth or the nose), or oral, buccal, parenteral, intravenous, intramuscular, intradermal, intracerebral, or rectal administration.

For oral administration, the pharmaceutical compositions can take the form of tablets or capsules prepared by conventional means with pharmaceutically acceptable excipients such as binding agents, e.g., pregelatinised maize starch, polyvinylpyrrolidone, or hydroxypropyl methylcellulose; fillers, e.g., lactose, microcrystalline cellulose, or calcium hydrogen phosphate; lubricants, e.g., magnesium stearate, talc, or silica; disintegrants, e.g., potato starch or sodium starch glycolate; or wetting agents, e.g., sodium lauryl sulphate. The tablets can be coated by methods well known in the art.

Liquid preparations for oral administration can take the form of solutions, syrups, or suspensions, or they can be presented as a dry product for constitution with water or other suitable vehicle before use. Such liquid preparations can be prepared by conventional means with pharmaceutically acceptable additives such as suspending agents, e.g., sorbitol syrup, cellulose derivatives, or hydrogenated edible fats; emulsifying agents, e.g., lecithin or acacia; non-aqueous vehicles, e.g., almond oil, oily esters, ethyl alcohol, or fractionated vegetable oils; and preservatives, e.g., methyl or propyl-p-hydroxybenzoates or sorbic acid. The preparations can also contain buffer salts, flavoring, coloring, and/or sweetening agents as appropriate.

Preparations for oral administration can be suitably formulated to give controlled release of the active compound.

For administration by inhalation (e.g., where the disorder may be associated with the pulmonary system or may be more readily taken up by the body), the compounds are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

Pleiotrophin can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions, or emulsions in oily or aqueous vehicles, and can contain formulatory agents such as suspending, stabilizing, and/or dispersing agents. Alternatively, the active ingredient can be in powder form for constitution with a suitable vehicle, e.g., sterile pyrogen-free water, before use.

The compounds (e.g., pleiotrophin) can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

The compositions can, if desired, be presented in a pack or dispenser device which can contain one or more unit dosage forms containing the active ingredient. The pack can for example comprise metal or plastic foil, such as a blister pack. The pack or dispenser device can be accompanied by instructions for administration.

This invention provides a method of treating a subject suffering from kidney failure, which comprises administering to the subject, an effective amount of a composition comprising pleiotrophin to treat the subject's kidney failure.

This invention provides methods and compositions comprising pleiotrophin to stimulate endogenous kidney progenitors to differentiate and form tubules for the purpose of restoring kidney function in a subject.

In another embodiment, the goal is to create clonal subcolonies of specifically engineered, functional kidneys that are suitable for use in screening of drugs and agents to measure effects on specific kidney functions as well as for use in transplantation. Using the compositions and methods of the invention, it is possible to culture kidney components derived from a single UB in order to develop a kidney tissue in vitro. Normal kidney development consists of the reciprocal interaction between the UB and the metanephric mesenchyme (MM) as described herein. The methods of the invention provide the ability to reduce the amount of tissue that must be sacrificed from cadaver tissue or through invasive biopsy techniques in order to obtain sufficient tissue for in vitro generation of kidney tissue for screening and transplantation. The invention provides methods and compositions whereby a single progenitor cell or tissue is capable of generating multiple kidney tissues in vitro.

Using the methods of the invention and compositions of the invention it is possible to stimulate UB morphogenesis and MM epithelialization. The methods of and compositions provide for kidney development through co-culturing of MM and UBs in culture systems. The kidney development is initiated when the metanephric mesenchyme (MM) induces an epithelial outgrowth of the Wolfian duct, termed the ureteric bud (UB). The MM induces the UB to elongate and branch, and through multiple iterations of this branching program, the UB subsequently develops into the renal collecting system. In turn, the branching UB initiates the reciprocal induction of the MM and stimulates it to epithelialize and to form the tubular nephron. These nephrons then connect with the UB derived collecting system allowing drainage of fluid (e.g., urine) into the bladder in vivo. This process is repeated through successive iterations to achieve the approximately 1 million nephrons present in the adult human kidney.

For many years, this process of reciprocal induction was thought to depend on direct cell contact between the MM and UB. Although mesenchyme cleanly isolated from the UB could be induced to form tubules by nonspecific inducers such as spinal cord, the UB was not able to undergo branching morphogenesis in vitro when isolated from the surrounding mesenchyme.

As described herein, the invention overcomes these difficulties whereby the isolated UB undergoes impressive branching morphogenesis in vitro when exposed to several growth factors pleiotrophin (PTN) alone or in combination with other factors (e.g. GDNF and/or FGFI). Such other factors include glial cell-derived neurotrophic factor (GDNF), fibroblast growth factor-1 (FGF1), and proteins secreted by a mesenchymally derived cell line. In addition, the invention provides methods for regulating processes that govern UB branching morphogenesis, such as the matrix-binding requirements vis-a-vis integrin expression, the dependence of branching morphogenesis on heparin sulfate proteoglycans, and the roles of positive and negative modulators of branching. Other growth factors present in media conditioned by ureteric bud cells that can induce differentiation of isolated mesenchyme cultured in vitro include, for example, leukemia-inhibitory factor (LIF) and FGF2.

These advances have lead to the possibility of recombination of subcultures of each of the components of the kidney—the ureteric bud and the mesenchyme. Using the methods and compositions of the invention the isolated UB and mesenchyme can be recombined in vitro and grown in an autonomous fashion. The resultant kidney is morphologically and architecturally indistinguishable from a "normal" kidney and can be used for transplantation, as a source for the study of kidney function, and as a resource for determining drug-effects upon kidney function. Furthermore, the invention provides methods for partitioning/propagating the kidney or the cultured isolated ureteric bud into smaller fragments and support the in vitro development of these subfractions through several "generations." The methods of the invention further allow for these subfractions to be recombined with fresh mesenchyme to develop additional kidney tissue through the induction of the mesenchyme. Furthermore, these nascent nephrons formed contiguous connections with limbs of the branched UB. Consequently, the invention provide in vitro engineered kidney tissue comprising a population of renal primordia suitable for transplantation and derived from a single progenitor.

The methods provided by the invention utilize a novel, in vitro, approach to renal engineering that provides an ability to create colonies of kidney tissue (in some cases comprising genetically engineered cells) suitable for transplantation. In one aspect of the invention, an embryonic ureteric bud is separated from the surrounding metanephric mesenchyme and each component (e.g., the MM and UB) is cultured in isolation. In one aspect of the invention, the UB and/or the MM is then modified in vitro (as described herein) in a tailored fashion to express a specific polynucleotide (e.g., a heterologous polynucleotide) to obtain a desired function. The components are then recombined to allow the morphogenesis and development of kidney tissue in vitro (e.g., to generate a in vitro engineered kidney). The in vitro engineered kidney can then be used in transplantation, to screen for desired biological function, and/or to screen for agents, which modulate kidney function.

For example embryonic UB are dissected and separated from the surrounding metanephric mesenchyme (MM) (FIG. 13). The dissected cells are then used to grow an arborized structure from the isolated UB, which were subdivided into smaller fractions and used to induce additional generations of UBs that grow and branch in vitro. The continued growth and branching ins maintained in the closure of MM cells by culturing and subculturing the UBs in the presence of BSU-CM or a culture medium comprising pleiotrophin (e.g. PTN and GDNF+FGFI). The subfraction of UBs were used through three generations. The UB generations were then recombined with freshly isolated metanephric mesenchyme. The cells retained the ability to induce dramatic tubular epithelial differentiation of the mesenchyme (FIGS. 14 and 15). Furthermore, there appeared to be connections between induced tubules of the mesenchyme and terminal portions of the UB thereby providing a conduit between the tubule and urinary collecting system. The generated kidney opens up the possibility of uniquely tailoring specific components of either the nephron (derived from the mesenchyme) or tie collecting system (derived from the UB) in vitro in a potentially functional and transplantable organ.

Although the concept of transplanting fetal organs is not novel, there are several advantages to the approach provided by the invention. First, by culturing the UB and MM in vitro, the invention provides the unique opportunity to modulate each of their functions in a site-specific manner. For example, transfection of the mesenchyme with constructs expressing organic ion transporters would lead to increased capability to handle drugs and toxins, insertion of genes coding for growth factors, such as insulin-like growth factor (IGF), would lead to markedly enhanced in vitro engineered kidney development and improved functionality, insertion of immunomodulatory elements, such as repressors of co-stimulatory molecules, could be used to improved immune tolerance; stimulation of branching in the UB can lead to an increased number of resultant nephrons and improved renal functionality. Thus, there are numerous of ways to design a in vitro engineered kidney with tailored function. Furthermore, by subcloning either kidneys or UBs, the invention provides the potential to develop a large number of kidneys derived from a single progenitor, thus removing concerns surrounding limited supply of transplantable tissue. Third, it is possible to create a chimeric kidneys using the UB as a scaffold and recombining the UB with heterologous mesenchymal cells. These mesenchymal cells could be derived from embryonic stem cells that, when exposed to kidney derived signals from the UB induce differentiation of the renal mesenchymal cells into epithelial tissues. In normal adults, stem cells originating in the bone marrow repopulate portions of the kidney and differentiate into renal cells, and it is likely that embryonic stem cells also posses this ability. If it were possible to create such a chimeric kidney, it would greatly decrease the likelihood of immunologic problems that currently make transplantation difficult.

The approach provided by the methods and compositions of the invention, whereby in vitro engineered kidneys developed and/or are designed to possess specific functions, such as improved immune tolerance or enhanced tubular secretion of substrate, offer original approaches to transplantation and kidney therapy. Furthermore, creating clonal populations of in vitro engineered kidneys creates the potential for development of organ propagation from a single tissue. This approach is potentially applicable to other epithelial tissues such as lung and pancreas.

Large numbers of patients are awaiting renal transplantation. The development of techniques that allow for safe organ transplantation, especially without excessive immunosuppression, would have enormous commercial application. Transplantation of embryonic tissue appears to be well tolerated. The methods provided by the invention allow for the development of colonies of subcloned in vitro engineered kidneys that have been specifically tailored to express certain functions, and are immune-naïve. Immune naïve means that the cells lack "self" identification as the cells were fetally or stem cell derived and therefore should be immune tolerant.

Methods of transfecting and transforming cells are known in the art. For example, methods of transfecting/transforming kidney cell are known and include the following methods. Tomita et al. (Biochem. and Biophys. Res. Comm. 186:129-134, 1992) report a method for in vivo gene transfer into the rat kidney. They utilize HVJ (Sendai virus) and liposome methodology. In this protocol, plasmid DNA and a nuclear protein are coencapsulated in liposomes and later cointroduced into cells. The reporter gene utilized in these studies was the SV40 large T antigen. The gene transfer can be performed by inserting a cell or culture of kidney tissue with a liposome suspension. Transfection/transformation of the kidney cells can be assay by detecting SV40 large T antigen immunohistochemically. A study by Zhu et al. (Science 261: 209-11, 1993), reports the use of a particular cationic liposome DNA mixture to deliver genes with high efficiency into a vast number of endothelial cells in a rat. Moullier et al. (Kidney International 45:1220-1225, 1994) provides a first report of an adenoviral-mediated gene transfer into a kidney.

As used herein, the term "transfect" or "transform" refers to the transfer of genetic material (e.g., DNA or RNA) of interest via a vector into cells of a mammalian organ or tissue (e.g., kidney/renal tissue). The vector will typically be designed to infect mammalian kidney cell. The genetic material of interest encodes a product (e.g., a protein polypeptide, peptide or functional RNA) whose production by kidney cells is desired. For example, the genetic material of interest can encode a hormone, receptor, enzyme or (poly)peptide of therapeutic value. Examples of genetic material of interest include but are not limited to DNA encoding cytokines, growth factors and other molecules which function extracellularly such as chimeric toxins, e.g., a growth factor such as interleukin-2 (IL-2) fused to a toxin, e.g., the pseudomonas exotoxin, dominant negative receptors (soluble or transmembrane forms), truncated cell adhesion or cell surface molecules with or without fusions to immunoglobulin domains to increase their half-life (e.g., CTLA4-Ig). For example, cells of an organ or a tissue do not express a gene product encoded by the genetic material prior to transfection or transformation. Alternatively, infection of the cells of an organ or a tissue may result in an increased production of a gene product already expressed by those cells or result in production of a gene product (e.g., an antisense RNA molecule) which decreases production of another, undesirable gene product normally expressed by the cells of that organ or tissue. Generally, the genetic material encodes a gene product, which is the desired gene product to be supplied to the cells of that organ or tissue. Alternatively, the genetic material encodes a gene product, which induces the expression of the desired gene product by the cells of that organ or tissue (e.g., introduced genetic material encodes a transcription factor which induces the transcription of the gene product to be supplied to the subject). Furthermore, the genetic material could simply contain a polynucleotide, e.g., in the form of single stranded DNA to act as an antisense nucleotide. A genetic material infected into a cell of an organ or a tissue via a vector is in a form suitable for expression in the cell of the gene product encoded by that genetic material. Accordingly, the genetic material includes coding and regulatory sequences required for transcription of a gene (or portion thereof) and, when the gene product is a protein or peptide, translation of the gene product encoded by the genetic material. Regulatory sequences which can be included in the genetic material include promoters, enhancers and polyadenylation signals, as well as sequences necessary for transport of an encoded protein or peptide, for example N-terminal signal sequences for transport of proteins or peptides to the surface of the cell or for secretion, or for cell surface expression or secretion preferentially to the luminal or basal side. Enhancers might be ubiquitous or tissue or cell specific or inducible by factors in the local environment, e.g., inflammatory cytokines.

As used herein, the term an "effective amount" refers to a level of expression of a heterologous polynucleotide transfected or transformed into a kidney cell, which brings about at least partially a desired therapeutic or prophylactic effect in an organ or tissue infected by the method of the invention. For example, expression of genetic material of interest can then result in the modification of the cellular activities, e.g., a change in phenotype, in an organ or a tissue that has been infected by the method of the invention. In one embodiment, an effective amount of the expression of a heterologous genetic material of interest results in modulation of cellular activity in a significant number of cells of an organ transfected or transformed with the heterologous polynucleotide. A "significant number" refers to the ability of the vector to infect at least about 0.1% to at least about 15% of the renal endothelial cells or UBs. Typically, at least about 5% to at least about 15% of the cells are transfected/transformed. Most commonly, at least about 10% of the cells are transfected/transformed.

A vector refers to a polynucleotide molecule capable of transporting another nucleic acid to which it has been linked into cells. Examples of vectors that exist in the art include: plasmids, yeast artificial chromosomes (YACs) and viral vectors. However, the invention is intended to include such other forms of vectors which serve equivalent functions and which become known in the art subsequently hereto.

The efficacy of a particular expression vector system and method of introducing genetic material into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase polymerase chain reaction (RT-PCR). The gene product can be detected by an appropriate assay, for example by immunological detection of a produced protein, such as with a specific antibody, or by a functional assay to detect a functional activity of the gene product, such as an enzymatic assay. If the gene product of interest to be expressed by a cell is not readily assayable, an expression system can first be optimized using a reporter gene linked to the regulatory elements and vector to be used. The reporter gene encodes a gene product, which is easily detectable and, thus, can be used to evaluate the efficacy of the system. Standard reporter genes used in the art include genes encoding .beta.-galactosidase, chloramphenicol acetyl transferase, luciferase and human growth hormone.

The method of the invention can be used to infect kidney cells to obtain designer kidneys (e.g., genetically engineered kidney cells). As used herein, the term "kidney cells" is intended to including UB and MM cell types as well as the other 15 different cell types, e.g., glomerular cells, mesangial cells, interstitial cells, tubular cell, endothelial cells, are intended to be encompassed by the term "kidney cells".

The method of the invention can also be used to infect a kidney tissue generated ex vivo. For example, in a transplant setting, a kidney is engineered by the methods of the invention, the "in vitro engineered kidney" is then perfused (e.g., the collecting ducts) with a vector carrying genetic material of interest.

One potential application of the invention is in renal allograft or xenograft tissue transplantation. In this aspect, kidney tissue generated by the methods and compositions of the invention are transfected/transformed with an agent (e.g., delivered to MM cells and/or UBs) that results in organ tolerance or might help in the post-operative period for decreasing the incidence of early transplant rejection or function (e.g., due to acute tubular necrosis). Either the organ can be made less immunogenic so as to reduce the number of host T cells generated and/or the endothelial cells (e.g., endothelial cells derived from MM) can be altered so as to prevent the adhesion/transmigration of primed immune T-cells or killer effector T-cells (e.g., by use of IL-2-toxin fusion proteins). Moreover, genes transfected/transformed into in vitro engineered kidney tissue, such as nitric oxide synthetase (NOS), prior to transplantation could also serve to protect the organ post transplantation. These strategies make clinical sense since it is well known that early rejection episodes and malfunction lead to a worse long-term graft survival. Therefore, prevention of acute rejection and preservation of function immediately post transplant are of particular importance. Delivery of the genetic material (i.e., the heterologous polynucleotides) for this purpose can be done using methods known in the art including utilizing an adenovirus vector, lipofection, or other techniques known in the art. In addition to the heterologous polynucleotides mentioned above, these vectors can carry additional sequences comprising anti-sense constructs to one or more cell adhesion molecules (involved in lymphocyte homing) or dominant negative constructs to these molecules, or antisense constructs to MHC antigens in the transplant or locally immune suppressive lymphokines such as interleukin-10 (IL-10) or viral IL-10 or chimeric toxins which would preferentially kill T-cells, e.g., IL-2 toxin fusion protein. It is also possible that one could interfere with the recognition part of the immune system by, for example, the local secretion of CTLA4-IgG fusion proteins. This list of candidate polynucleotides is not exhaustive. Those skilled in the art of transplantation know of others. The genes could be delivered with constitutive promoters or with appropriate inducible enhancers.

The source of cells used to ultimately engineer kidney tissues need not be derived from the kidney per se. Pluripotent embryonic stem (ES) cells and pluripotent embryonic germ (EG) cells can serve as progenitor cells for a variety of differentiated cell types and recent work with human ES and EG cells has opened the doors to some potential beneficial therapeutics for diseases as diverse as neurodegenerative disorders and cardiomyopathy. For example, mouse ES cells treated with retinoic acid in vitro can be induced to form neurites in vitro. When transplanted back into rat spinal cord, these neuronal cell precursors survive, differentiate into distinct and functional neuronal cell types, such as astrocytes, myelin-producing oligodendrocytes, and neurons, migrate to areas of injury/repair, and lead to increased functional outcome. When cultivated in vitro, human ES and EG cells form 3-dimensional aggregates called embryoid bodies (EB) that can then differentiate into derivatives of all three primary germ cell layers. Furthermore, these EB can be induced to differentiate into specific but different cellular subsets based on conditioning by certain growth factors, such as FGF and TGF-beta. Cells derived from ES and EG cells can organize and can display a diverse set of functional properties, such as contractility in ES-derived cardiomyocytes and insulin secretion from ES-derived "islet-like" cells. Finally, multipotent adult bone marrow-derived mesenchymal stem cells (MSC) may serve as an adult source of stem cells readily available for engineering of tissues derived from mesenchyme. Within the context of the kidney, cells derived from the bone marrow were found to repopulate or regenerate a variety of renal territories, including the glomerular podocyte and mesangium, interstitium, and renal epithelial tubule. Recent work suggests that there may exist one or more self-renewing "renal stem cells" found within the MM that can differentiate into the myofibroblasts of the renal stroma and/or endothelium.

As discussed herein, the invention provide methods and compositions whereby isolated UBs can be co-cultured and stimulated by extrinsic factors to induce branching and kidney development. For example, whole isolated intact UB (cleanly separated from surrounding MM) can be induced to undergo branching morphogenesis in vitro in a manner similar to UB culture. Suspension of the isolated UBs within, or on, a natural or artificial biocompatible substrate (e.g., Matrigel/collagen gel) and when exposed to a mixture of mesenchyme-cultured media augmented with GDNF, results in the isolated unbranched UB rapidly forming a polarized, extensively branched structure with an internal lumen. As described further herein, pleiotrophin, which induced branching of UB-derived cells, also induces impressive branching morphogenesis of the whole ureteric bud. Other factors have been found to modulate the branching effect of BSN-CM or pleiotrophin on the UB. This modulation is typically branch-promoting, elongation promoting, or branch-inhibiting. For example, FGF1 induced the formation of elongated UB branching stalks whereas FGF7 induced amorphous buds displaying nonselective proliferation with little distinction between stalks and ampullae. TGF-beta, which inhibits branching in several cell-culture model systems, also appears to inhibit the branching of the isolated UB. Endostatin, which is a cleavage product of collagen XVIII normally found in the UB basement membrane, also selectively inhibits branching of the UB. Growth factors, such as LIF, have been isolated from UB conditioned media and induce mesenchymal-to-epithelial transformation of cultured mesenchyme. Other factors, such as FGF2, appear to promote survival but not differentiation of mesenchyme.

The branching isolated ureteric bud retains the ability to induce freshly isolated mesenchyme when recombined in vitro without exogenous growth factors. By carefully removing the surrounding biocompatible matrix from the cultured UB and placing mesenchyme in close proximity, the UB continues to grow and extend branches into the surrounding mesenchyme. Furthermore, the mesenchyme condenses in areas where the UB has extended branches, and then epithelializes in a manner similar to normal kidney development. This has wide-ranging implications for in vitro kidney engineering, including the ability to independently culture ureteric bud and metanephric mesenchyme, modify their phenotypes in vitro, and then recombine them. For example, it may be possible to develop engineer kidneys with properties such as enhanced drug or toxin secretion by in vitro modification of organic anion transporters, improved immune tolerance by suppression of costimulatory molecules, as discussed herein. The invention demonstrates that these recombined "in vitro engineered kidneys," comprised of cultured isolated UB and freshly isolated mesenchyme, form cohesive intact tubular conduits. That is, the nascent tubular nephron, derived from MM, has a tubular lumen in direct connection with the tubular lumen of the collecting system, derived from the UB.

In addition, the culture system and methods of the invention provide the ability to propagate the isolated UB in vitro through several generations. For example, isolated UB are cultured in vitro and induced to undergo branching morphogenesis in the presence of BSN-CM, FGF1, and GDNF. After 8 days, the cultured bud is subdivided into approximate 3rds and resuspended within a suitable biocompatible matrix (matrigel/collagen gel). This 2nd generation bud is further subdivided after another 8 days of culture, and the 3rd generation bud is cultured for 8 days (thus yielding at least 9 subdivided buds from one progenitor bud). These subsequent clonal generations of cultured UB retain the ability of the progenitor bud to induce mesenchyme upon in vitro recombination. The buds also retained the capacity to form cohesive conduits with the mesenchymally-derived tubules that they induced. Thus, the invention provides the ability to develop and propagate a clonal, expanded, and long-lived colony of ureteric buds, derived from a single progenitor bud that retains the properties of the progenitor. Using similar techniques with the MM, it is possible to develop colonies of mesenchyme derived from a single progenitor mesenchyme that can then be recombined with a propagated UB.

Whole embryonic kidneys can be propagated in a similar manner in vitro. After culturing these kidneys for 3 days, it is possible, using the methods of the invention, to subdivide into approximate 3rds the whole cultured kidney and then propagate the subsequent generations in vitro. At least 3 generations, yielding 9 kidneys, were generated from a single progenitor kidney using the methods and compositions of the invention. Thus, the methods and compositions of the invention provide the ability for expansion of syngeneic rudiments in vitro prior to transplantation into suitable hosts.

In many tissue-engineering technologies, an extrinsic biocompatible scaffold is required to provide orientation and support to the developing tissue. In one sense, the native polymeric basement membrane (BM) is a bioactive scaffold directing the normal development of the kidney. BM constituents such as endostatin can directly influence branching of the UB, and other components, such as HSPGs, can indirectly regulate growth by binding and releasing growth factors. These processes may be developmentally coordinated by the regulated expression of matrix metalloproteases (e.g. MMP2, MMP9, and TIMP-1). The bioartificial scaffolds used in tissue engineering can be synthetic or biologic and contain or can be coated with ECM constituents, such as collagen or proteoglycans. Exciting new techniques in materials science are emerging that allow these scaffolds to be impregnated with drugs, proteins, or even DNA, and thus may be more biologically relevant. By combining a truly bioactive scaffold with cultured pluripotent cells, such as ES cells, or multipotent cells, such as MSCs or other progenitor cells derived from the mesenchyme, it may be possible to coordinate inductive signals required to derive/engineer an organ such as the kidney. For example, vary the concentration of factors at points where branching is desired, it is possible to design a tissue having a predicted number of branch point.

Biocompatible support materials (biocompatible scaffolds) for culturing kidney cells include any material and/or shape that: (a) allows cells to attach to it (or can be modified to allow cells to attach to it); and (b) allows cells to grow in more than one layer. A number of different materials may be used as a culture support, including, but not limited to, nylon (polyamides), dacron (polyesters), polystyrene, polypropylene, polyacrylates, polyvinyl compounds (e.g., polyvinylchloride), polycarbonate (PVC), polytetrafluorethylene (PTFE; teflon), thermanox (TPX), nitrocellulose, cotton, polyglycolic acid (PGA), cat gut sutures, cellulose, gelatin, dextran, collagen, decellulularized tissue (both allogenic and xenogeneic), and like.

In one aspect of the invention a ureteric bud is used as a bioactive scaffold, which could then serve as a biologically-relevant orchestrator (conductor) of the complex inductive signals that underlie "normal" renal development. In an organ such as the kidney, where development is dependent on coordinated interactions between epithelium and mesenchyme, utilization of a biologically active epithelial scaffold to induce proper differentiation, maturation and integration of surrounding multipotent cells may provide a unique opportunity to modify specific cellular functions in vitro but yet to retain the complex organizational direction required to develop a mature kidney. This principle is applicable to engineering of other organs, such as lung, liver, pancreas, salivary gland or breast, which are also dependent upon mesenchymal-epithelial interactions within the context of a branching epithelial derivative. In one experiment, the UB, co-cultured with lung mesenchyme, began to express surfactant protein. Accordingly, the UB serves as a scaffold for a number of novel "chimeric" organs. The ability to independently culture and then combine mesenchymally-derived elements with epithelial-derived elements allow for the integration of cellular and organ-based approaches to tissue engineering. This approach would allow one to modify cell-based elements in vitro to possess certain desirable properties but still take advantage of an organ-based approach to tissue engineering.

In another aspect of the invention, the kidney cultures of the invention (UB alone, MM alone, and co-cultures thereof) may be used in vitro to screen a wide variety of compounds, such as cytotoxic compounds, growth/regulatory factors, pharmaceutical agents, and the like to identify agents that modify kidney function and/or cause cytotoxicity and/or kidney cell death or modify kidney proliferative activity. Examples of such agents or compounds include growth factors, peptides, and small organic molecules.

To this end, the cultures (e.g., UB primary cells, UB cell lines, MM cells, whole organ cultures, MM/spinal cord co-cultures, and UB/MM co-cultures) are maintained in vitro and exposed to the compound to be tested. The activity of a cytotoxic compound can be measured by its ability to damage or kill cells in culture or by its ability to modify the function of kidney cells (e.g., UB proliferative capacity, branching capacity, MM epithelialization capacity, particular gene expression, cell size, cell morphology, protein expression, and the like). This may readily be assessed by vital staining techniques, ELISA assays, immunohistochemistry, PCR, microarray analysis, and the like. The effect of growth/regulatory factors on the kidney cells. (e.g., UBs, MMs) may be assessed by analyzing the cellular content of the culture, e.g., by total cell counts, and differential cell counts, including the number of branch points. This may be accomplished using standard cytological and/or histological techniques including the use of immunocytochemical techniques employing antibodies that define type-specific cellular antigens. The effect of various drugs on normal cells cultured in the culture system may be assessed. For example, UB primary cells or cell lines may be cultured in vitro under conditions that stimulate branching morphogenesis/tubulogenesis (e.g., in the presence of BSN-CM, pleiotrophin, or pleiotrophin+other factors). A test compound is then contacted with the culture and the effect the test compound has on branching morphogenesis/tubulogenesis can be compared to a control, wherein a difference is indicative of a compound that increases or decreases branching morphogenesis.

The cytotoxicity to kidney cells (e.g., human UBs and co-cultures of MM and UBs) of pharmaceuticals, anti-neoplastic agents, carcinogens, food additives, and other substances may be tested by utilizing the culture system of the invention.

First, a stable, growing kidney culture comprising UB and/or MM cells is established. Then, the culture is exposed to varying concentrations of a test agent. After incubation with a test agent, the culture is examined by phase microscopy to determine the highest tolerated dose—the concentration of test agent at which the earliest morphological abnormalities appear. Cytotoxicity testing can be performed using a variety of supravital dyes to assess cell viability in the culture system, using techniques well-known to those skilled in the art.

Once a testing range is established, varying concentrations of the test agent can be examined for their effect on viability, growth, and/or morphology of the different cell types constituting the kidney culture by means well known to those skilled in the art.

Similarly, the beneficial effects of drugs may be assessed using the culture system in vitro; for example, growth factors, hormones, drugs which enhance kidney formation, or activity (e.g., branching activity) can be tested. In this case, stable cultures may be exposed to a test agent. After incubation, the cultures may be examined for viability, growth, morphology, cell typing, and the like as an indication of the efficacy of the test substance. Varying concentrations of the drug may be tested to derive a dose-response curve.

The culture systems of the invention may be used as model systems for the study of physiologic or pathologic conditions. For example, in a specific embodiment of the invention, the culture system can be optimized to act in a specific functional manner as described herein by modifying genome of the cells.

The kidney culture system of the invention may also be used to aid in the diagnosis and treatment of malignancies and diseases. For example, a biopsy of a kidney tissue may be taken from a subject suspected of having a malignancy or other disease or disorder of the kidney. The biopsy cells can then be separated (e.g., UBs from MM cells etc.) and cultured in the according to the methods of the invention. UBs from the subject can be co-cultured with normal (e.g., heterologous MM cells) to determine biological function of the UBs compared to UBs derived from a normal kidney. Similarly MM cells from the subject can be cultured with normal UBs to examine MM function and activity. In addition, such cultures obtained from biopsies can be used to screen agent that modify the activity in order to identify a therapeutic regimen to treat the subject. For example, the subject's culture could be used in vitro to screen cytotoxic and/or pharmaceutical compounds in order to identify those that are most efficacious; i.e. those that kill the malignant or diseased cells, yet spare the normal cells. These agents could then be used to therapeutically treat the subject.

Where in vitro engineered kidney tissue is generated according to the methods and compositions of the invention transplantation of the tissue can be performed as follows. Surgery is performed on the recipient subject to expose one or both kidneys. The in vitro engineered kidney tissue is implanted directly into/adjacent to the recipient subject's kidney to result in the formation of chimeric kidney, or into a fold of the omentum where it forms a chimeric kidney that functions independently of the recipient's kidney. The omentum, which is a membranous structure the connects the bowels, is a highly vascularized tissue sufficient for the transplantation of the in vitro engineered kidney. The in vitro engineered kidney can be placed adjacent to any portion of the omentum, however, in one aspect the in vitro engineered kidney is transplanted at or near an omental fold. In another aspect, the in vitro engineered kidney is transplanted at an omental fold located near one of the recipient's kidneys, particularly near the ureter, so that the developing ureter of the metanephros can be readily connected to the recipient's excretory system.

When implanted into the recipient's kidney, an incision, large enough to receive the in vitro engineered kidney tissue is made in the fibrous renal capsule that surrounds the recipient's kidney. The location of the incision can be anywhere in a viable portion of the recipient's kidney, but most conveniently will be at an external border of the kidney that is easily accessible during surgery. The in vitro engineered kidney tissue is placed between the capsule and the cortex of the recipient kidney.

The implanted in vitro engineered kidney tissue is allowed to grow within the recipient under conditions that allow the tissue to vascularize. Suitable conditions may include the use of pre or post-operative procedures to prevent rejection of the implant as well as the administration of factors (e.g., pleotrophin, FGF1, GNDF, and the like) that stimulate tubulogenesis and/or morphogenesis of the in vitro engineered kidney tissue. Immunosuppression techniques (in the absence or combined with genetically engineered techniques) such as cyclosporin A (CSA) to prevent rejection of the donor tissue are known in the art.

EXAMPLES

Unless otherwise stated, the incubations were performed at 37° C. in an atmosphere of 5% $CO_2$ and 100% humidity. For the immunodetection of pleiotrophin either on western blots or frozen sections of E13 mouse kidney, a goat anti-pleiotrophin antibody (R&D systems) was used.

Conditioned medium secreted by metanephric mesenchyme-derived cells is required for isolated UB branching morphogenesis. To identity mesenchymal factors that induce branching morphogenesis of the ureteric bud (UB), a metanephric mesenchyme (MM)-derived cell line (BSN cells) was employed as a substitute for the embryonic MM. These cells were derived from the embryonic day 11.5 (E11.5) MM from a SV40 large T-expressing transgenic mouse and have been extensively characterized. BSN cells are positive for vimentin and negative for cytokeratin, E-cadherin, and ZO-1 by immunostaining, as well as negative for Dolichos biflorus lectin-binding. By PCR the cells express WT1 and are negative for c-ret. The cells also express mRNA for growth factors such as HGF and TGFβ by northern blot. cDNA array analysis has confirmed their non-epithelial character. Most importantly, conditioned medium elaborated by BSN cells (BSN-CM) acts similar to the MM by inducing branching morphogenesis of cultured UBs and the isolated UB (in the presence of GDNF).

Figure 1A:
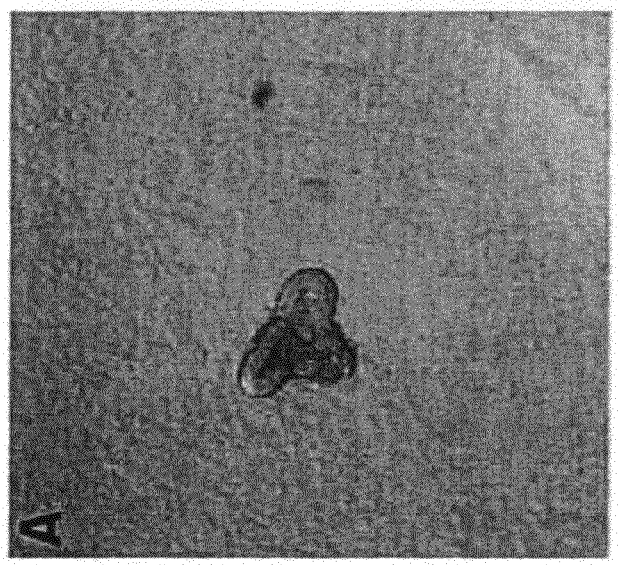
FIG. 1 indicates that BSN-CM induces branching morphogenesis of isolated ureteric bud tissue. Phase contrast photomicrographs of isolated ureteric buds cultured for 14 days in the presence (b) or absence (c) of BSN-CM in 10% FBS, 125 ng/ml GDNF and 250 ng/ml FGF1. In the presence of BSN-CM, the T-shaped ureteric bud (a) underwent extensive branching morphogenesis (b). In the absence of BSN-CM, no significant growth/morphogenesis was observed (c). Bar=500 μm.
Figure 1B:
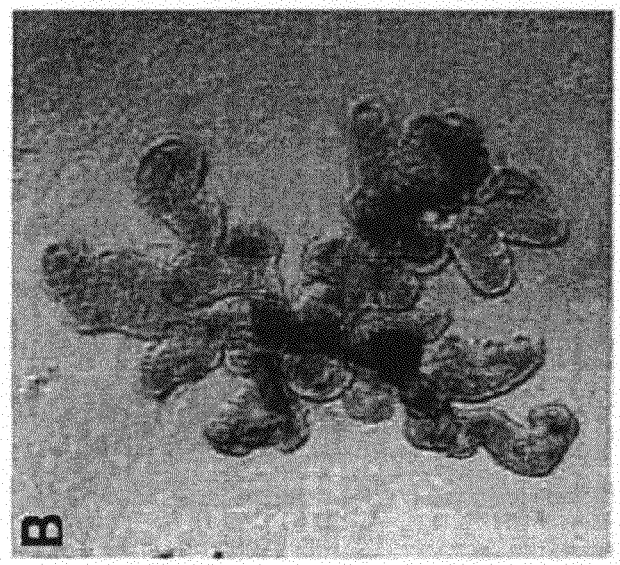
Figure 1C:
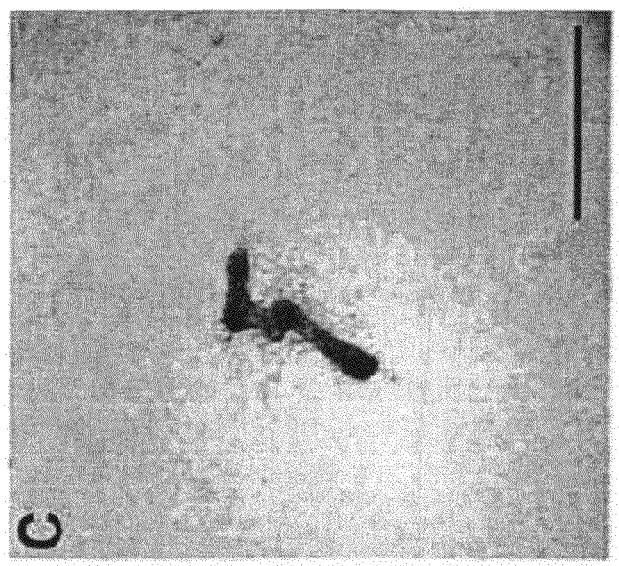

UBs isolated from E13 rat embryos, when suspended in an extracellular matrix gel and cultured in the presence of BSN-CM (with GDNF), grew to form impressive multiply branching tubular structures comparable to those seen in in vivo kidney development (though the growth was non-directional) (FIG. 1B). In the absence of BSN-CM, however, the UBs failed to develop (FIG. 1C). Thus, BSN-CM contains an additional soluble factor(s) necessary for epithelial cell branching morphogenesis. Using this isolated UB culture model as an assay, Inventors attempted to purify the key morphogenetic factor present in the BSN-CM.

Example 1

BSN cells were grown to confluency in DMEM/F12 supplemented with 10% fetal calf serum (FCS). The growth media was removed and the cells were then incubated in serum-free DMEM/F12 for 3-4 days followed by collection of the conditioned medium. Swiss ST3 cells (ATCC) were grown to confluence in DMEM with 10% FCS. Once the cells were confluent, the growth media was replaced with DMEM supplemented with 2% FCS and the cells were cultured for an additional 3-4 days. The conditioned medium was collected and used for the experiments. UBs were cultured in DMEM supplemented, with 10% FCS at 32° C. in an atmosphere of 5% $CO_2$ and 100% humidity.

Example 2

Timed pregnant female Sprague-Dawley rats at day 13 of gestation (day 0 coincided with appearance of the vaginal plug) were sacrificed and the uteri were removed. The embryos were dissected free of surrounding tissues and the kidneys were isolated. For the culture of the whole kidney rudiment, 2-3 kidneys were applied directly to the top of a polyester Transwell filter (0.4 μm pore size; Corning-Costar). The Transwells were then placed within individual wells of a 24-well tissue culture dish containing 400 μl DMEM/F12 supplemented with 10% FCS with or without purified pleiotrophin. Following 7 days of culture, the kidneys were fixed in 2% paraformaldehyde and doublestained with fluorescein-conjugated Dolichos biflorus, a lectin which binds specifically to UB-derived structures, and rhodamine conjugated peanut agglutinin, a lectin which binds to structures derived from the MM. Fluorescent staining was detected using a laser-scanning confocal microscope (Zeiss).

In the case of culture of the isolated UB, the isolated kidneys were trypsinized for 15 min at 37° C. in L-15 media containing 2 µg/ml trypsin (Sigma). Trypsin digestion was arrested by the addition of 10% FCS and the kidneys were removed to fresh L-15 where the UBs were isolated from surrounding MM by mechanical dissection. isolated UBs were suspended within an extracellular matrix gel [1:1 mixture of growth factor reduced Matrigel (BD) and Type 1 collagen (BD)] applied to the top of a polyester Transwell filter (0.4 µm pore size; Corning-Costar). The Transwells were placed within individual wells of a 24-well tissue culture dish containing 400 µl of either whole BSN-CM, purified tractions of BSN-CM, or D-12 which were supplemented with human recombinant FGF1 (250 ng/ml; R&D Systems), rat recombinant GDNF (125 ng/ml; R&D Systems) and 10% FCS and cultured as previously described (Qiao et al., PNAS USA 96:7330-5, 1999). Phase-contrast photomicrographs of the developing UB were taken using a RT-Slider Spot Digital Camera (Diagnostic Instruments Inc.) attached to a Nikon Eclipse TE300 Inverted Microscope.

Example 3

Confluent monolayers of UBs were removed from tissue culture dishes by light trypsinization and the cells. 20,000 cells/ml were suspended in an extracellular matrix gel composed of 80% Type 1 collagen and 20% growth factor-reduced Matrigel. 100 µl of the UB cell-containing gel was then aliquoted into individual wells of a 96-well tissue culture plate. After gelation, 100 µL of growth medium (DMEM/F12 with or without purified pleiotrophin) supplemented with 1% FCS was applied to each well and the cultures were incubated at 32° C. in 5% $CO_2$ and 100% humidity. Following 4 days of culture, the percentage of cells/colonies with processes was counted as an indicator of the tubulogenic activity. Phase-contrast photomicrographs were taken as described herein.

Example 4

1.5-2 L of BSN-CM collected as described herein was filtered to remove extraneous cellular debris using a 0.22 µm polyethersulphone membrane filter (Corning). The BSN-CM was then concentrated 40-fold using a Vivatlow 200 concentrator with a 5 kDa molecular weight cutoff (Sartorius). After adjusting the salt concentration to 0.4 M NaCl, the concentrated BSN-CM was then subjected to sequential liquid column chromatography using an AKTA purifier (Amersham-Pharmacia). Initial fractionation was performed using a heparin sepharose chromatography column (HiTrap heparin, 5 ml; Amersham Pharmacia). The flow-through fraction was collected and individual 5 ml fractions of the heparin-bound proteins were eluted via increasing concentrations of NaCl (0.4 M-2.0M) buffered to pH 7.2 with 50 mM HEPES. Aliquots of each fraction were subjected to buffer exchange by dia-filtration using an Ultrafree 500 spin column (Millipore) according to the manufacturer's instructions and then tested for morphogenetic activity using the isolated UB culture system.

An active fraction corresponding to the 1.2-1.4 M NaCl eluate was identified based on its ability to induce branching morphogenesis of the isolated UB. After adjusting this fraction to 1.7 M ammonium sulfate (pH 7.2) it was subjected to further fractionation using a Resource phenyl sepharose hydrophobic interaction column (1 ml; Amersham-Pharmacia). The flow through was collected and 1 ml fractions of bound proteins were eluted with decreasing concentrations of ammonium sulfate (1.7 M-0 M). After buffer exchange, the individual fractions were again tested for their ability to induce UB branching morphogenesis.

The morphogenetically active fractions from the hydrophobic interaction column were diluted 10-fold with 50 mM HEPES and applied to a Resource S cation exchange column (1 ml; Amersham-Pharmacia). The flow-through was collected and individual 1 ml fractions of bound proteins were eluted-using increasing NaCl concentrations (0 M-2.0 M) and assayed for the ability to induce branching morphogenesis.

The active fractions from the Resource S cation exchange column were subjected to further fractionation using a Superdex 200 gel filtration column (Amersham-Pharmacia). Individual 1 ml fractions were collected and assayed for morphogenetic activity. In addition, the active fractions from the Resource S cation exchange column were subjected to SDS-PAGE and the proteins were visualized using coumassie blue (Colloidal Coumassie; Invitrogen) staining. Individual protein bands were cut out of the gels and submitted for microsequencing. Sequence analysis of the protein bands was performed at the Harvard Microchemistry Facility by microcapillary reverse phase HPLC nanoelectrospray tandem mass spectrometry (pLC/MS/MS) on a Finnigan LCQ DECA quadrupole ion trap mass spectrometer.

Figure 2A:
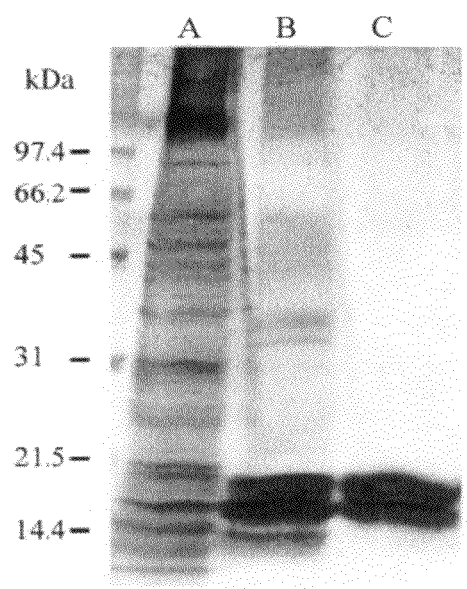
FIG. 2 shows the purification protocol for a morphogenetic factor in BSN-CM. (A) Silver stained SDS-PAGE gel of active fractions from column chromatography of BSN-CM (a) Lane 1, whole BSN-CM; (b) Lane 2, active fraction from heparin sepharose column; (c) Lane 3, active fraction from a resource phenyl sepharose column. A single sharp protein peak was eluted at 0.4-0.6 M NaCl. Each of the individual 1 ml fractions eluted from the column are indicated by the gray numbers along the X-axis. (C) Phase-contrast photomicrographs of isolated ureteric buds cultured for 7 days in the presence of each 1 ml fraction from a Resource S cation exchange column (1-8 in B) supplemented with 10% FBS, 125 ng/ml GDNF, and 250 ng/ml FGF1. Fraction 4, which corresponded with the protein peak on the elution profile (B) exhibited potent morphogenetic activity. Bar=500 μm. (D) Silver stained SDS-PAGE gel of each fraction (1-8) eluted from the resource S cation exchange column (B). Fraction 4, which possessed potent morphogenetic activity, (C) contained a single low molecular weight band, which was identified as pleiotrophin by mass spectrometry. (E) immunoblot analysis of the individual fractions eluted from the resource S cation exchange column (1-8 in B). The blot was probed with anti-pleiotrophin antibodies. Left lane; 250 ng of human recombinant pleiotrophin as a positive control.
Figure 2B:
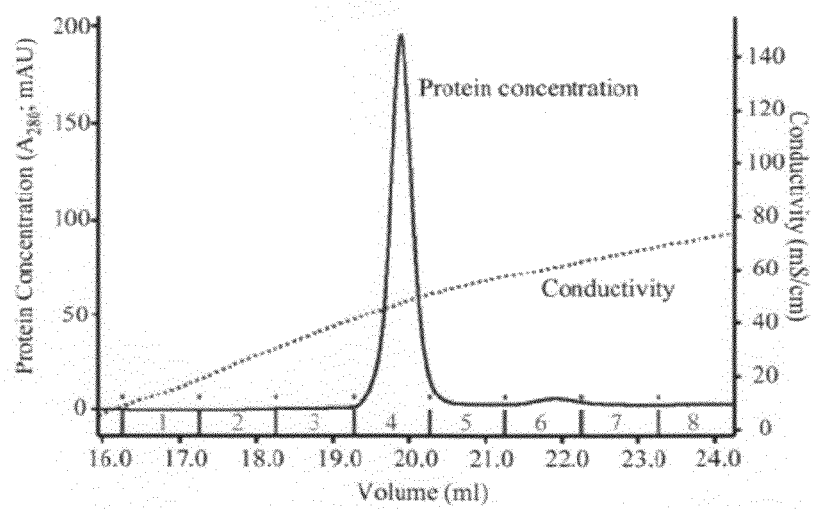
Figure 2C:
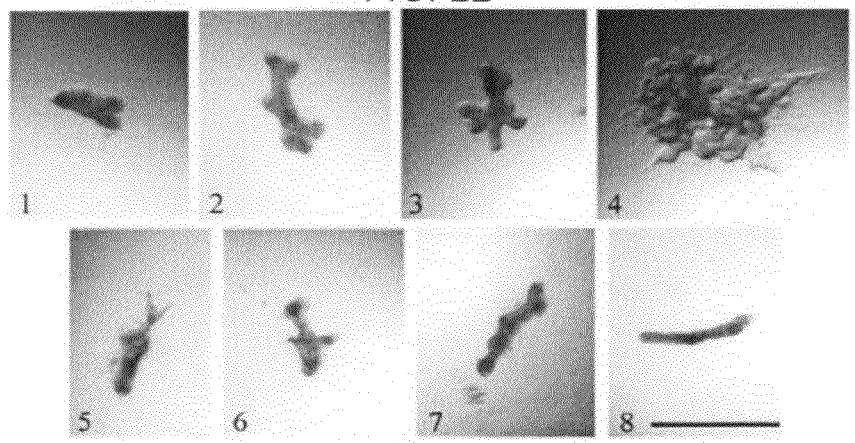
Figure 2D:
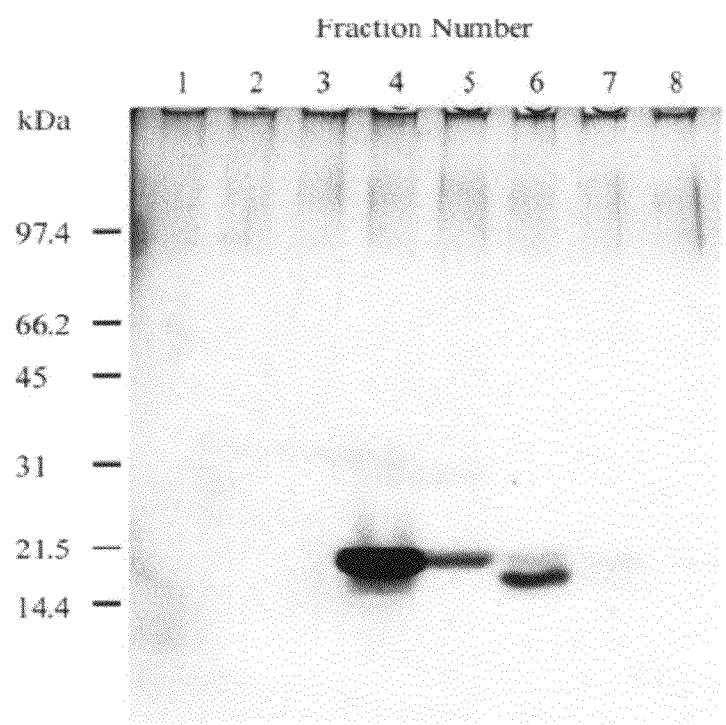

SDS-PAGE and silver staining of BSN-CM revealed the presence of many protein bands (FIG. 2A). As described above, liquid column chromatography was used to fractionate BSN-CN and each fraction was tested for its ability to induce branching morphogenesis of the isolated UB. Of the multiple columns tested, a heparin sepharose column was found to adsorb most of the morphogenetic activity. Within this heparin-binding fraction, the fraction, which eluted at a NaCl concentration of 1.2-1.4 M possessed particularly strong morphogenetic activity. Silver stain analysis of this fraction revealed the presence of prominent lower molecular weight (40 kDa) protein bands (FIG. 2A). This active fraction was then applied to a Resource phenyl sepharose hydrophobic interaction column. A morphogenetic activity was eluted from this column at 1.4 1.2 M ammonium sulfate. Again, silver staining of this peak fraction revealed prominent low molecular weight protein bands (FIG. 2A). This active fraction was diluted 10-fold with 50 mM HEPES (pH 7.2) buffer and applied to a Resource S cation exchange column. The Resource S column chromatogram is shown in FIG. 2B. Each 1 ml fraction of the Resource S eluate was substituted for whole BSN-CM in the isolated UB culture and compared with BSN-CM itself. Of the 8 fractions eluted from the column, only Fraction 4, the peak protein fraction, induced significant UB morphogenesis (FIG. 2C, panel 4). SDS-PAGE analysis and silver staining of this peak fraction revealed the presence of a single protein band with an approximate molecular weight of 18 kDa (FIG. 2D, Lane 4). This protein band was subjected to in-gel digestion followed by tandem mass spectrometry and was identified as pleiotrophin. (This type of experiment was performed at least 3 times during different purifications, and pleiotrophin was always detected by mass spectrometry).

Figure 2E:
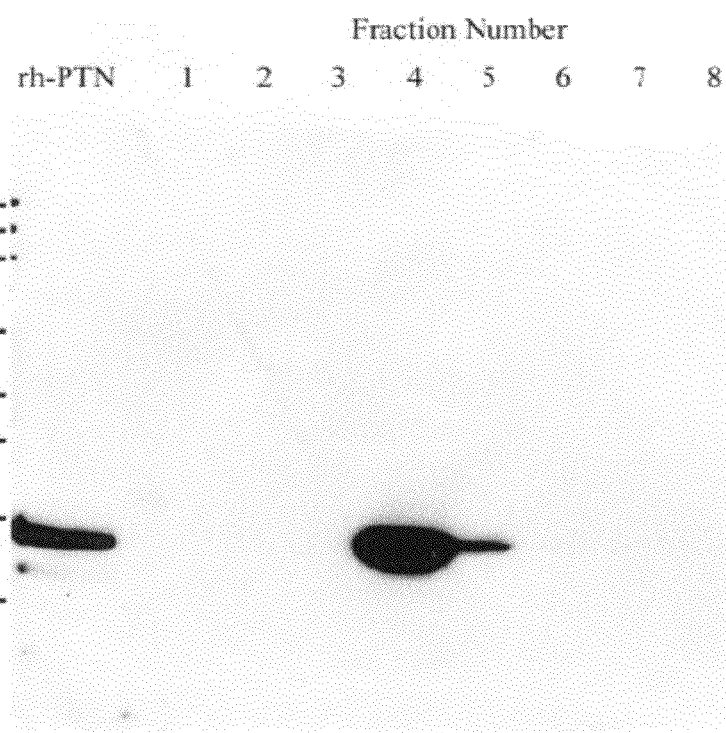
Figure 3A:
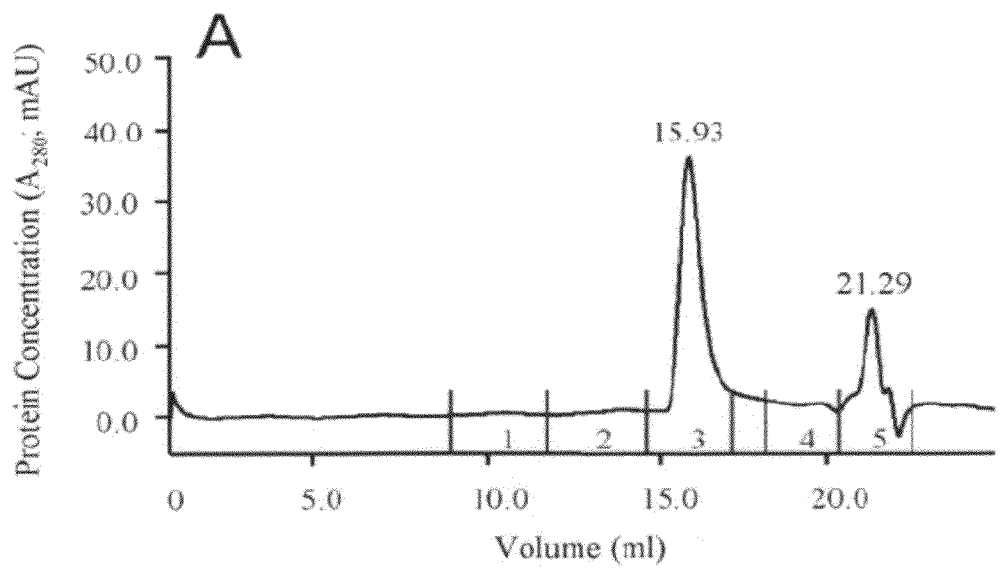
FIG. 3 shows gel filtration chromatography profile of the eluate from the Resource S cation exchange column. (A) Elution profile from a Superdex 200 gel filtration column of the peak fraction from the Resource S cation exchange column (FIG. 2B, fraction 4). A single protein peak was eluted at 15.93 ml, which corresponds to a relative molecular mass of 18 kDa. Each of the individual 1 ml fractions are indicated by the numbers along the x-axis. (B) Immunoblot analysis of fraction 3 (A) from the gel filtration column demonstrated the presence of pleiotrophin. rh-PTN, human recombinant pleiotrophin used as a positive control. (C) Phase contrast photomicrograph of isolated ureteric bud grown for 7 days in the presence of fraction 3 supplemented with 10% FCS, 125 ng/ml GDNF, and 250 ng/ml of FGF1. Bar=500 μm.
Figure 3B:
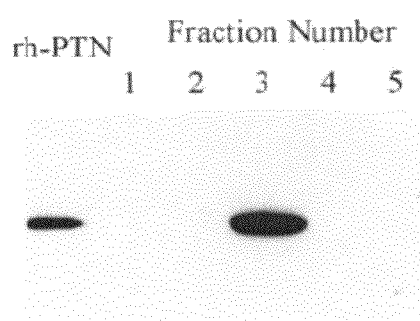
Figure 3C:
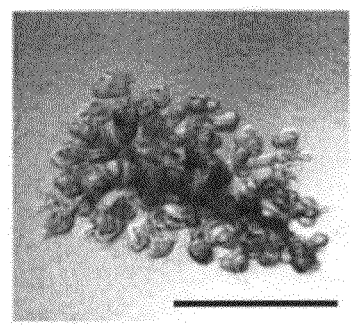

The presence of pleiotrophin in the active fraction (fraction 4) was confirmed by immunoblot analysis using anti-pleiotrophin antibodies (FIG. 2E). The morphogenetic activity of individual fractions corresponded to the presence of pleiotrophin in that fraction. In a similar fashion, further purification of the peak fraction from Resource S column was accomplished by applying the active fraction to a Superdex 200 gel filtration column. A single protein peak eluted at 15.93 ml (FIG. 3A), corresponding to a protein with a molecular weight of approximately 18 kDa, and was positive for pleiotrophin by immunoblot (FIG. 3B). This fraction induced isolated UB branching morphogenesis (FIG. 3C). Taken together, these results identify pleiotrophin as a morphogenetic factor present in BSN-CM.

Figure 4A:
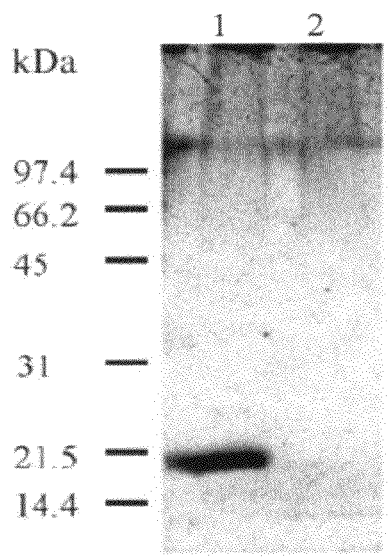
FIG. 4 demonstrates that adsorption of pleiotrophin abolishes morphogenetic activity. (A) Silver stained SDS-PAGE gel of morphogenetically active fraction from Resource S cation exchange column Lane 1, whole fraction Lane 2, fraction incubated with polyA-sepharose beads. The protein band at 18 kDa was not detected following treatment with polyA-sepharose beads. (B) Immunoblot analysis of the morphogenetically active fraction from Resource S cation exchange column. Lane 1, recombinant human pleiotrophin (positive control); Lane 2, active fraction; Lane 3, active fraction treated with polyA sepharose beads; Lane 4, protein bound to beads. The blot was probed with anti-pleiotrophin antibodies.
Figure 4B:
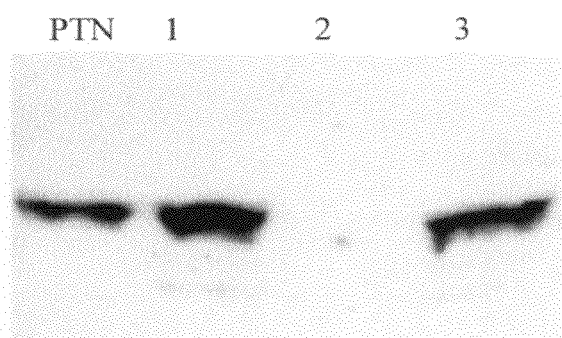
Figure 4C:
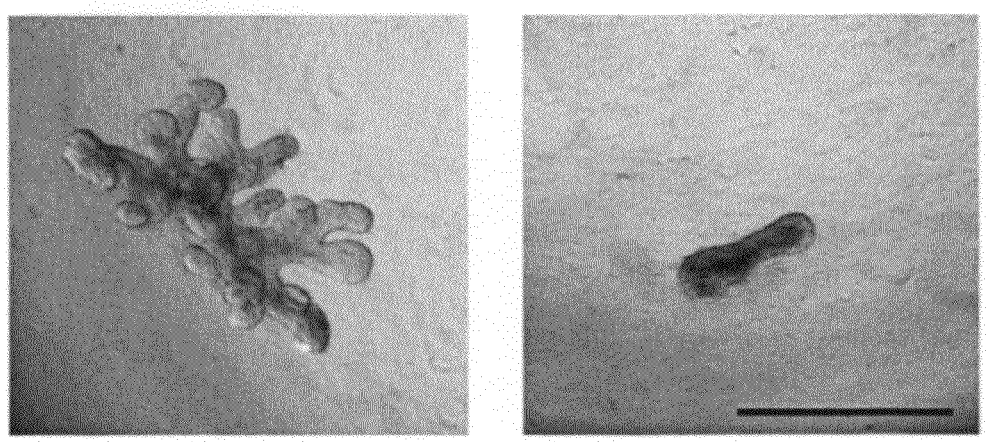

Previous studies have found that pleiotrophin can be isolated to homogeneity from a conditioned medium elaborated by Swiss 3T3 cells (Sato et al., 1999, supra). Thus, using this alternative purification procedure, a pure fraction of pleiotrophin was isolated from 3T3 conditioned medium (3T3-CM), as confirmed by silver stain, immunoblot analysis (FIGS. 4A and 4B) and mass spectrometry. Like the pleiotrophin that purified from BSN cells, this pure pleiotrophin was capable of inducing impressive branching morphogenesis of the isolated UB (FIG. 4C, left panel). Thus, pleiotrophin purified from two different cell lines gave the same results. However, ~10× concentrated whole 3T3-CM (culture media) failed to induce branching morphogenesis of the isolated UB, suggesting that 3T3-CM may contain an inhibitory factor.

Nevertheless, to provide further confirmation that pleiotrophin is the factor inducing the morphogenetic changes observed in the isolated UB culture the ability of polyA-sepharose to adsorb pleiotrophin. As seen in FIGS. 4A and 4B, treatment of purified pleiotrophin with polyA-sepharose beads results in the loss of detectable pleiotrophin, either by silver staining or immunoblot analysis. Importantly, this bead depleted fraction was no longer capable of inducing UB branching morphogenesis (FIG. 4C, right panel), providing further evidence that pleiotrophin is a morphogenetic factor for UB branching morphogenesis. Insect cell-derived recombinant human pleiotrophin is incapable of inducing proliferation and experiments using recombinant human pleiotrophin produced in the insect cell line (R&D systems) was also unable to induce UB branching morphogenesis.

Example 5

During the course of purification, differences in the morphology of the branching UB, depending upon the amount of pleiotrophin present in the fraction (detected by immunoblotting) was observed. This was examined more carefully using the purified protein in which the pleiotrophin concentration was determined by immunoblotting using recombinant human pleiotrophin as a standard. High concentration (>5 µg/ml) pleiotrophin resulted in robust proliferation with less elongation, while lower concentrations of pleiotrophin (156 ng/ml-2.5 pg/ml) induced dichotomous branching and elongation of the stalk (FIG. 5A), similar to that seen with whole BSN-CM.

Example 6

Figure 5B:
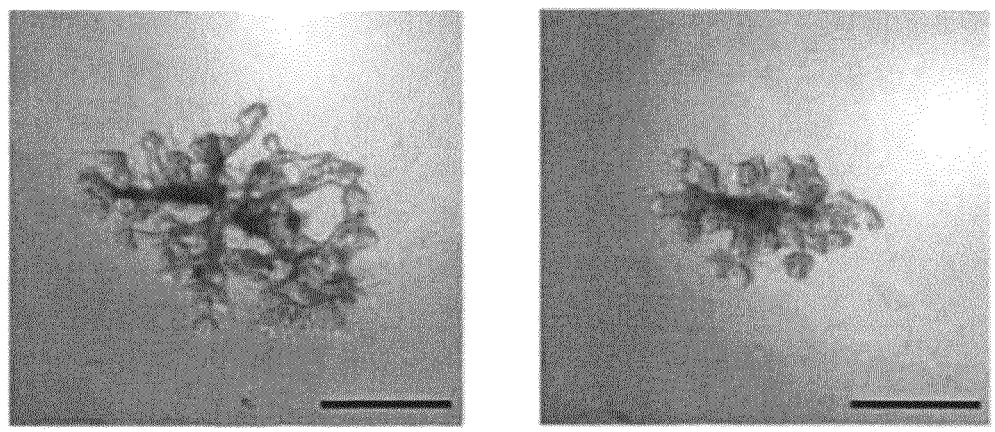

In the course of purification, variation in the inductive capacity of whole BSN-CM on UB branching was encountered. It was found that the addition of fibroblast growth factor 1 (FGF1) could potentiate the activity of the BSN-CM, although alone or in combination with GDNF it was not sufficient to induce isolated UB branching morphogenesis (FIG. 1C). Based on this finding, the growth media (either BSN-CM or individual fractions) used in the culture of the isolated UB was supplemented with 250 ng/ml of FGF1. However, it was found that purified pleiotrophin supplemented with GDNF was capable of inducing UB branching morphogenesis in the absence of FGF1, although the UB grew faster when FGF1 was added to the culture (FIG. 5B).

This result suggests that pleiotrophin and GDNF alone are necessary and sufficient for the observed branching morphogenesis of the isolated UB, though a FGF-like activity could play a role in the process.

Example 7

Figure 6A:
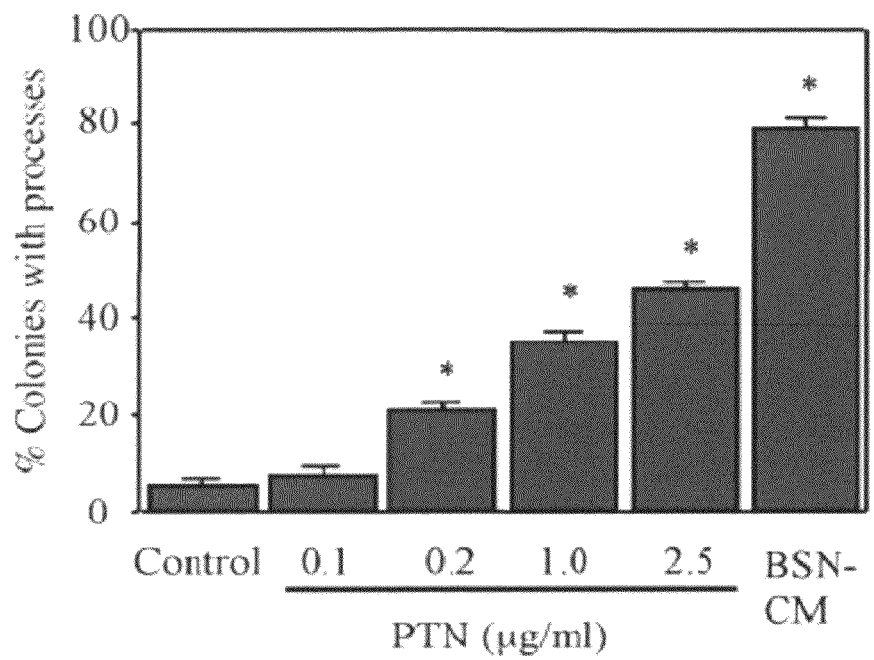
Figure 6B:
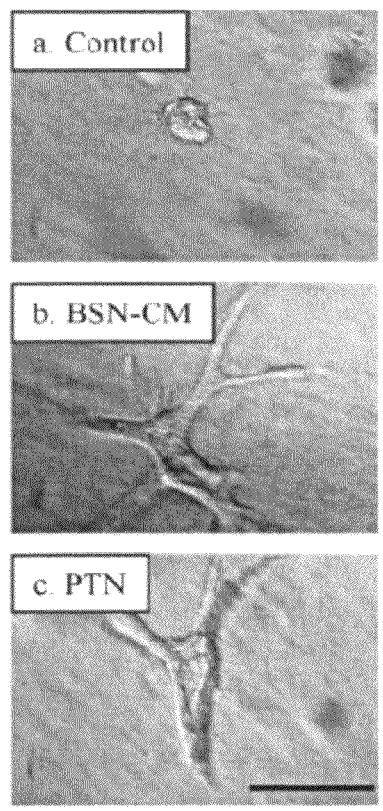

Pleiotrophin also induces branching morphogenesis of UBs in three dimensional culture. As discussed herein, E11 S mouse UB derived cells (UBs) develop into branching tubular structures with lumens in the presence of BSN-CM. DNA array, PCR analysis, and immunostaining have confirmed the epithelial and UB-like characteristics of these cells. Using this model for UB branching morphogenesis, pleiotrophin was also capable of inducing the formation of branching structures of UBs. As in the isolated UB culture model, the extent of UB branching morphogenesis was found to be concentration-dependent, with higher concentrations resulting in more extensive growth and branching (FIG. 6A). Morphologically, the structures were comparable to those induced by whole BSN-CM (FIG. 6B).

Example 8

Figure 7A:
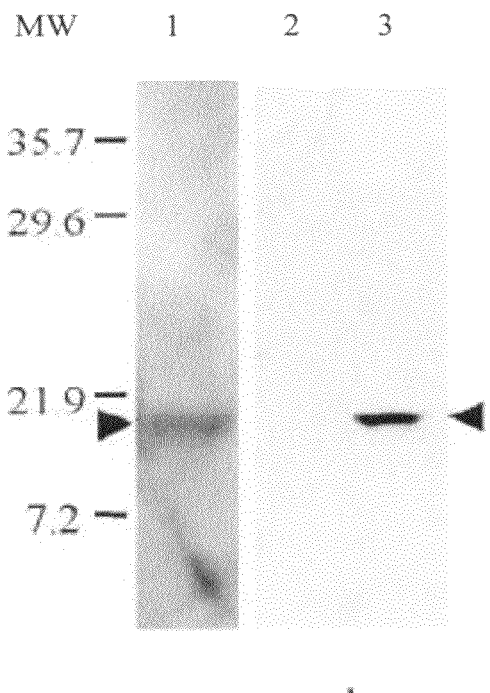
Figure 7B:
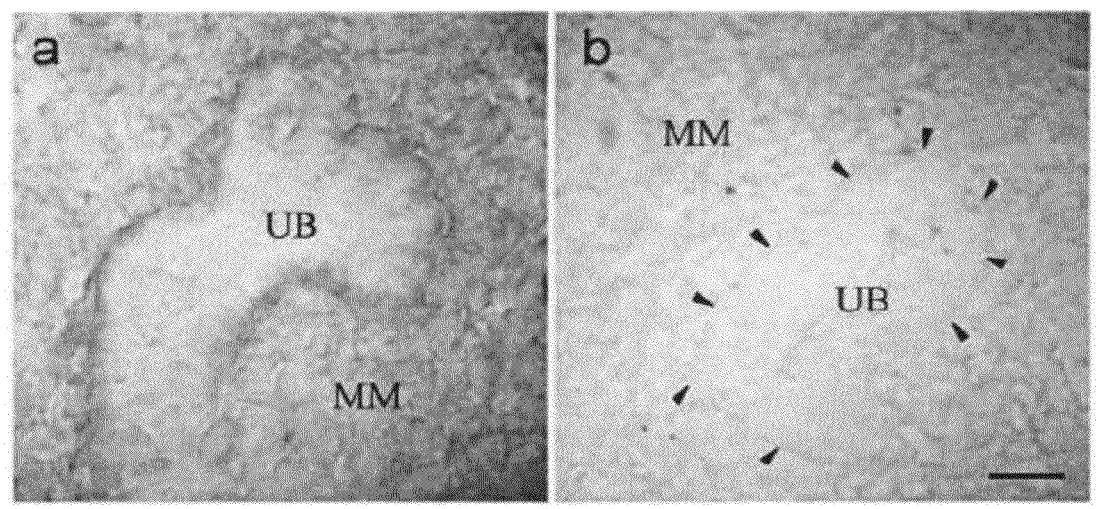

Pleiotrophin is expressed in the embryonic kidney and secreted from MM derived cells but not UB-derived cells. By immunoblot, pleiotrophin was found in an extract of whole embryonic day 13 rat kidney (FIG. 7A, a). To determine whether epithelial cells or mesenchymal cells secrete pleiotrophin, conditioned medium derived from the UB cell line and the BSN cell line were compared. Only BSN-CM contained pleiotrophin (FIG. 7A, b). This is consistent with a previous in situ hybridization study (Vanderwinden et al., Anat. Embryol (Berl) 186:387-406, 1992), which showed that the developing rat kidney mesenchyme (as early as E13 of development) expresses pleiotrophin mRNA, but the ureteric bud does not. Another study had suggested the presence of pleiotrophin in the basement membrane of epithelial tubules in the developing kidney of E13 mouse embryos (Mitsiadis et al., Development 121:37-51, 1995). When frozen sections of mouse E 13 kidneys stained with anti-pleiotrophin antibodies were examined, a strong signal was observed in the basement membrane of the UB with weak staining in the surrounding MM (FIG. 7B). Since the MM expresses pleiotrophin mRNA at the earliest stages of kidney development (Vanderwinden et al., 1992), the data presented herein suggest that pleiotrophin is secreted by the MM and binds to the basement membrane of the UB where it can exert its morphogenetic function.

Example 9

Exogenous pleiotrophin affects UB morphology in embryonic kidney organ culture. While the spatiotemporal expression pattern and in vitro data from the isolated UB and the UB cell culture model strongly support a direct role for pleiotrophin in UB morphogenesis, it was also important to determine its effect in a system that more closely approximates the intact developing kidney. To study this pleiotrophin was applied to whole embryonic kidney organ culture. Exogenously added pleiotrophin disproportionately stimulated growth of the UB (FIG. 8). Pleiotrophin-treated kidneys exhibited an expanded UB area in a concentration-dependent manner similar to that seen in the isolated UB culture (compare FIGS. 5A and 8).

Furthermore, the central area of UB expansion became more prominent at higher concentrations of pleiotrophin. The whole kidney also appeared slightly larger following pleiotrophin treatment. Nephron induction visualized with PNA lectin appeared to be normal even in the presence of high concentrations of pleiotrophin. Thus, not only isolated UB, but also the UB in the context of the whole embryonic kidney responded to pleiotrophin, supporting the notion that the UB is the target for pleiotrophin action in the developing kidney.

Based upon this data an essential role for direct contact between the metanephric mesenchyme (MM) and the ureteric bud (UB) during metanephrogenesis was suggested. Induction of the isolated MM was inhibited by the placement of a filter with c 0.1 µm pore size between an inducer and the MM, suggesting an absolute requirement for cell contact between the MM and an inducer. However, a combination of soluble factors elaborated by an immortalized UB cell line supplemented with either fibroblast growth factor (FGF)-2, or a combination of FGF2 and transforming growth factor are sufficient, in the absence of direct contact between the UB and MM, to induce the mesenchymal-epithelial transition and differentiation of the proximal nephron in cultures of isolated MM. Likewise, soluble factors produced by a MM cell line (BSN cells) supplemented with glial cell-derived neurotrophic factor (GDNF) have been suggested to be necessary and sufficient to induce extensive branching morphogenesis of the UB. Thus, soluble factors play a key role in both aspects of the mesenchymal-epithelial interaction leading to the formation of a functionally mature kidney. This constitutes an important revision in thinking relating to kidney organogenesis.

The identification of specific soluble factors (e.g., MM-derived soluble factors) mediating UB branching morphogenesis remains a central question in this field. Hepatocyte growth factor (HGF) has been shown to induce the formation of branching tubular structures with lumens in three-dimensional cultures of epithelial cell lines derived from adult kidneys (i.e., MDCK and mIMCD cells) (Barros et al., 1995; Cantley et al., 1994; Montesano et al., 1991; Santos et al., 1993). However, incubation of three-dimensional cultures of an embryonic cell line derived from the UB (UBs) with HGF had only a slight morphogenetic effect and the formation of branching tubular structures with lumens was not observed (Sakurai et al., 1997a). Furthermore, HGF, alone or in the presence of GDNF, does not induce branching morphogenesis of the isolated UB (as seen with the MM cell conditioned medium). These endings suggest that HGF is not an essential factor for early branching morphogenesis of the embryonic UB, though it may play a facilitory role. This notion is supported by the fact that genetic deletion of hgf or its receptor (c-met) apparently has little if any effect on kidney development (Bladt et al., 1995; Schmidt et al., 1995).

Example 10

When BSN-CM was treated with trypsin or exposure to prolonged heat (100° C.; 30 min), the morphogenetic activity for the UB was completely abolished. Based on this result, it is likely that the morphogenetic factor(s) in BSN-CM is proteinaceous in nature.

Centrifugation filtration systems with different nominal molecular weight cutoffs were used to concentrate BSN-CM. Centricon filters with a 8 kDa molecular mass cutoff membrane maintained biological activities in the retained fraction but not in the flow-through, suggesting the morphogenetic activity is larger than 8 kD.

Example 11

As we have already discussed, the morphogenetic factor is heparin binding. Thus, a heparin binding-column (Hitrap Heparin, Amersham-Pharmacia) was employed. Each fraction was assayed in isolated UB culture system in the presence of GDNF and FGF-1. Strong proliferative/morphogenetic activity was observed in the fractions eluted with 0.9-1.25 M NaCl (FIG. 9). These morphogenetically active fractions were adjusted to 1.7 M ammonium sulfate and were applied to the Phenyl Sepharose column at pH 7.2. Isolated UB culture showed that several different activities were present in fractions eluted between 1.5-0.7 M ammonium sulfate, The 1.5-1.35 M eluate fraction in FIG. 10 induced UB proliferation but had little effect on branching tubule formation or elongation. In contrast, the 0.9-0.7 M eluate (fraction 10 in FIG. 10) exhibited branching morphogenesis and elongation, but less robust proliferation. Interestingly, the activity found in fractions 7-9 suggested a combination of both fraction 6 and 10. This result suggests that although full-blown branching morphogenesis (as seen in the UB culture in fraction 9) may require a combination of multiple factors (e.g., a proliferative factor present in fraction 6 plus a possible elongation/branching factor present in fraction 10), individual factors can be separated and purified. In fact, by SDS-PAGE and silver staining (FIG. 10, lower left panel), fraction 6, which appears to be mainly proliferative, contains a few bands clustered between 18-31 kDa, while fraction 10, which appears to promote elongation and branching, contains only one band visible at 31 kDa.

Example 12

Sequential use of a hydrophobic interaction column, a cation exchange column, and a gel filtration column lead to the purification of PTN from these heparin-bound active fractions. However, as discussed above, BSN-CM is likely to contain more than one morphogenetic factors. In fact while higher salt eluate fractions (fraction 6 in FIG. 11) from phenyl sepharose column contained PTN by western blotting, lower salt eluate from a phenyl sepharose column (fraction 10 in FIG. 12) did not. In addition, when morphogenetically active fractions eluted from a heparin column (adjusted to Tris HCl buffer pH 8.0) were applied to an anion exchange (Q) column, morphogenetic activity was eluted at 0.15-0.5 M NaCl fractions (4 and 5 in FIG. 11). This morphogenetic activity was preserved after applying these fractions to a gel filtration column. This Q column-bound activity is unlikely to be PTN because PTN (pI=9.3) should not bind to the Q column at pH 8.0. By microsequencing analysis, a heparin binding growth factor heregulin was present in these fractions. This result was further confirmed by western blotting, which was positive for heregulin alpha in these fractions. Recombinant human heregulin alpha (250 µg/ml) induced isolated UB to grow to the similar morphology as fractions 4 and 5 in FIG. 11 in the presence of GDNF and FGF1. Thus, it is very likely that heregulin is one of the factors that induce UB growth.

Example 13

Heparin-bound fractions of BSN-CM are likely to contain many morphogenetic growth-promoting factors other than PTN. Existence of such factors are highly likely for the following reasons: (1) an active fraction eluted from anion exchange (Q) column is not likely to contain PTN (see FIG. 1); (2) a fraction elated from a phenyl sepharose column at 0.7 M ammonium sulfate (fraction 10 in FIG. 10), which induced elongation and branching of the UB tubules, should not contain PTN. Considering the relatively low resolution of hydrophobic interaction column, the existence of very low concentrations of PTN cannot be excluded, however, a dose dependent response suggests that it is unlikely that such a low concentration of PTN can induce the UB morphogenesis observed; and (3) a morphogenetically active fraction containing little, if any, PTN by western blotting was obtained by sequential chromatography over 3 columns including a heparin sepharose column (FIG. 12).

Example 14

Tissue culture media was obtained from Mediatech and bovine fetal calf serum was obtained from Biowhittiker. Growth factor reduced Matrigel and Type I collagen were obtained from Becton Dickenson. FGF1 and GDNF were obtained from R&D systems. FITC-conjugated DB were obtained from Vector Laboratories.

The Cellmax artificial capillary cell culture system was inoculated with BSN cells, and conditioned media harvested as described herein.

Uteri from timed pregnant Sprague-Dawley rats corresponding to gestational day 13 were harvested and embryos isolated. Embryonic kidneys were isolated and cultured on top of a Transwell filter in the presence of DMEM/F12 media supplemented with 10% FCS. The kidneys were cultured at 37° C. in fully humidified 5% $CO_2$ atmosphere. At the specified time intervals, the embryonic kidneys were sectioned into thirds and subcultured on filters with fresh media.

Isolated ureteric buds were obtained from whole embryonic kidneys as previously described. Briefly, the embryonic kidney was digested with trypsin and the UB separated from the MM using fine-tipped needles. The UBs were suspended within a matrix containing growth factor reduced Matrigel and Type I collagen and buffered by HEPES, $NaHCO_3$, and DMEM to a pH of approximately 7.2. This mixture containing the suspended UB was applied to the top of the Transwell filter and BSN-conditioned media added to the well. The BSN conditioned media is supplemented with GDNF (125 ng/ml) and FGF1 (31 ng/ml) and 10% FCS, and the isolated UBs cultured at 37° C. and humidified 5% $CO_2$ atmosphere. At specified time intervals, the cultured UB is separated from the surrounding matrix by blunt microdissection, sectioned into thirds, resuspended in new matrix and cultured with fresh supplemented BSN conditioned media.

Example 15

Isolated metanephric mesenchyme were isolated as described above and cultured on top of the Transwell filter. DMEM/F12 media supplemented with FGF2 (100 ng/ml) and TGFα (10 ng/ml) was added to the well to prevent MM apoptosis.

Example 16

Using blunt microdissection with fine tipped needles, cultured or subcultured UBs were cleanly separated from surrounding matrix and placed on top of a Transwell filter in close proximity to MM that was either freshly isolated or cultured. BSN conditioned media supplemented with GDNF, FGF1 and 10% FCS was added to the well.

Cultured or subcultured embryonic kidneys, isolated buds, and recombined kidneys were fixed in 4% paraformaldehyde and processed for immunofluorescent staining with either FITC-conjugated DB or antibodies. Immunofluorescence was detected with a Zeiss laser-scanning confocal microscope.

Example 17

Adult male rats (weighing 200-250 grams) were housed and fed on standard rat chow, water ingestion and 12-hour cycles of light and dark. All animals were maintained and experiments conducted in accord with the National Institutes of Health (NM) Guide for the care and Use of Lab Animals.

Rats were anesthetized with an intraperitoneal injection of sodium pentobarbital solution (50 mg/kg). The anesthetized animals were placed on a warming blanket and a midline abdominal incision made. Bilateral or unilateral occlusion of the renal pedicule were maintained for 40 minutes to induce ischemia and the incision temporarily closed until completion of vascular occlusion. If an arterial catheter was required for the experiment one was placed in the femoral artery and exteriorized in the dorsal scapular region. If ureteral catheters were necessary, they were placed and exteriorized. Upon completion of ischemic period, the arterial occlusion are removed, the incisions were sutured or stapled closed and the rats allowed to recover for designated reperfusion time.

Example 18

Injury was induced with either mercuric chloride or the antibiotic gentamicin. Mercuric chloride primarily induces injury and subsequent cell proliferation in proximal straight tubules (PST), whereas gentamicin predominantly injures proximal convoluted tubules (PCT). Gentamicin nephrotoxicity were induced by LP injections of 40 mg/ml in 0.9 percent saline, divided with three daily injections over two days for a total of 400 mg/kg. Mercuric chloride are administered at various doses (0.25, 0.5, 1.0 and 2.5 mg/kg). These doses have been reported to induce renal injury ranging from minimal to marked.

Example 19

To mimic the usual clinical situation, some rats were exposed to either gentamicin or mercuric chloride at the ischemic injury. The renal injury was especially severe in these animals.

To purify factors involved in embryonic nephrogenesis, BSN cell conditioned media (BSN-CM) was collected after 2 to 4 days of BSN cell confluency, spun at low speed to remove cell debris and filtered (0.22 μm filter). The media is then concentrated (Vivaflow 200, 5 kDA cutoff) subjected to sequential liquid column chromatography and ion techniques, and final purification accomplished with HPLC and SDS-Page electrophoresis. The final purified protein(s) was submitted for microsequencing to an out side vender.

Example 20

Isolated ureteric buds were obtained from whole embryonic kidneys as described herein. Briefly, the embryonic kidney was lightly digested with trypsin and the UB were separated from the MM using fine-tipped needles. The UBs were suspended within a matrix containing growth factor reduced Matrigel and Type I collagen and buffered by HEPES, $NaHCO_3$, and DMEM to a pH of approximately 7.2. This mixture containing the suspended UB was applied to the top of the Transwell filter and the purified factor is applied to the well. The factor is supplemented with GDNF (125 ng/ml) and 10% FCS, and the isolated UBs are cultured at 37° C. and humidified 5% $CO_2$ atmosphere and branching morphogenesis, was assayed.

Example 21

Plasma collections during the experiment were collected via the rat tail vein under isoflurane anaesthesia. A large blood volume was collected at the end of the experimental period by sanguination under pentobarbitol (50 mg/kg) anacstiesia. Plasma from these collections were analyzed for sodium, potassium, ionized calcium, ionized magnesium. (Nova 8 Electrolyte Analyzer), BUN and crealinine by autoanalyzer (core facility). Urine collection during and at the end of the experiment were done in metabolic cages. The urine was analyzed colormetrically for creatinine, calcium, magnesium, phosphate and chloride and protein. Sodium and potassium are measured with a Nova 6 Electrolyte Analyzer.

Example 22

Cross sections of kidney from each rat were fixed on a microscope slide and stained with hematoxylin and eosin. Slides were read for the presence or absence of tubular epithelial degeneration and/or necrosis.

Example 23

Tubular injury and cell proliferation were assessed on PCNA/PAS sections. Staining was done on 5 μm paraffin sections from ethacam-fixed renal tissue. Proliferating cells were immunostained with a rabbit anti-mouse monoclonal antibody (PC 10 from Dako) directed to proliferating cell nuclear antigen (PCNA). After blocking (goat sera) and incubation with the primary antibody, the sections were incubated with biotinylated goat-anti rabbit antiserum in the presence of normal rat serum and stained by the avidin-biotinylated horseradish peroxidase complex (Vectastatin, Vector Labs) using 3,3'-diaminobenzidine as the chromogen. Sections were then counterstained with methyl green and periodic acid-Schiff (PAS).

Example 24

Identification and determination of apoptosis was done using the terminal deoxynucleotidyl transferase (TdT)-mediated UTP biotin nick-end labeling (TUNEL) technique by using an Apoptag in situ apoptosis detection kit (Oncor, Gaitheburg, Md.). Frozen sections (Sum) were fixed in 10% neutral-buffered red formalin and post fixed in ethanol: acetic acid at −20° C. for comparison to control tissue as described herein.

Example 25

Determination of the factor(s) was also performed in adult rat kidney: After purification of unique factor(s) an antibody was generated by immunizing rabbits with purified protein (Multiple Peptide Systems, San Diego, Calif.). Kidney homogenates following ischemic and/or nephrotoxin injury were fractionated on 4-15% SDS polyacrylamide gels under reducing conditions and transferred to PVDF membranes. After blocking with phosphate buffered saline containing 5% non-fat milk, the blots were incubated Primary antibody (rabbit anti-rat peptide) and visualized by enhanced chemiluminescence system (Pierce). If peptide was present by western blot analysis then the polyclonal was used for immunohistochemical detection and localization.

Example 26

Isolation of ureteric bud (UB) epithelium and UB culture. Kidney rudiments were dissected from timed pregnant Sprague Dawley rats at gestation day 13. (The plug day was designated as day 0). The UB was isolated from mesenchyme by incubating kidney rudiments in 0.1% trypsin in the presence of 50 U/ml DNAase at 37° C. for 15 minutes, and by mechanical separation with two fine-tipped minutia pins. For culture, Transwell tissue culture plates and a polycarbonate membrane insert with 3 um pore size were used. The extracellular matrix (ECM) gel (a mixture of type I collagen and Matrigel) was applied on top of the Transwell insert. isolated UB was suspended in the ECM gel and cultured at the interface of air and medium. All cultures were carried out at 37° C. with 5% $CO_2$ and 100% humidity in DMEM/F12 supplemented with 10% Fetal Calf Serum (FCS). Growth factors were added as indicated elsewhere. Culture media were changed weekly if necessary.

Example 27

Cells and conditioned media: The BSN cell line was derived from day 11.5 mouse embryonic kidney metanephric mesenchyme originally obtained from a mouse line transgenic for the early region of SV-40/large T antigen. As described elsewhere, the BSN cells express the emsenchymal protein marker vimentin, but not classic epithelial marker proteins such as cytokeratin, ZO-1 and E-cadherin. Differences in the expression patterns of 588 genes in BSN cells have been analyzed by the inventors on commercially available cDNA grids (Am. J. Physiol.-Renal Physiol., 277, F:650-F663, 1999), and cnfirmed the largely non-epithelial character of BSN-cells, though it remains to be determined whether they 10 are mesenchymal or stromal, or have chracteristics of both cell types. The SV-40/large T antigen transformed UB cell line and routine inner-medulla collecting duct (mIMCD) cells have been extensively characterized before. To obtain conditioned media, a confluent cell monolayer was washed with serum-free medium, and then cultured in serum free medium for another 2-4 days.

Various conditioned media were harvested after low speed centrifugation to remove cell debris and then concentrated 10-fold with a Centricon filter with 8 kDa nominal molecular weight cutoff (Millipore, Bedford, Mass.). In addition, BSN-CM was subfractionated on a heparin-sepharose affinity column (Hitrap Heparin; Pharmacia, N.J.). Concentrated BSN-CM (.about.10x) was applied to a heparin column. After washing the column with Hanks' balanced buffer solution, the heparin bound fraction was eluted with 2 M NaCl in Hanks' balanced buffer solution. After desalting with a PD-10 column (Pharmacia, N.J.), the heparin bound fraction's final volume was adjusted to the starting volume. The herparin flow through fraction was collected and its volume was adjusted to the starting volume using a Centricon filter (8 kDa cutoff). The partially purified fractions were assayed for their effect on UB morphogenesis in the presence of GDNF.

Example 28

The ECM gel mix: The ECM gel mix was composed of 50% type I collagen (Collaborative Biomedical Product) and 50% growth factor-reduced Matrigel (Collaborative Biomedical Product). The procedure for gelation has been previously described in detail and is incorporated herein.

Example 29

Induction of nephrogenesis by cultured UB: Isolated UBs were first cultured for 7-10 days as already described. Then, the cultured UB was isolated from the ECM gel by incubation with collagenase (1 mg/ml) and dispase (2 ml/ml) at 37° C. for 30 minutes, followed by mechanical separation with fine tipped minutia pins. The UB was then recombined with freshly isolated E-13 rat metanephric mesenchyme and co-cultured on a transfilter for another 5 days in DMEM/F12, plus 10% FCS.

Example 30

Lectin staining: 1) Dolichos Biflorus (DB) lectin: Tissues were fixed with 2% paraformaldehyde for 30 minutes at 4.degree. C., permeabilized with 0.1% Saponin and then incubated with fluorescent conjugated DB (50 ug/ml, Vector) in a moisturized chamber for 60 minutes at 37° C. After extensive cashing, tissues were post-fixed in 2% paraformaldehyde again for 5 minutes and viewed using a laser scanning confocal microscope. The specificity of DB lectin binding has been demonstrated previously. 2) Peanut agglutinin (PNA) lectin: Tissues were fixed with 2% paraformaldehyde for 30 minutes at 4° C.; blocked with 50 mM $NH_4Cl$ overnight at 4° C., followed by an incubation with 1% gelatin in 0.075% Saponin for 30 minutes at 37° C. After two washes with Neuraminidase buffer (150 mM NaCl, 50 mM Na-Acetate, pH 5.5), tissues were incubated with Neuraminidase (1 U/ml) for 4 hours at 37° C. and then Rhodamine-conjugated PNA (50 ug/ml) for 60 minutes at 37° C. Tissues were post-fixed with 2% paraformaldehyde and viewed with a laser scanning confocal microscope.

Example 31

Immunocytochemistry: Tissues were fixed with either 2% paraformaldehyde at 4° C. or 100% methanol at −20° C. Tissues were permeablized with 0.1% Saponin and non-specific binding was blocked with fetal 100% FCS. The incubations with primary and secondary antibodies were carried out for 60 minutes at 37° C. The staining with FITC or TRITC-confugated antibodies was viewed with a laser scanning confocal microscope.

Example 32

Confocal Analysis: Confocal images were collected with a laser scanning confocal microscope (Bio-Rad MRC 1024, Bio-Rad, CA). Each three-dimensional picture was reconstructed from a set of 10 um serial sections, which spanned the tissue. Images were processed with Laser Sharp™ (Bio-Rad) and Photoshop™ (Adobe, CA) software.

A number of embodiments of the invention have been described. Nevertheless, it will be understood that various modifications may be made without departing from the spirit and scope of the invention. Accordingly, other embodiments are within the scope of the following claims.

What is claimed is:

1. A method for growing renal tubule cells in vitro, comprising culturing kidney cells in a growth medium comprising (i) purified pleiotrophin and/or purified heregulin, and (ii) fibroblast growth factor-1 (FGF-1), glial-derived neurotrophic factor (GDNF) or a combination thereof, in an amount effective for achieving tubulogenesis.

2. The method of claim 1, wherein the growth medium comprises a factor selected from the group consisting of Type I collagen, Type IV collagen, laminin, proteoglycans, fibronectin, and combinations thereof.

3. A method for stimulating branching morphogenesis in a kidney cell culture, comprising:
    (a) contacting the kidney cell culture with a composition comprising one or more purified mesenchymally derived growth factor(s) secreted by a mesenchyme tissue in culture in an amount effective to stimulate branching tubulogenesis in the kidney cell culture, wherein the one or more mesenchymally derived growth factor(s) include pleiotrophin and, optionally, heregulin; and
    (b) culturing the kidney cell culture in the composition for a period of time and under conditions effective to stimulate branching morphogenesis.

4. The method of claim 3, wherein the kidney cell culture comprises ureteric bud cells.

5. The method of claim 3, wherein the kidney cell culture comprises ureteric bud cells and metanephric mesenchyme cells.

6. The method of claim 3, wherein the composition further comprises GDNF and/or FGF1.

7. The method of claim 3, wherein at least one of the one or more mesenchymally derived growth factor is secreted by metanephric mesenchyme tissue in culture.

8. The method of claim 7, wherein at least one of the one or more mesenchymally derived growth factor is from BSN cell conditioned medium.

9. The method of claim 3, wherein at least one of the one or more mesenchymally derived growth factor is a heparin-binding polypeptide.

10. The method of claim 3, wherein the pleiotrophin and/or heregulin is obtained from culture medium of a metanephric mesenchymal culture.

11. The method of claim 10, wherein the pleiotrophin and/or heregulin is obtained from BSN cell conditioned medium.

12. The method of claim 3, wherein the pleiotrophin and/or heregulin is recombinant pleiotrophin and/or heregulin.

13. The method of claim 12, wherein the recombinant pleiotrophin and/or heregulin is a peptidomimetic pleiotrophin and/or heregulin.

14. The method of claim 3, wherein the pleiotrophin and/or heregulin are pleiotrophin and/or heregulin analogues.

15. The method of claim 3, wherein the pleiotrophin and/or heregulin are synthetic pleiotrophin and/or heregulin analogues.

* * * * *

UNITED STATES PATENT AND TRADEMARK OFFICE
CERTIFICATE OF CORRECTION

| | | |
|---|---|---|
| PATENT NO. | : 8,148,149 B2 | |
| APPLICATION NO. | : 12/009030 | |
| DATED | : April 3, 2012 | |
| INVENTOR(S) | : Sanjay Kumar Nigam, Hiroyuki Sakurai and Kevin T. Bush | |

It is certified that error appears in the above-identified patent and that said Letters Patent is hereby corrected as shown below:

Replace lines 27-30 of column 1 with the following:

-- This invention was made with Government Support under Grant Nos. RO1-DK53507 and RO1-DK51211 awarded by the National Institute of Diabetes and Digestive and Kidney Diseases. The U.S. Government has certain rights in this invention. --

Signed and Sealed this
Thirty-first Day of July, 2012

David J. Kappos
*Director of the United States Patent and Trademark Office*